United States Patent
Raitano et al.

(10) Patent No.: US 7,507,541 B2
(45) Date of Patent: *Mar. 24, 2009

(54) 36P6D5: SECRETED TUMOR ANTIGEN

(75) Inventors: Arthur B. Raitano, Los Angeles, CA (US); Aya Jakobovits, Beverly Hills, CA (US); Mary Faris, Los Angeles, CA (US); Daniel E. H. Afar, Fremont, CA (US); Rene S. Hubert, Los Angeles, CA (US); Steve Chappell Mitchell, Gurnee, IL (US)

(73) Assignee: Agensys, Inc., Santa Monica, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/805,969

(22) Filed: May 24, 2007

(65) Prior Publication Data
US 2008/0019971 A1    Jan. 24, 2008

Related U.S. Application Data

(62) Division of application No. 10/365,254, filed on Feb. 11, 2003, now Pat. No. 7,223,542, which is a division of application No. 09/702,114, filed on Oct. 30, 2000, now Pat. No. 6,566,078.

(60) Provisional application No. 60/162,417, filed on Oct. 28, 1999.

(51) Int. Cl.
G01N 33/53    (2006.01)
(52) U.S. Cl. ....................................... 435/7.1
(58) Field of Classification Search ............ 435/7.1
See application file for complete search history.

(56) References Cited

U.S. PATENT DOCUMENTS

| | | | |
|---|---|---|---|
| 6,093,800 A | 7/2000 | Reiter et al. | |
| 2002/0127643 A1 | 9/2002 | Baker et al. | |
| 2002/0132768 A1 | 9/2002 | Baker et al. | |
| 2002/0132981 A1 | 9/2002 | Baker et al. | |
| 2002/0142419 A1 | 10/2002 | Baker et al. | |
| 2002/0142958 A1 | 10/2002 | Baker et al. | |
| 2002/0142959 A1 | 10/2002 | Baker et al. | |
| 2002/0150976 A1 | 10/2002 | Baker et al. | |
| 2002/0156004 A1 | 10/2002 | Baker et al. | |
| 2002/0165143 A1 | 11/2002 | Baker et al. | |
| 2002/0168715 A1 | 11/2002 | Baker et al. | |
| 2002/0173463 A1 | 11/2002 | Baker et al. | |
| 2002/0177165 A1 | 11/2002 | Ashkenazi et al. | |
| 2003/0004311 A1 | 1/2003 | Baker et al. | |
| 2003/0017563 A1 | 1/2003 | Baker et al. | |
| 2003/0022239 A1 | 1/2003 | Baker et al. | |
| 2003/0022328 A1 | 1/2003 | Baker et al. | |
| 2003/0022331 A1 | 1/2003 | Baker et al. | |
| 2003/0027270 A1 | 2/2003 | Baker et al. | |
| 2003/0027275 A1 | 2/2003 | Baker et al. | |
| 2003/0027276 A1 | 2/2003 | Baker et al. | |
| 2003/0032057 A1 | 2/2003 | Ashkenazi et al. | |
| 2003/0032062 A1 | 2/2003 | Ashkenazi et al. | |
| 2003/0032063 A1 | 2/2003 | Ashkenazi et al. | |
| 2003/0032155 A1 | 2/2003 | Baker et al. | |
| 2003/0032156 A1 | 2/2003 | Baker et al. | |
| 2003/0036179 A1 | 2/2003 | Baker et al. | |
| 2003/0036180 A1 | 2/2003 | Baker et al. | |
| 2003/0040014 A1 | 2/2003 | Ashkenazi et al. | |
| 2003/0044844 A1 | 3/2003 | Ashkenazi et al. | |
| 2003/0044902 A1 | 3/2003 | Ashkenazi et al. | |
| 2003/0044945 A1 | 3/2003 | Baker et al. | |
| 2003/0049816 A1 | 3/2003 | Baker et al. | |
| 2003/0049817 A1 | 3/2003 | Baker et al. | |
| 2003/0054516 A1 | 3/2003 | Baker et al. | |
| 2003/0054517 A1 | 3/2003 | Baker et al. | |
| 2003/0059909 A1 | 3/2003 | Baker et al. | |
| 2003/0068793 A1 | 4/2003 | Baker et al. | |
| 2003/0068794 A1 | 4/2003 | Baker et al. | |
| 2003/0068795 A1 | 4/2003 | Baker et al. | |
| 2003/0068796 A1 | 4/2003 | Baker et al. | |
| 2003/0068797 A1 | 4/2003 | Baker et al. | |
| 2003/0068798 A1 | 4/2003 | Baker et al. | |
| 2003/0073105 A1 | 4/2003 | Lasek et al. | |
| 2003/0073210 A1 | 4/2003 | Baker et al. | |
| 2003/0073211 A1 | 4/2003 | Baker et al. | |
| 2003/0073212 A1 | 4/2003 | Baker et al. | |
| 2003/0073213 A1 | 4/2003 | Baker et al. | |
| 2003/0073214 A1 | 4/2003 | Baker et al. | |
| 2003/0073215 A1 | 4/2003 | Baker et al. | |
| 2003/0073216 A1 | 4/2003 | Baker et al. | |
| 2003/0077698 A1 | 4/2003 | Baker et al. | |
| 2003/0082686 A1 | 5/2003 | Baker et al. | |
| 2003/0082687 A1 | 5/2003 | Baker et al. | |
| 2003/0082689 A1 | 5/2003 | Baker et al. | |
| 2003/0082690 A1 | 5/2003 | Baker et al. | |
| 2003/0082691 A1 | 5/2003 | Baker et al. | |
| 2003/0082692 A1 | 5/2003 | Baker et al. | |
| 2003/0082693 A1 | 5/2003 | Baker et al. | |
| 2003/0082694 A1 | 5/2003 | Baker et al. | |
| 2003/0082695 A1 | 5/2003 | Baker et al. | |
| 2003/0082696 A1 | 5/2003 | Baker et al. | |
| 2003/0082697 A1 | 5/2003 | Baker et al. | |
| 2003/0082698 A1 | 5/2003 | Baker et al. | |
| 2003/0082699 A1 | 5/2003 | Baker et al. | |
| 2003/0082700 A1 | 5/2003 | Baker et al. | |

(Continued)

FOREIGN PATENT DOCUMENTS

EP    1033401    9/2000

(Continued)

OTHER PUBLICATIONS

Tockman et al (Cancer Res., 1992, 52:2711s-2718s).*

(Continued)

*Primary Examiner*—Sean E Aeder
(74) *Attorney, Agent, or Firm*—Morrison & Foerster LLP

(57) ABSTRACT

Described is a gene and its encoded secreted tumor antigen, termed 36P6D5, and to diagnostic and therapeutic methods and compositions useful in the management of various cancers which express 36P6D5, particularly including cancers of the bladder, kidney, prostate, breast, colon, ovary and pancreas.

26 Claims, 12 Drawing Sheets

U.S. PATENT DOCUMENTS

| | | |
|---|---|---|
| 2003/0082701 A1 | 5/2003 | Baker et al. |
| 2003/0082702 A1 | 5/2003 | Baker et al. |
| 2003/0082703 A1 | 5/2003 | Baker et al. |
| 2003/0082704 A1 | 5/2003 | Baker et al. |
| 2003/0082705 A1 | 5/2003 | Baker et al. |
| 2003/0082706 A1 | 5/2003 | Baker et al. |
| 2003/0082708 A1 | 5/2003 | Baker et al. |
| 2003/0082709 A1 | 5/2003 | Baker et al. |
| 2003/0082710 A1 | 5/2003 | Baker et al. |
| 2003/0082711 A1 | 5/2003 | Baker et al. |
| 2003/0082712 A1 | 5/2003 | Baker et al. |
| 2003/0082715 A1 | 5/2003 | Baker et al. |
| 2003/0082759 A1 | 5/2003 | Baker et al. |
| 2003/0082760 A1 | 5/2003 | Baker et al. |
| 2003/0082761 A1 | 5/2003 | Baker et al. |
| 2003/0082762 A1 | 5/2003 | Baker et al. |
| 2003/0082763 A1 | 5/2003 | Baker et al. |
| 2003/0082764 A1 | 5/2003 | Baker et al. |
| 2003/0082765 A1 | 5/2003 | Baker et al. |
| 2003/0082766 A1 | 5/2003 | Baker et al. |
| 2003/0083479 A1 | 5/2003 | Baker et al. |
| 2003/0087344 A1 | 5/2003 | Baker et al. |
| 2003/0087345 A1 | 5/2003 | Baker et al. |
| 2003/0087346 A1 | 5/2003 | Baker et al. |
| 2003/0087347 A1 | 5/2003 | Baker et al. |
| 2003/0087349 A1 | 5/2003 | Baker et al. |
| 2003/0087350 A1 | 5/2003 | Baker et al. |
| 2003/0087351 A1 | 5/2003 | Baker et al. |
| 2003/0087352 A1 | 5/2003 | Baker et al. |
| 2003/0087353 A1 | 5/2003 | Baker et al. |
| 2003/0087354 A1 | 5/2003 | Baker et al. |
| 2003/0087355 A1 | 5/2003 | Baker et al. |
| 2003/0087356 A1 | 5/2003 | Baker et al. |
| 2003/0087357 A1 | 5/2003 | Baker et al. |
| 2003/0087358 A1 | 5/2003 | Baker et al. |
| 2003/0087359 A1 | 5/2003 | Baker et al. |
| 2003/0087360 A1 | 5/2003 | Baker et al. |
| 2003/0087361 A1 | 5/2003 | Baker et al. |
| 2003/0087362 A1 | 5/2003 | Baker et al. |
| 2003/0087363 A1 | 5/2003 | Baker et al. |
| 2003/0087364 A1 | 5/2003 | Baker et al. |
| 2003/0087365 A1 | 5/2003 | Baker et al. |
| 2003/0087366 A1 | 5/2003 | Baker et al. |
| 2003/0087367 A1 | 5/2003 | Baker et al. |
| 2003/0092103 A1 | 5/2003 | Baker et al. |
| 2003/0092104 A1 | 5/2003 | Baker et al. |
| 2003/0092105 A1 | 5/2003 | Baker et al. |
| 2003/0092106 A1 | 5/2003 | Baker et al. |
| 2003/0092107 A1 | 5/2003 | Baker et al. |
| 2003/0092108 A1 | 5/2003 | Baker et al. |
| 2003/0092110 A1 | 5/2003 | Baker et al. |
| 2003/0092111 A1 | 5/2003 | Baker et al. |
| 2003/0092113 A1 | 5/2003 | Baker et al. |
| 2003/0092115 A1 | 5/2003 | Baker et al. |
| 2003/0092147 A1 | 5/2003 | Baker et al. |
| 2003/0096386 A1 | 5/2003 | Baker et al. |
| 2003/0096742 A1 | 5/2003 | Baker et al. |
| 2003/0100087 A1 | 5/2003 | Baker et al. |
| 2003/0100497 A1 | 5/2003 | Baker et al. |
| 2003/0104558 A1 | 6/2003 | Ashkenazi et al. |

FOREIGN PATENT DOCUMENTS

| | | |
|---|---|---|
| WO | WO-99/06439 | 2/1999 |
| WO | WO-99/18209 | 4/1999 |
| WO | WO-99/28462 | 6/1999 |
| WO | WO-99/40189 | 8/1999 |
| WO | WO-99/49023 | 9/1999 |
| WO | WO-99/56778 | 11/1999 |
| WO | WO-00/03791 | 1/2000 |
| WO | WO-00/27491 | 6/2000 |
| WO | WO-00/32776 | 6/2000 |
| WO | WO-00/37491 | 6/2000 |
| WO | WO-00/77037 | 12/2000 |
| WO | WO-01/00806 | 1/2001 |
| WO | WO-01/31015 | 5/2001 |
| WO | WO-01/40466 | 6/2001 |
| WO | WO-01/46229 | 6/2001 |
| WO | WO-01/55437 | 8/2001 |
| WO | WO-01/60860 | 8/2001 |
| WO | WO-01/92581 | 12/2001 |
| WO | WO-01/94629 | 12/2001 |
| WO | WO-02/00690 | 1/2002 |
| WO | WO-02/02807 | 1/2002 |
| WO | WO-02/08284 | 1/2002 |
| WO | WO-02/12440 | 2/2002 |
| WO | WO-02/058534 | 8/2002 |
| WO | WO-03/008446 | 1/2003 |
| WO | WO-03/018807 | 3/2003 |

OTHER PUBLICATIONS

News Briefing, Nature (1999) 402:715-720.
Office Action for Japanese Application No. 2005-373127, mailed on Nov. 30, 2007, 9 pages.
Burgess et al., Teh Journal of Cell Biology (1990) 111:2129-2138.
Gao et al., The Prostate (1997) 31:264-281.
GenBank Accession No. AA515600, Aug. 19, 1997.
GenBank Accession No. AA662072, Dec. 3, 1997.
GenBank Accession No. AA906699, Jun. 9, 1998.
GenBank Accession No. AA908234, Jun. 9, 1998.
GenBank Accession No. AI038272, Jun. 30, 1998.
GenBank Accession No. AI186263, Oct. 28, 1998.
GenBank Accession No. AI089141, Nov. 10, 1998.
GenBank Accession No. AI338175, Feb. 13, 1999.
GenBank Accession No. AW183920, Nov. 18, 1999.
Greenspan et al., Nature Biotechnology (1999) 17:936-937.
Hillier et al., Apr. 5, 1995, GenBank Accession No. R09761.
Hillier et al., May 16, 1997, GenBank Accession No. AA402000.
Hillier et al., May 16, 1997, GenBank Accession No. AA402132.
Hillier et al., Jun. 5, 1995, GenBank Accession No. R74043.
Hillier et al., Jun. 5, 1995, GenBank Accession No. R74138.
Hillier et al., Jul. 31, 1995, GenBank Accession No. H43317.
Hillier et al., Dec. 24, 1997, GenBank Accession No. AA705037.
Fujiwara et al., Oct. 2, 1996, GenBank Accession No. C18563.
Lazar et al., Molecular and Cellular Biology (1988) 8:1247-1252.
Lin et al., Biochemistry (1975) 14:1559.
Rieger et al., Glossary of Genetics and Cytogenetics (1976) 17-18.
Schwartz et al., Proc. Natl. Acad. Sci. (1987) 84:6408-6411.
Tockman et al., Cancer Res (1992) 52:2711-2718.
Zhu et al., Genomics (2002) 80:144-150.

* cited by examiner

FIG. 1A

```
               10          19          28          37          46          55
5' TGG CTG CGG TCG CCT GGG AGC TGC CGC CAG GGC CAG GAG GGG AGC GGC ACC TGG
   --- --- --- --- --- --- --- --- --- --- --- --- --- --- --- --- --- ---
    W   L   R   S   P   G   S   C   R   Q   G   Q   E   G   S   G   T   W 64          73          82          91         100         109
   AAG ATG CGC CCA TTG GCT GGT GGC CTG CTC AAG GTG GTG TTC GTG GTC TTC GCC
   --- --- --- --- --- --- --- --- --- --- --- --- --- --- --- --- --- ---
    K   M   R   P   L   A   G   G   L   L   K   V   V   F   V   V   F   A 118         127         136         145         154         163
   TCC TTG TGT GCC TGG TAT TCG GGG TAC CTG CTC GCA GAG CTC ATT CCA GAT GCA
   --- --- --- --- --- --- --- --- --- --- --- --- --- --- --- --- --- ---
    S   L   C   A   W   Y   S   G   Y   L   L   A   E   L   I   P   D   A 172         181         190         199         208         217
   CCC CTG TCC AGT GCT GCC TAT AGC ATC CGC AGC ATC GGG GAG AGG CCT GTC CTC
   --- --- --- --- --- --- --- --- --- --- --- --- --- --- --- --- --- ---
    P   L   S   S   A   A   Y   S   I   R   S   I   G   E   R   P   V   L 226         235         244         253         262         271
   AAA GCT CCA GTC CCC AAA AGG CAA AAA TGT GAC CAC TGG ACT CCC TGC CCA TCT
   --- --- --- --- --- --- --- --- --- --- --- --- --- --- --- --- --- ---
    K   A   P   V   P   K   R   Q   K   C   D   H   W   T   P   C   P   S 280         289         298         307         316         325
   GAC ACC TAT GCC TAC AGG TTA CTC AGC GGA GGT GGC AGA AGC AAG TAC GCC AAA
   --- --- --- --- --- --- --- --- --- --- --- --- --- --- --- --- --- ---
    D   T   Y   A   Y   R   L   L   S   G   G   G   R   S   K   Y   A   K 334         343         352         361         370         379
   ATC TGC TTT GAG GAT AAC CTA CTT ATG GGA GAA CAG CTG GGA AAT GTT GCC AGA
   --- --- --- --- --- --- --- --- --- --- --- --- --- --- --- --- --- ---
    I   C   F   E   D   N   L   L   M   G   E   Q   L   G   N   V   A   R 388         397         406         415         424         433
   GGA ATA AAC ATT GCC ATT GTC AAC TAT GTA ACT GGG AAT GTG ACA GCA ACA CGA
   --- --- --- --- --- --- --- --- --- --- --- --- --- --- --- --- --- ---
    G   I   N   I   A   I   V   N   Y   V   T   G   N   V   T   A   T   R 442         451         460         469         478         487
   TGT TTT GAT ATG TAT GAA GGC GAT AAC TCT GGA CCG ATG ACA AAG TTT ATT CAG
   --- --- --- --- --- --- --- --- --- --- --- --- --- --- --- --- --- ---
    C   F   D   M   Y   E   G   D   N   S   G   P   M   T   K   F   I   Q 496         505         514         523         532         541
   AGT GCT GCT CCA AAA TCC CTG CTC TTC ATG GTG ACC TAT GAC GAC GGA AGC ACA
   --- --- --- --- --- --- --- --- --- --- --- --- --- --- --- --- --- ---
    S   A   A   P   K   S   L   L   F   M   V   T   Y   D   D   G   S   T
```

FIG. 1B

```
         550           559           568           577           586           595
AGA CTG AAT AAC GAT GCC AAG AAT GCC ATA GAA GCA CTT GGA AGT AAA GAA ATC
--- --- --- --- --- --- --- --- --- --- --- --- --- --- --- --- --- ---
 R   L   N   N   D   A   K   N   A   I   E   A   L   G   S   K   E   I 604           613           622           631           640           649
AGG AAC ATG AAA TTC AGG TCT AGC TGG GTA TTT ATT GCA GCA AAA GGC TTG GAA
--- --- --- --- --- --- --- --- --- --- --- --- --- --- --- --- --- ---
 R   N   M   K   F   R   S   S   W   V   F   I   A   A   K   G   L   E 658           667           676           685           694           703
CTC CCT TCC GAA ATT CAG AGA GAA AAG ATC AAC CAC TCT GAT GCT AAG AAC AAC
--- --- --- --- --- --- --- --- --- --- --- --- --- --- --- --- --- ---
 L   P   S   E   I   Q   R   E   K   I   N   H   S   D   A   K   N   N 712           721           730           739           748           757
AGA TAT TCT GGC TGG CCT GCA GAG ATC CAG ATA GAA GGC TGC ATA CCC AAA GAA
--- --- --- --- --- --- --- --- --- --- --- --- --- --- --- --- --- ---
 R   Y   S   G   W   P   A   E   I   Q   I   E   G   C   I   P   K   E 766           775           784           793           802           811
CGA AGC TGA CAC TGC AGG GTC CTG AGT AAA TGT GTT CTG TAT AAA CAA ATG CAG
--- --- --- --- --- --- --- --- --- --- --- --- --- --- --- --- --- ---
 R   S   *

820           829           838           847           856           865
CTG GAA TCG CTC AAG AAT CTT ATT TTT CTA AAT CCA ACA GCC CAT ATT TGA TGA
--- --- --- --- --- --- --- --- --- --- --- --- --- --- --- --- --- ---
         874           883           892           901           910           919
GTA TTT TGG GTT TGT TGT AAA CCA ATG AAC ATT TGC TAG TTG TAA AAA AAA AAA
--- --- --- --- --- --- --- --- --- --- --- --- --- --- --- --- --- ---
         928
AAA AAA AAA AAA 3'
--- --- --- ---
```

FIG. 2A 38.0% identity in 184 residues overlap; Score: 342.0; Gap frequency: 1.6%

```
36P6D5      49
ERPVLKAPVPKRQKCDHWTPCPSDTYAYRLLSGGGRSKYAKICFEDNLLMGEQLGNVARG
2-19        45
ESSVTAAPRARKYKCGLPQPCPEEHLAFRVVSGAANVIGPKICLEDKMLMSSVKDNVGRG
             *  *  **      **     ***    *  *  **         *** **  **       **
**

36P6D5      109
INIAIVNYVTGNVTATRCFDMYEGDNSGPMTKFIQSAAPKSLLFMVTYDDGSTRLNNDAK
2-19        105 LNIALVNGVSGELIEARAFDMWAGD-
VNDLLKFIRPLHEGTLVFVASYDDPATKMNEETR
             *** **  *  *     * ***   **           ***           *  *    ***    *  *

36P6D5      169
NAIEALGSKEIRNMKFRSSWVFIAAKGLELPSEIQREKINHSDAKNNRYSGWPAEIQIEG
2-19        164 KLFSELGSRNAKELAFRDSWVFVGAKGVQNKSPFEQHVKNSKHS--
NKYEGCPEALEMEG
             ***          ** **** ***   *       *        * * * *
**

36P6D5      229 CIPK
2-19        222 CIPR
                ***
```

FIG. 2B 40.7% identity in 177 residues overlap; Score: 361.0; Gap frequency: 1.7%

```
36P6D5      58
PKRQKCDHWTPCPSDTYAYRLLSGGGRSKYAKICFEDNLLMGEQLGNVARGINIAIVNYV
GS3786      53
PPRYKCGISKACPEKHFAFKMASGAANVVGPKICLEDNVLMSGVKNNVGRGINVALANGK
            *  *  **         **    *          **     *** ***  **      ** **** *  *

36P6D5      118
TGNVTATRCFDMYEGDNSGPMTKFIQSAAPKSLLFMVTYDDGSTRLNNDAKNAIEALGSK
GS3786      113 TGEVLDTKYFDMWGGD-
VAPFIEFLKAIQDGTIVLMGTYDDGATKLNDEARRLIADLGST
             ** *   *   ***  **     *     *              * *****  *  **    *     *    ***

36P6D5      178 EIRNMKFRSSWVFIAAKGLELPSEIQREKINHSDAKNNRYSGWPAEIQIEGCIPKER
GS3786      172 SITNLGFRDNWVFCGGKGIKTKSPFEQHIKNNKD--TNKYEGWPEVVEMEGCIPQKQ
                 *  *   ** ***    **      *         *      *   * * ***        *****
```

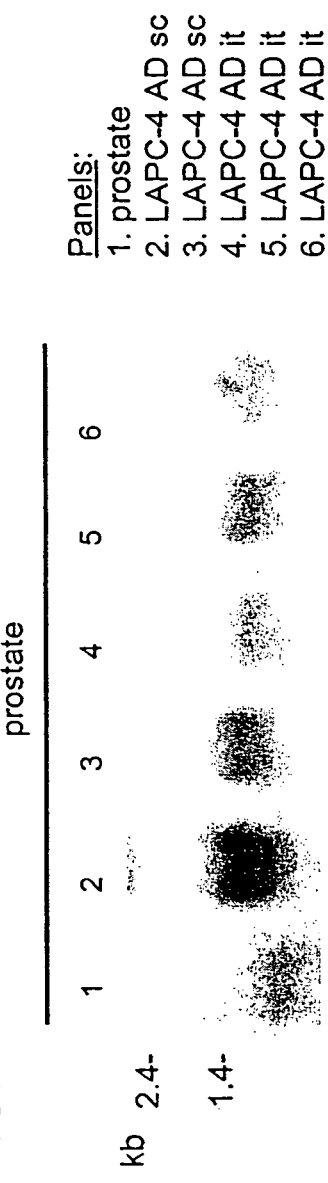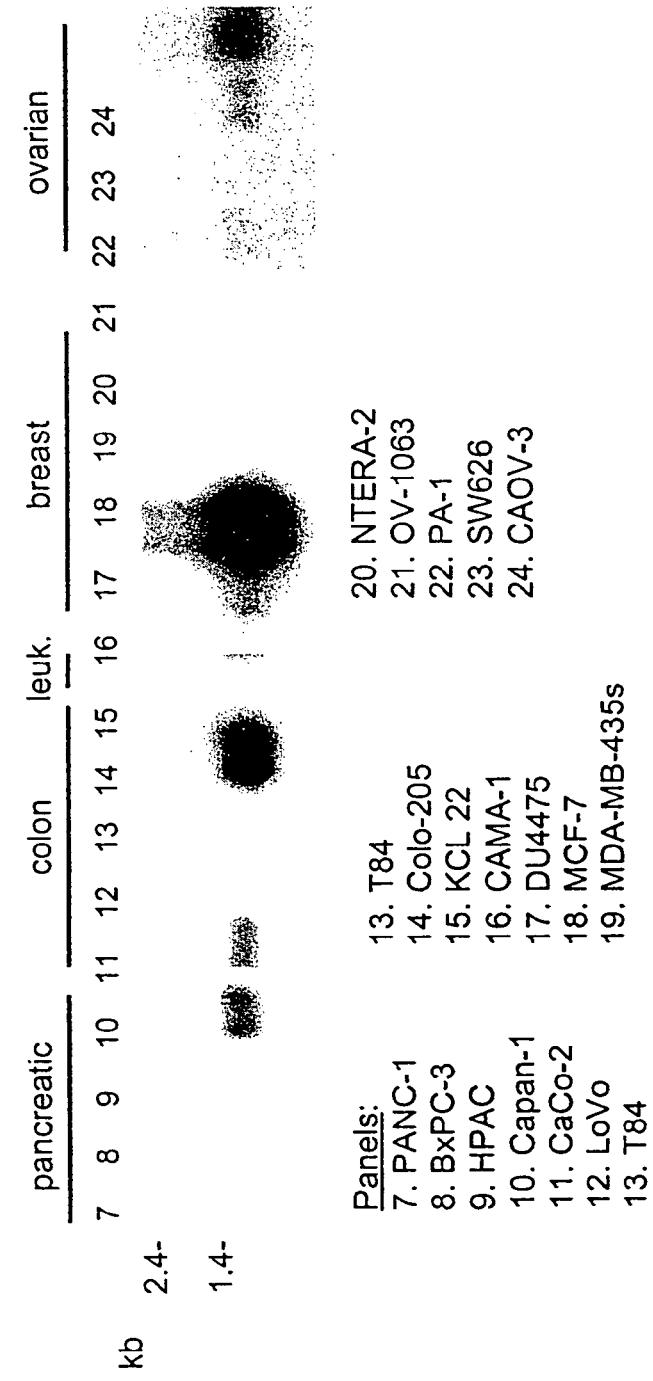
FIG. 4A
FIG. 4B

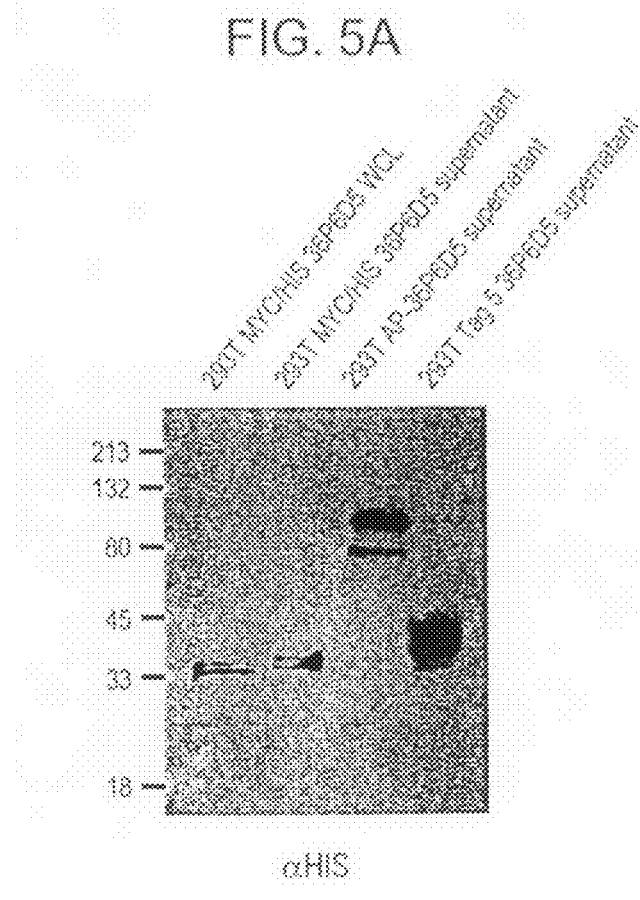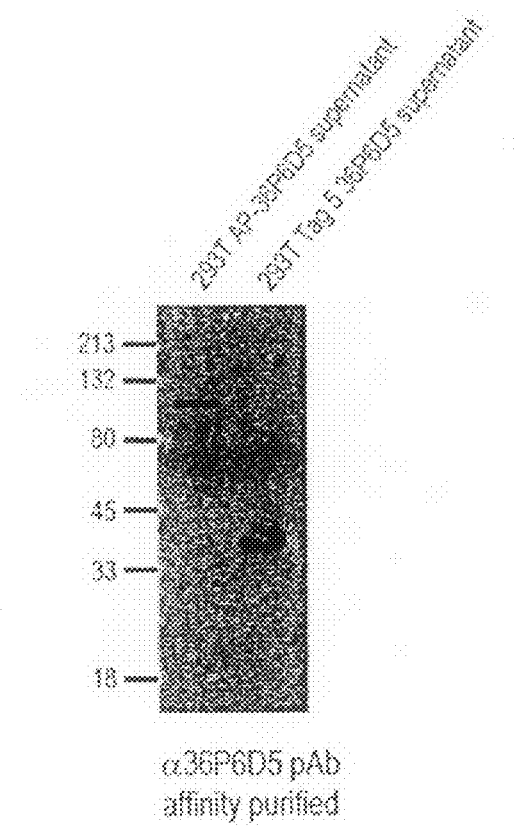

- Bladder cancer patient pool (3 patients)
- Kidney cancer patient pool (3 patients)
- Colon cancer patient pool (2 patients)
- Lung cancer patient
- Water blank Panel:
1. Normal Bladder
2. Patient 1, normal adjacent tissue
3. Patient 1, tumor
4. Patient 2, normal adjacent tissue
5. Patient 2, tumor
6. Patient 3, normal adjacent tissue
7. Patient 3, tumor
8. Patient 4, tumor N: normal adjacent tissue
Ca: cancer tissue

36P6D5: SECRETED TUMOR ANTIGEN

The present application is a divisional application of U.S. patent application Ser. No. 10/365,254, filed Feb. 11, 2003, now U.S. Pat. No. 7,223,542, which is a divisional of U.S. patent application Ser. No. 09/702,114, filed on Oct. 30, 2000, now U.S. Pat. No. 6,566,078, which claims the benefit of priority of U.S. Provisional Application No. 60/162,417 filed Oct. 28, 1999. The contents of the above patent applications are incorporated by reference herein in their entirety.

FIELD OF THE INVENTION

The invention described herein relates to a gene and its encoded tumor antigen, termed 36P6D5, and to diagnostic and therapeutic methods and compositions useful in the management of various cancers that express 36P6D5 gene products.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
|---|---|---|
| 511582002211seqlist.txt | Sep. 18, 2007 | 10,016 bytes |

BACKGROUND OF THE INVENTION

Cancer is the second leading cause of human death next to coronary disease. Worldwide, millions of people die from cancer every year. In the United States alone, cancer causes the death of well over a half-million people each year, with some 1.4 million new cases diagnosed per year. While deaths from heart disease have been declining significantly, those resulting from cancer generally are on the rise. In the early part of the next century, cancer is predicted to become the leading cause of death.

Worldwide, several cancers stand out as the leading killers. In particular, carcinomas of the lung, prostate, breast, colon, pancreas, and ovary represent the primary causes of cancer death. These and virtually all other carcinomas share a common lethal feature. With very few exceptions, metastatic disease from a carcinoma is fatal. Moreover, even for those cancer patients who initially survive their primary cancers, common experience has shown that their lives are dramatically altered. Many cancer patients experience strong anxieties driven by the awareness of the potential for recurrence or treatment failure. Many cancer patients experience physical debilitations following treatment. Many cancer patients experience a recurrence.

Generally speaking, the fundamental problem in the management of the deadliest cancers is the lack of effective and non-toxic systemic therapies. Molecular medicine, still very much in its infancy, promises to redefine the ways in which these cancers are managed. Unquestionably, there is an intensive worldwide effort aimed at the development of novel molecular approaches to cancer diagnosis and treatment. For example, there is a great interest in identifying truly tumor-specific genes and proteins that could be used as diagnostic and prognostic markers and/or therapeutic targets or agents. Research efforts in these areas are encouraging, and the increasing availability of useful molecular technologies has accelerated the acquisition of meaningful knowledge about cancer. Nevertheless, progress is slow and generally uneven.

As discussed below, the management of prostate cancer serves as a good example of the limited extent to which molecular biology has translated into real progress in the clinic. With limited exceptions, the situation is more or less the same for the other major carcinomas mentioned above.

Worldwide, prostate cancer is the fourth most prevalent cancer in men. In North America and Northern Europe, it is by far the most common male cancer and is the second leading cause of cancer death in men. In the United States alone, well over 40,000 men die annually of this disease—second only to lung cancer. Despite the magnitude of these figures, there is still no effective treatment for metastatic prostate cancer. Surgical prostatectomy, radiation therapy, hormone ablation therapy, and chemotherapy remain fixed as the main treatment modalities. Unfortunately, these treatments are ineffective for many and are often associated with significant undesirable consequences.

On the diagnostic front, the lack of a prostate tumor marker that can accurately detect early-stage, localized tumors remains a significant limitation in the management of this disease. Although the serum PSA assay has been a very useful tool, its specificity and general utility is widely regarded as lacking in several important respects, as further discussed below. Most prostate cancers initially occur in the peripheral zone of the prostate gland, away from the urethra. Tumors within this zone may not produce any symptoms and, as a result, most men with early-stage prostate cancer will not present clinical symptoms of the disease until significant progression has occurred. Tumor progression into the transition zone of the prostate may lead to urethral obstruction, thus producing the first symptoms of the disease. However, these clinical symptoms are indistinguishable from the common non-malignant condition of benign prostatic hyperplasia (BPH). Early detection and diagnosis of prostate cancer currently relies on digital rectal examinations (DRE), prostate specific antigen (PSA) measurements, transrectal ultrasonography (TRUS), and transrectal needle biopsy (TRNB). At present, serum PSA measurement in combination with DRE represent the leading tool used to detect and diagnose prostate cancer. Both have major limitations which have fueled intensive research into finding better diagnostic markers of this disease.

Similarly, there is no available marker that can predict the emergence of the typically fatal metastatic stage of prostate cancer. Diagnosis of metastatic stage is presently achieved by open surgical or laparoscopic pelvic lymphadenectomy, whole body radionuclide scans, skeletal radiography, and/or bone lesion biopsy analysis. Clearly, better imaging and other less invasive diagnostic methods offer the promise of easing the difficulty those procedures place on a patient, as well as improving diagnostic accuracy and opening therapeutic options. A similar problem is the lack of an effective prognostic marker for determining which cancers are indolent and which ones are or will be aggressive. PSA, for example, fails to discriminate accurately between indolent and aggressive cancers. Until there are prostate tumor markers capable of reliably identifying early-stage disease, predicting susceptibility to metastasis, and precisely imaging tumors, the management of prostate cancer will continue to be extremely difficult.

PSA is the most widely used tumor marker for screening, diagnosis, and monitoring prostate cancer today. In particular, several immunoassays for the detection of serum PSA are in widespread clinical use. Recently, a reverse transcriptase-polymerase chain reaction (RT-PCR) assay for PSA mRNA in serum has been developed. However, PSA is not a disease-specific marker, as elevated levels of PSA are detectable in a large percentage of patients with BPH and prostatitis (25-86%) (Gao et al., 1997, Prostate 31: 264-281), as well as in other nonmalignant disorders and in some normal men, a factor which significantly limits the diagnostic specificity of this marker. For example, elevations in serum PSA of between 4 to 10 ng/ml are observed in BPH, and even higher values are observed in prostatitis, particularly acute prostatitis. BPH is an extremely common condition in men. Further confusing the situation is the fact that serum PSA elevations may be observed without any indication of disease from DRE, and visa-versa. Moreover, it is now recognized that PSA is not prostate-specific (Gao et al., supra, for review).

Various methods designed to improve the specificity of PSA-based detection have been described, such as measuring PSA density and the ratio of free vs. complexed PSA. However, none of these methodologies have been able to reproducibly distinguish benign from malignant prostate disease. In addition, PSA diagnostics have sensitivities of between 57-79% (Cupp & Osterling, 1993, Mayo Clin Proc 68:297-306), and thus miss identifying prostate cancer in a significant population of men with the disease.

There are some known markers which are expressed predominantly in prostate, such as prostate specific membrane antigen (PSM), a hydrolase with 85% identity to a rat neuropeptidase (Carter et al., 1996, Proc. Natl. Acad. Sci. USA 93: 749; Bzdega et al., 1997, J. Neurochem. 69: 2270). However, the expression of PSM in small intestine and brain (Israeli et al., 1994, Cancer Res. 54: 1807), as well its potential role in neuropeptide catabolism in brain, raises concern of potential neurotoxicity with anti-PSM therapies. Preliminary results using an Indium-111 labeled, anti-PSM monoclonal antibody to image recurrent prostate cancer show some promise (Sodee et al., 1996, Clin Nuc Med 21: 759-766). More recently identified prostate cancer markers include PCTA-1 (Su et al., 1996, Proc. Natl. Acad. Sci. USA 93: 7252) and prostate stem cell antigen (PSCA) (Reiter et al., 1998, Proc. Natl. Acad. Sci. USA 95: 1735). PCTA-1, a novel galectin, is largely secreted into the media of expressing cells and may hold promise as a diagnostic serum marker for prostate cancer (Su et al., 1996). PSCA, a GPI-linked cell surface molecule, was cloned from LAPC-4 cDNA and is unique in that it is expressed primarily in basal cells of normal prostate tissue and in cancer epithelia (Reiter et al., 1998). Vaccines for prostate cancer are also being actively explored with a variety of antigens, including PSM and PSA.

While previously identified markers such as PSA, PSM, PCTA and PSCA have facilitated efforts to diagnose and treat prostate cancer, there is need for the identification of additional markers and therapeutic targets for prostate and related cancers in order to further improve diagnosis and therapy.

SUMMARY OF THE INVENTION

The present invention relates to a gene and protein designated 36P6D5. In normal individuals, 36P6D5 protein appears to be predominantly expressed in pancreas, with lower levels of expression detected in prostate and small intestine. The 36P6D5 gene is also expressed in several human cancer xenografts and cell lines derived from prostate, breast, ovarian and colon cancers, in some cases at high levels. Over-expression of 36P6D5, relative to normal, is observed in prostate cancer xenografts initially derived from a prostate cancer lymph node metastasis and passaged intratibially and subcutaneously in SCID mice. Extremely high level expression of 36P6D5 is detected in the breast cancer cell line DU4475, a cell line that was initially derived from a mammary gland carcinoma (Langlois et al., 1979, Cancer Res. 39: 2604). The 36P6D5 gene is also expressed in tumor patient samples derived from bladder, kidney, colon and lung cancers, in some cases at high levels.

A full length 36P6D5 cDNA of 931 bp (SEQ ID NO: 1) provided herein encodes a 235 amino acid open reading frame (SEQ ID NO: 2) with significant homology to the 2-19 protein precursor (Genbank P98173) as well as a gene previously cloned from human osteoblasts (Q92520). The predicted 235 amino acid 36P6D5 protein also contains an N-terminal signal sequence, indicating that the 36P6D5 protein is secreted. The 36P6D5 gene therefore encodes a secreted tumor antigen which may be useful as a diagnostic, staging and/or prognostic market for, and/or may serve as a target for various approaches to the treatment of, prostate, breast, colon, pancreatic, and ovarian cancers expressing 36P6D5. The predicted molecular weight of the 36P6D5 protein is approximately 26 kD and its' pI is 8.97.

Expression analysis demonstrates high levels of 36P6D5 expression in several prostate and other cancer cell lines as well as prostate cancer patient samples and tumor xenografts. The expression profile of 36P6D5 in normal adult tissues, combined with the over-expression observed in cancer cells such as bladder, colon, kidney, breast, lung, ovary and prostate cancer cell lines and/or cancer patient samples, provides evidence that 36P6D5 is aberrantly expressed in at least some cancers, and can serve as a useful diagnostic and/or therapeutic target for such cancers.

The invention provides polynucleotides corresponding or complementary to all or part of the 36P6D5 genes, mRNAs, and/or coding sequences, preferably in isolated form, including polynucleotides encoding 36P6D5 proteins and fragments thereof, DNA, RNA, DNA/RNA hybrid, and related molecules, polynucleotides or oligonucleotides complementary to the 36P6D5 genes or mRNA sequences or parts thereof, and polynucleotides or oligonucleotides that hybridize to the 36P6D5 genes, mRNAs, or to 36P6D5-encoding polynucleotides. Also provided are means for isolating cDNAs and the genes encoding 36P6D5. Recombinant DNA molecules containing 36P6D5 polynucleotides, cells transformed or transduced with such molecules, and host-vector systems for the expression of 36P6D5 gene products are also provided. The invention further provides 36P6D5 proteins and polypeptide fragments thereof. The invention further provides antibodies that bind to 36P6D5 proteins and polypeptide fragments thereof, including polyclonal and monoclonal antibodies, murine and other mammalian antibodies, chimeric antibodies, humanized and fully human antibodies, and antibodies labeled with a detectable marker.

The invention further provides methods for detecting the presence and status of 36P6D5 polynucleotides and proteins in various biological samples, as well as methods for identifying cells that express 36P6D5. A typical embodiment of this invention provides methods for monitoring 36P6D5 gene products in a tissue sample having or suspected of having some form of growth dysregulation such as cancer.

The invention further provides various therapeutic compositions and strategies for treating cancers that express 36P6D5 such as prostate cancers, including therapies aimed at inhibiting the transcription, translation, processing or function of 36P6D5 as well as cancer vaccines.

BRIEF DESCRIPTION OF THE FIGURES

FIGS. 1A-1B. Nucleotide (SEQ ID NO: 1) and deduced amino acid (SEQ ID NO: 2) sequences of 36P6D5 cDNA. The start methionine and consensus Kozak sequence are indicated in bold and the putative N-terminal signal sequence is underlined.

FIGS. 2A-2B. Amino acid sequence alignment of the 36P6D5 ORF with 2-19 protein precursor (2A) (SEQ ID NO: 15) and GS3786 protein (osteoblast protein) (2B) (SEQ ID NO: 16). Percent sequence identities are indicated on the figure.

FIGS. 4A-4B. Northern blot analysis of human 36P6D5 mRNA expression in a panel of prostate cancer xenografts and various other human cancer cell lines.

FIGS. 5A-5B. Secretion of 36P6D5 protein from transfected 293T cells and detection with anti-36P6D5 polyclonal antibody. 293T cells were transiently transfected with either pCDNA 3.1 MYC/HIS 36P6D5, pTag5 36P6D5, in which the natural signal sequence of 36P6D5 is replaced with an immunoglobulin signal sequence, or pAPTag5 36P6D5 which encodes a fusion protein composed of 36P6D5 and alkaline phosphatase (also containing the Ig signal sequence). Conditioned media or whole cell lysates were subjected to Western blotting with either rabbit anti-His pAb (Santa Cruz, Biotechnology, Inc., 1:2,500 dilution, left panel) or with affinity purified rabbit anti-36P6D5 pAb (1 ug/ml, right panel). Anti-His and anti-36P6D5 pAb reactive bands were visualized by incubation of the blots with anti-rabbit-HRP conjugated secondary antibody followed by enhanced chemiluminescence detection.

DETAILED DESCRIPTION OF THE INVENTION

Figure 3:
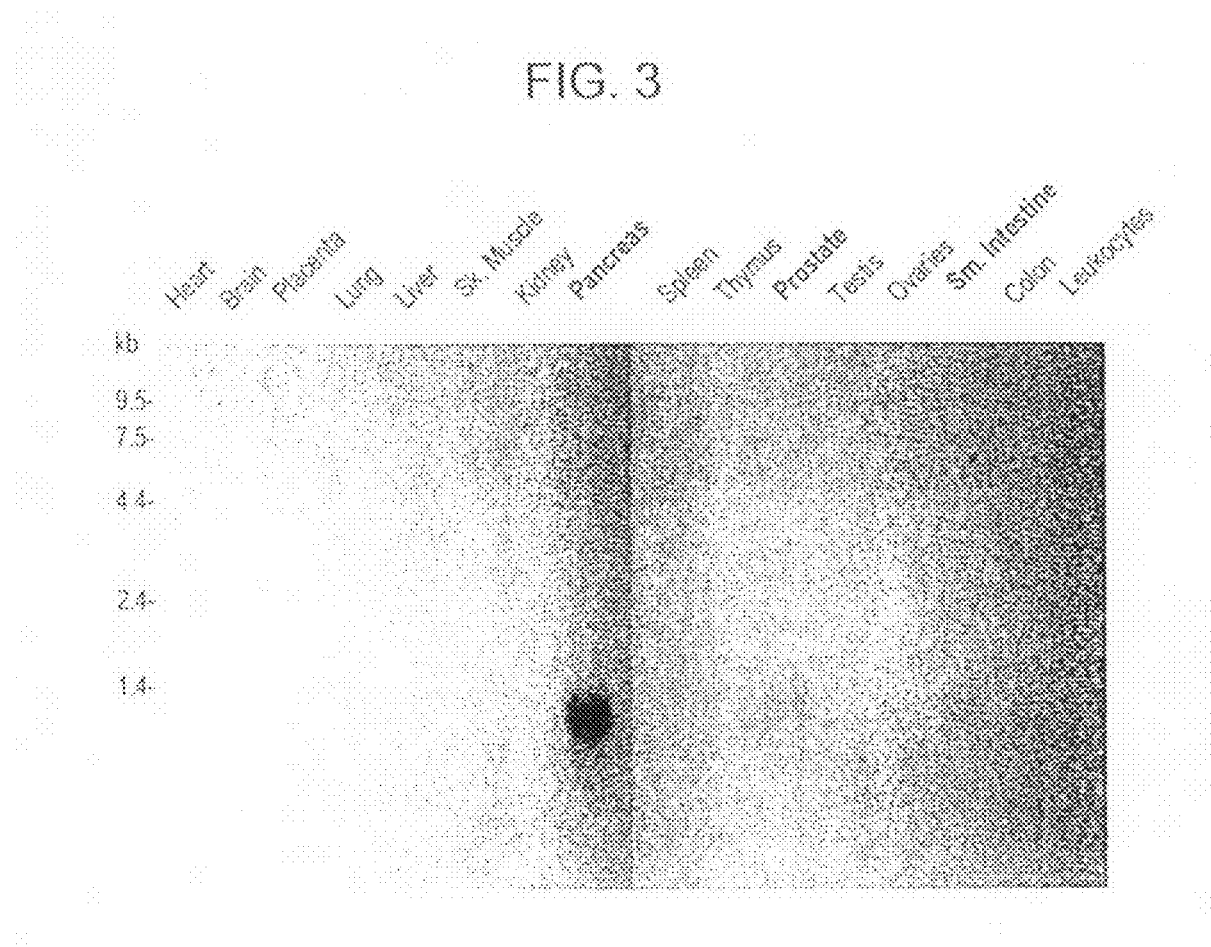
FIG. 3. Northern blot analysis of human 36P6D5 expression in various normal tissues showing predominant expression in pancreas and low level expression in prostate and small intestine.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

As used herein, the terms "advanced prostate cancer", "locally advanced prostate cancer", "advanced disease" and "locally advanced disease" mean prostate cancers which have extended through the prostate capsule, and are meant to include stage C disease under the American Urological Association (AUA) system, stage C1-C2 disease under the Whitmore-Jewett system, and stage T3-T4 and N+ disease under the TNM (tumor, node, metastasis) system. In general, surgery is not recommended for patients with locally advanced disease, and these patients have substantially less favorable outcomes compared to patients having clinically localized (organ-confined) prostate cancer. Locally advanced disease is clinically identified by palpable evidence of induration beyond the lateral border of the prostate, or asymmetry or induration above the prostate base. Locally advanced prostate cancer is presently diagnosed pathologically following radical prostatectomy if the tumor invades or penetrates the prostatic capsule, extends into the surgical margin, or invades the seminal vesicles.

As used herein, the terms "metastatic prostate cancer" and "metastatic disease" mean prostate cancers which have spread to regional lymph nodes or to distant sites, and are meant to include stage D disease under the AUA system and stage TxNxM+ under the TNM system. As is the case with locally advanced prostate cancer, surgery is generally not indicated for patients with metastatic disease, and hormonal (androgen ablation) therapy is the preferred treatment modality. Patients with metastatic prostate cancer eventually develop an androgen-refractory state within 12 to 18 months of treatment initiation, and approximately half of these patients die within 6 months thereafter. The most common site for prostate cancer metastasis is bone. Prostate cancer bone metastases are, on balance, characteristically osteoblastic rather than osteolytic (i.e., resulting in net bone formation). Bone metastases are found most frequently in the spine, followed by the femur, pelvis, rib cage, skull and humerus. Other common sites for metastasis include lymph nodes, lung, liver and brain. Metastatic prostate cancer is typically diagnosed by open or laparoscopic pelvic lymphadenectomy, whole body radionuclide scans, skeletal radiography, and/or bone lesion biopsy.

As used herein, the term "polynucleotide" means a polymeric form of nucleotides of at least about 10 bases or base pairs in length, either ribonucleotides or deoxynucleotides or a modified form of either type of nucleotide, and is meant to include single and double stranded forms of DNA.

As used herein, the term "polypeptide" means a polymer of at least about 6 amino acids. Throughout the specification, standard three letter or single letter designations for amino acids are used.

As used herein, the terms "hybridize", "hybridizing", "hybridizes" and the like, used in the context of polynucleotides, are meant to refer to conventional hybridization conditions, preferably such as hybridization in 50% formamide/6xSSC/0.1% SDS/100 µg/ml ssDNA, in which temperatures for hybridization are above 37 degrees C. and temperatures for washing in 0.1xSSC/0.1% SDS are above 55 degrees C., and most preferably to stringent hybridization conditions.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5xSSC (0.75 M NaCl, 0.075 M sodium citrate), 50 mM sodium phosphate (pH 6.8), 0.1% sodium pyrophosphate, 5xDenhardt's solution, sonicated salmon sperm DNA (50 µg/ml), 0.1% SDS, and 10% dextran sulfate at 42° C., with washes at 42° C. in 0.2xSSC (sodium chloride/sodium citrate) and 50% formamide at 55° C., followed by a high-stringency wash consisting of 0.1xSSC containing EDTA at 55° C.

"Moderately stringent conditions" may be identified as described by Sambrook et al., 1989, Molecular Cloning: A Laboratory Manual, New York: Cold Spring Harbor Press, and include the use of washing solution and hybridization conditions (e.g., temperature, ionic strength and % SDS) less stringent than those described above. An example of moderately stringent conditions is overnight incubation at 37° C. in a solution comprising: 20% formamide, 5xSSC (150 mM NaCl, 15 mM trisodium citrate), 50 mM sodium phosphate (pH 7.6), 5xDenhardt's solution, 10% dextran sulfate, and 20 mg/mL denatured sheared salmon sperm DNA, followed by washing the filters in 1xSSC at about 37-50° C. The skilled artisan will recognize how to adjust the temperature, ionic strength, etc. as necessary to accommodate factors such as probe length and the like.

In the context of amino acid sequence comparisons, the term "identity" is used to express the percentage of amino acid residues at the same relative positions that are the same. Also in this context, the term "homology" is used to express the percentage of amino acid residues at the same relative positions that are either identical or are similar, using the conserved amino acid criteria of BLAST analysis, as is generally understood in the art. For example, % identity values may be generated by WU-BLAST-2 (Altschul et al., 1996, Methods in Enzymology 266:460-480; http://blast.wustl/edu/blast/README.html). Further details regarding amino acid substitutions, which are considered conservative under such criteria, are provided below. Additional definitions are provided throughout the subsections that follow.

Molecular Biology of and Uses for 36P6D5

As is further described in the Examples below, the 36P6D5 gene and protein have been characterized using a number of analytical approaches. For example, analyses of nucleotide coding and amino acid sequences were conducted in order to identify potentially related molecules, as well as recognizable structural domains, topological features, and other elements within the 36P6D5 mRNA and protein structure. Northern blot analyses of 36P6D5 mRNA expression were conducted in order to establish the range of normal and cancerous tissues expressing 36P6D5 message.

Figure 6:
FIG. 6. Expression of 36P6D5 in cancer patient tumors. RT-PCR analysis of 36P6D5 mRNA expression in bladder cancer, kidney cancer, colon cancer, and lung cancer patient tumors.
Figure 7:
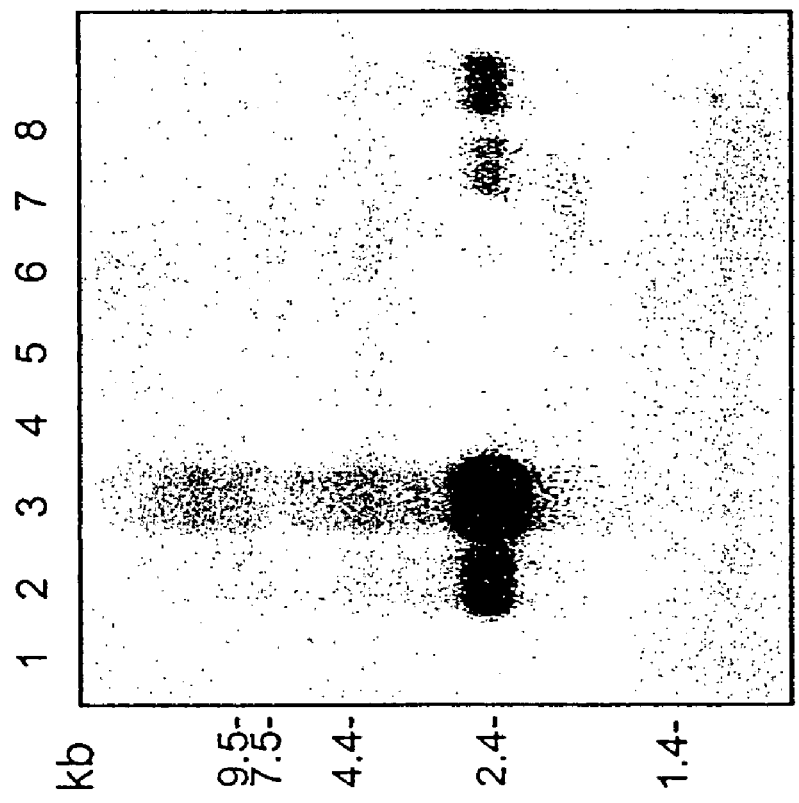
FIG. 7. 36P6D5 expression in bladder cancer and their matched normal tissues was tested by Northern blot analysis. For this figure, 10 μg of total RNA were loaded for each sample. Overexpression of 36P6D5 expression was detected in 3 out of 4 cancers tested lanes 3, 5, 7 and 8). No expression was seen in bladder tissue isolated from a normal individual lane 1).

The 36P6D5 protein is predicted to be initially translated into a 235 amino acid precursor containing a signal sequence which, during post-translational processing, is cleaved to yield a mature 211 or 212 amino acid secreted protein (FIG. 1). The 36P6D5 protein has a predicted molecular weight=25.9 and pI=8.97. 36P6D5 is predicted to be a membrane associated protein, with the first 28 amino acids being intracellular. Based on the Signal Peptide algorithm, the intracellular portion of the protein seems to be cleaved off between aa 29 and 30, releasing the rest of the molecule as a soluble protein. The 36P6D5 gene is normally expressed predominantly in pancreas (FIG. 3), but is also expressed or overexpressed in several human cancers, including cancers of the prostate, breast, pancreas, colon, lung, bladder, kidney and ovary (FIGS. 4, 6 and 7). The 36P6D5 protein structure shows significant homology to two previously described protein sequences, 2-19 protein precursor (Genbank P98173) (SEQ ID NO: 15) and an osteoblast protein designated GS3786 (Q92520) (SEQ ID NO: 16) (FIG. 2). 36P6D5 has similarities to a predicted osteoblast protein, NP-055703.1, with 36% identity over its entire sequence, with most of the 54% homology occurring between aa 74 and aa 235. It is also weakly similar to protein GS3786. The fact that 36P6D5 has similarities to bone derived proteins is not surprising as it was discovered using SSH comparing LAPC4AD(IT) and LAPC4AD(SQ) RNA. Given its homology to the osteoblast protein, it is possible that the 36P6D5 protein may function as a secreted factor that stimulates the proliferation of cancer cells (such as the 36P5D6 cancer cells shown in FIGS. 4, 6 and 7) in bone.

As disclosed herein, 36P6D5 exhibits specific properties that are analogous to those found in a family of genes whose polynucleotides, polypeptides and anti-polypeptide antibodies are used in well known diagnostic assays directed to examining conditions associated with dysregulated cell growth such as cancer, in particular prostate cancer (see e.g. both its highly specific pattern of tissue expression as well as its overexpression in prostate cancers as described for example in Example 3). The best known member of this class is PSA, the archetypal marker that has been used by medical practitioners for years to identify and monitor the presence of prostate cancer (see e.g. Merrill et al., J. Urol. 163(2): 503-5120 (2000); Polascik et al., J. Urol. August; 162(2):293-306 (1999) and Fortier et al., J. Nat. Cancer Inst. 91(19): 1635-1640(1999)). A variety of other diagnostic markers are also used in this context including p53 and K-ras (see e.g. Tulchinsky et al., Int J Mol Med 1999 July; 4(1):99-102 and Minimoto et al., Cancer Detect Prev 2000; 24(1):1-12). Consequently, this disclosure of the 36P6D5 polynucleotides and polypeptides (as well as the 36P6D5 polynucleotide probes and anti-36P6D5 antibodies used to identify the presence of these molecules) and their properties allows skilled artisans to utilize these molecules in methods that are analogous to those used, for example, in a variety of diagnostic assays directed to examining conditions associated with cancer.

Typical embodiments of diagnostic methods which utilize the 36P6D5 polynucleotides, polypeptides and antibodies described herein are analogous to those methods from well established diagnostic assays which employ PSA polynucleotides, polypeptides and antibodies. For example, just as PSA polynucleotides are used as probes (for example in Northern analysis, see e.g. Sharief et al., Biochem. Mol. Biol. Int. 33(3):567-74(1994)) and primers (for example in PCR analysis, see e.g. Okegawa et al., J. Urol. 163(4): 1189-1190 (2000)) to observe the presence and/or the level of PSA mRNAs in methods of monitoring PSA overexpression or the metastasis of prostate cancers, the 36P6D5 polynucleotides described herein can be utilized in the same way to detect 36P6D5 overexpression or the metastasis of prostate and other cancers expressing this gene. Alternatively, just as PSA polypeptides are used to generate antibodies specific for PSA which can then be used to observe the presence and/or the level of PSA proteins in methods of monitoring PSA protein overexpression (see e.g. Stephan et al., Urology 55(4):560-3 (2000)) or the metastasis of prostate cells (see e.g. Alanen et al., Pathol. Res. Pract. 192(3):233-7 (1996)), the 36P6D5 polypeptides described herein can be utilized to generate antibodies for use in detecting 36P6D5 overexpression or the metastasis of prostate cells and cells of other cancers expressing this gene. Specifically, because metastases involves the movement of cancer cells from an organ of origin (such as the bladder, kidney or prostate gland etc.) to a different area of the body (such as a lymph node), assays which examine a biological sample for the presence of cells expressing 36P6D5 polynucleotides and/or polypeptides can be used to provide evidence of metastasis, for example, when a biological sample from tissue that does not normally contain 36P6D5 expressing cells (lymph node) is found to contain 36P6D5 expressing cells. Alternatively 36P6D5 polynucleotides and/or polypeptides can be used to provide evidence of cancer, for example, when a cells in biological sample that do not normally express 36P6D5 or express 36P6D5 at a different level (such as kidney, bladder, lung and prostate cells etc.) are found to express 36P6D5 or have an increased expression of 36P6D5. In such assays, artisans may further wish to generate supplementary evidence of metastasis by testing the biological sample for the presence of a second tissue restricted marker (in addition to 36P6D5) such as PSA, PSCA etc. (see e.g. Alanen et al., Pathol. Res. Pract. 192(3): 233-237 (1996)).

Just as PSA polynucleotide fragments and polynucleotide variants are employed by skilled artisans for use in methods of monitoring this molecule, 36P6D5 polynucleotide fragments and polynucleotide variants can also be used in an analogous manner. In particular, typical PSA polynucleotides used in methods of monitoring this molecule are probes or primers which consist of fragments of the PSA cDNA sequence. Illustrating this, primers used to PCR amplify a PSA polynucleotide must include less than the whole PSA sequence to function in the polymerase chain reaction. In the context of such PCR reactions, skilled artisans generally create a variety of different polynucleotide fragments that can be used as primers in order to amplify different portions of a polynucleotide of interest or to optimize amplification reactions (see e.g. Caetano-Anolles, G. Biotechniques 25(3): 472-476, 478-480 (1998); Robertson et al., Methods Mol. Biol. 98:121-154 (1998)). An additional illustration of the utility of such fragments is provided in Example 3, where a 36P6D5 polynucleotide fragment is used as a probe to show the overexpression of 36P6D5 mRNAs in cancer cells. In addition, in order to facilitate their use by medical practitioners, variant polynucleotide sequences are typically used as primers and probes for the corresponding mRNAs in PCR and Northern analyses (see e.g. Sawai et al., Fetal Diagn. Ther. 1996 November-December; 11(6):407-13 and Current Protocols In Molecular Biology, Volume 2, Unit 2, Frederick M. Ausubul et al. eds., 1995)). Polynucleotide fragments and variants are typically useful in this context as long as they have the common attribute or characteristic of being capable of binding to a target polynucleotide sequence (e.g. the 36P6D5 polynucleotide shown in SEQ ID NO: 1) under conditions of relatively high stringency.

Just as PSA polypeptide fragments and polypeptide variants are employed by skilled artisans for use in methods of monitoring this molecule, 36P6D5 polypeptide fragments and polypeptide variants can also be used in an analogous manner. In particular, typical PSA polypeptides used in methods of monitoring this molecule are fragments of the PSA protein which contain an epitope that can be recognized by an antibody which will specifically bind to the PSA protein. This practice of using polypeptide fragments or polypeptide variants used to generate antibodies (such as anti-PSA antibodies) is typical in the art with a wide variety of systems such as fusion proteins being used by practitioners (see e.g. Current Protocols In Molecular Biology, Volume 2, Unit 16, Frederick M. Ausubul et al. eds., 1995). In this context, each of the variety of epitopes in a protein of interest functions to provide the architecture upon which the antibody is generated. Typically, skilled artisans generally create a variety of different polypeptide fragments that can be used in order to generate antibodies specific for different portions of a polypeptide of interest (see e.g. U.S. Pat. No. 5,840,501 and U.S. Pat. No. 5,939,533). For example it may be preferable to utilize a polypeptide comprising one of the 36P6D5 biological motifs discussed below. Polypeptide fragments and variants are typically useful in this context as long as they have the common attribute or characteristic of having an epitope capable of generating an antibody specific for a target polypeptide sequence (e.g. the 36P6D5 polypeptide shown in SEQ ID NO: 2).

As shown herein, the 36P6D5 polynucleotides and polypeptides (as well as the 36P6D5 polynucleotide probes and anti-36P6D5 antibodies used to identify the presence of these molecules) exhibit specific properties that make them useful in diagnosing cancers of the prostate. The described diagnostic assays that measures the presence of 36P6D5 gene products, in order to evaluate the presence or onset of the particular disease conditions described herein such as prostate cancer are particularly useful in identifying potential candidates for preventive measures or further monitoring, as has been done so successfully with PSA. Moreover, these materials satisfy a need in the art for molecules having similar characteristics to PSA in situations where, for example, a definite diagnosis of metastasis of prostatic origin cannot be made on the basis of a testing for PSA alone (see e.g. Alanen et al., Pathol. Res. Pract. 192(3): 233-237 (1996)), and consequently, materials such as 36P6D5 polynucleotides and polypeptides (as well as the 36P6D5 polynucleotide probes and anti-36P6D5 antibodies used to identify the presence of these molecules) must be employed to confirm metastases of prostatic origin.

Finally, in addition to their use in diagnostic assays, the 36P6D5 polynucleotides disclosed herein have a number of other specific utilities such as their use in the identification of oncogenetic associated chromosomal abnormalities in 21q22.2-22.3. Moreover, in addition to their use in diagnostic assays, the 36P6D5 polypeptides and polynucleotides disclosed herein have other utilities such as their use in the forensic analysis of tissues of unknown origin (see e.g. Takahama K Forensic Sci Int 1996 Jun. 28; 80(1-2): 63-9).

As discussed in detail below, 36P6D5 function can be assessed in mammalian cells using a variety of techniques that are well known in the art. For mammalian expression, 36P6D5 can be cloned into several vectors, including pcDNA 3.1 myc-His-tag (Invitrogen) and the retroviral vector pSRα-kneo (Muller et al., 1991, MCB 11:1785). Using these expression vectors, 36P6D5 can be expressed in several cell lines, including PC-3, NIH 3T3, LNCaP and 293T. Expression of 36P6D5 can be monitored using northern blot analysis. The mammalian cell lines expressing 36P6D5 can be tested in several in vitro and in vivo assays, including cell proliferation in tissue culture, activation of apoptotic signals, tumor formation in SCID mice, and in vitro invasion using a membrane invasion culture system (MICS) (Welch et al., Int. J. Cancer 43: 449-457). The 36P6D5 cell phenotype can be compared to the phenotype of cells that lack expression of 36P6D5.

36P6D5 Polynucleotides

One aspect of the invention provides polynucleotides corresponding or complementary to all or part of a 36P6D5 gene, mRNA, and/or coding sequence, preferably in isolated form, including polynucleotides encoding a 36P6D5 protein and fragments thereof, DNA, RNA, DNA/RNA hybrid, and related molecules, polynucleotides or oligonucleotides complementary to a 36P6D5 gene or mRNA sequence or a part thereof, and polynucleotides or oligonucleotides that hybridize to a 36P6D5 gene, mRNA, or to a 36P6D5 encoding polynucleotide (collectively, "36P6D5 polynucleotides"). As used herein, the 36P6D5 gene and protein is meant to include the 36P6D5 genes and proteins specifically described herein and the genes and proteins corresponding to other 36P6D5 proteins and structurally similar variants of the foregoing. Such other 36P6D5 proteins and variants will generally have coding sequences that are highly homologous to the 36P6D5 coding sequence, and preferably will share at least about 50% amino acid identity and at least about 60% amino acid homology (using BLAST criteria), more preferably sharing 70% or greater homology (using BLAST criteria).

A 36P6D5 polynucleotide may comprise a polynucleotide having the nucleotide sequence of human 36P6D5 as shown in FIG. 1 (SEQ ID NO: 1), wherein T can also be U; a polynucleotide which encodes all or part of the 36P6D5 protein; a sequence complementary to the foregoing; or a polynucleotide fragment of any of the foregoing. Another embodiment comprises a polynucleotide having the sequence as shown in FIG. 1 (SEQ ID NO: 1), from nucleotide residue number 59 through nucleotide residue number 763 or 766, wherein T can also be U. Another embodiment comprises a polynucleotide having the sequence as shown in FIG. 1 (SEQ ID NO: 1), from nucleotide residue number 131 through nucleotide residue number 763 or 766, wherein T can also be U. Another embodiment comprises a polynucleotide encoding a 36P6D5 polypeptide whose sequence is encoded by the cDNA contained in the plasmid as deposited on Apr. 9, 1999 with American Type Culture Collection, 10801 University Boulevard, Manassas, Va. 20110-2209, USA (ATCC) as Accession No. 207197. Another embodiment comprises a polynucleotide which is capable of hybridizing under stringent hybridization conditions to the human 36P6D5 cDNA shown in FIG. 1 (SEQ ID NO: 1).

Typical embodiments of the invention disclosed herein include 36P6D5 polynucleotides containing specific portions of the 36P6D5 mRNA sequence (and those which are complementary to such sequences) such as those that encode the protein and fragments thereof. For example, representative embodiments of the invention disclosed herein include: polynucleotides encoding about amino acid 1 to about amino acid 10 of the 36P6D5 protein shown in SEQ ID NO: 2, polynucleotides encoding about amino acid 20 to about amino acid 30 of the 36P6D5 protein shown in SEQ ID NO: 2, polynucleotides encoding about amino acid 30 to about amino acid 40 of the 36P6D5 protein shown in SEQ ID NO: 2, polynucleotides encoding about amino acid 40 to about amino acid 50 of the 36P6D5 protein shown in SEQ ID NO: 2, polynucleotides encoding about amino acid 50 to about amino acid 60 of the 36P6D5 protein shown in SEQ ID NO: 2, polynucleotides encoding about amino acid 60 to about amino acid 70 of the 36P6D5 protein shown in SEQ ID NO: 2, polynucleotides encoding about amino acid 70 to about amino acid 80 of the 36P6D5 protein shown in SEQ ID NO: 2, polynucleotides encoding about amino acid 80 to about amino acid 90 of the 36P6D5 protein shown in SEQ ID NO: 2 and polynucleotides encoding about amino acid 90 to about amino acid 100 of the 36P6D5 protein shown in SEQ ID NO: 2, etc. Following this scheme, polynucleotides encoding portions of the ammo acid sequence of amino acids 100-235 of the 36P6D5 protein are typical embodiments of the invention. Polynucleotides encoding larger portions of the 36P6D5 protein are also contemplated. For example polynucleotides encoding from about amino acid 1 (or 20 or 30 or 40 etc.) to about amino acid 20, (or 30, or 40 or 50 etc.) of the 36P6D5 protein shown in SEQ ID NO: 2 may be generated by a variety of techniques well known in the art.

Additional illustrative embodiments of 36P6D5 polynucleotides include embodiments consisting of a polynucleotide having the sequence as shown in FIG. 1 (SEQ ID NO: 1) from about nucleotide residue number 1 through about nucleotide residue number 250, from about nucleotide residue number 250 through about nucleotide residue number 500 and from about nucleotide residue number 500 through about nucleotide residue number 750 and from about nucleotide residue number 750 through about nucleotide residue number 913. These polynucleotide fragments can include any portion of the 36P6D5 sequence as shown in FIG. 1 (SEQ ID NO: 1), for example a polynucleotide having the 235 amino acid ORF within the polynucleotide sequence as shown in FIG. 1 (SEQ ID NO: 1), e.g. from about nucleotide residue number 59 through about nucleotide residue number 763.

Additional illustrative embodiments of the invention disclosed herein include 36P6D5 polynucleotide fragments encoding one or more of the biological motifs contained within the 36P6D5 protein sequence. Typical polynucleotide fragments of the invention include those that encode one or more of the 36P6D5 N-glycosylation sites, casein kinase II phosphorylation sites, the protein kinase c phosphorylation sites, the amino acid permeases signature or n-myristoylation sites as disclosed in greater detail in the text discussing the 36P6D5 protein and polypeptides below.

The polynucleotides of the preceding paragraphs have a number of different specific uses. For example, because the human 36P6D5 gene maps to chromosome 21q22.2-22.3, polynucleotides encoding different regions of the 36P6D5 protein can be used to characterize cytogenetic abnormalities on chromosome 21, bands q22.2-22.3 that have been identified as being associated with various cancers. In particular, a variety of chromosomal abnormalities in 21q22.2-22.3 have been identified as frequent cytogenetic abnormalities in a number of different cancers (see, e.g., Babu et al., Cancer Genet Cytogenet. 1989 March; 38(1):127-9 and Ho et al., Blood. 1996 Jun. 15; 87(12):5218-24). Consequently, polynucleotides encoding specific regions of the 36P6D5 protein provide new tools that can be used to delineate with a greater precision than previously possible, the specific nature of the cytogenetic abnormalities in this region of chromosome 21 that may contribute to the malignant phenotype. In this context, these polynucleotides satisfy a need in the art for expanding the sensitivity of chromosomal screening in order to identify more subtle and less common chromosomal abnormalities (see, e.g., Evans et al., 1994, Am. J. Obstet. Gynecol. 171(4):1055-1057).

Alternatively, as 36P6D5 is shown to be highly expressed in prostate cancers (see e.g. FIG. 4), these polynucleotides may be used in methods assessing the status of 36P6D5 gene products in normal versus cancerous tissues. Typically, polynucleotides encoding specific regions of the 36P6D5 protein may be used to assess the presence of perturbations (such as deletions, insertions, point mutations etc.) in specific regions (such as regions containing the RNA binding sequences) of the 36P6D5 gene products. Exemplary assays include both RT-PCR assays as well as single-strand conformation polymorphism (SSCP) analysis (see, e.g., Marrogi et al., 1999, J. Cutan. Pathol. 26(8): 369-378), both of which utilize polynucleotides encoding specific regions of a protein to examine these regions within the protein.

Other specifically contemplated embodiments of the invention disclosed herein are genomic DNA, cDNAs, ribozymes, and antisense molecules, as well as nucleic acid molecules based on an alternative backbone or including alternative bases, whether derived from natural sources or synthesized. For example, antisense molecules can be RNAs or other molecules, including peptide nucleic acids (PNAs) or non-nucleic acid molecules such as phosphorothioate derivatives, that specifically bind DNA or RNA in a base pair-dependent manner. A skilled artisan can readily obtain these classes of nucleic acid molecules using the 36P6D5 polynucleotides and polynucleotide sequences disclosed herein.

Antisense technology entails the administration of exogenous oligonucleotides that bind to a target polynucleotide located within the cells. The term "antisense" refers to the fact that such oligonucleotides are complementary to their intracellular targets, e.g., 36P6D5. See for example, Jack Cohen, 1988, OLIGODEOXYNUCLEOTIDES, Antisense Inhibitors of Gene Expression, CRC Press; and Synthesis 1:1-5 (1988). The 36P6D5 antisense oligonucleotides of the present invention include derivatives such as S-oligonucleotides (phosphorothioate derivatives or S-oligos, see, Jack Cohen, supra), which exhibit enhanced cancer cell growth inhibitory action. S-oligos (nucleoside phosphorothioates) are isoelectronic analogs of an oligonucleotide (O-oligo) in which a nonbridging oxygen atom of the phosphate group is replaced by a sulfur atom. The S-oligos of the present invention may be prepared by treatment of the corresponding O-oligos with 3H-1,2-benzodithiol-3-one-1,1-dioxide, which is a sulfur transfer reagent. See Iyer, R. P. et al, 1990, J. Org. Chem. 55:4693-4698; and Iyer, R. P. et al., 1990, J. Am. Chem. Soc. 112:1253-1254, the disclosures of which are fully incorporated by reference herein. Additional 36P6D5 antisense oligonucleotides of the present invention include morpholino antisense oligonucleotides known in the art (see e.g. Partridge et al., 1996, Antisense & Nucleic Acid Drug Development 6:169-175).

The 36P6D5 antisense oligonucleotides of the present invention typically may be RNA or DNA that is complementary to and stably hybridizes with the first 100 N-terminal codons or last 100 C-terminal codons of the 36P6D5 genomic sequence or the corresponding mRNA. While absolute complementarity is not required, high degrees of complementarity are preferred. Use of an oligonucleotide complementary to this region allows for the selective hybridization to 36P6D5 mRNA and not to mRNA specifying other regulatory subunits of protein kinase. Preferably, the 36P6D5 antisense oligonucleotides of the present invention are a 15 to 30-mer fragment of the antisense DNA molecule having a sequence that hybridizes to 36P6D5 mRNA. Optionally, 36P6D5 antisense oligonucleotide is a 30-mer oligonucleotide that is complementary to a region in the first 10 N-terminal codons and last 10 C-terminal codons of 36P6D5. Alternatively, the antisense molecules are modified to employ ribozymes in the inhibition of 36P6D5 expression (L. A. Couture & D. T. Stinchcomb, 1996, Trends Genet. 12: 510-515).

Further specific embodiments of this aspect of the invention include primers and primer pairs, which allow the specific amplification of the polynucleotides of the invention or of any specific parts thereof, and probes that selectively or specifically hybridize to nucleic acid molecules of the invention or to any part thereof. Probes may be labeled with a detectable marker, such as, for example, a radioisotope, fluorescent compound, bioluminescent compound, a chemiluminescent compound, metal chelator or enzyme. Such probes and primers can be used to detect the presence of a 36P6D5 polynucleotide in a sample and as a means for detecting a cell expressing a 36P6D5 protein.

Examples of such probes include polynucleotides comprising all or part of the human 36P6D5 cDNA sequences shown in SEQ ID NO: 1. Examples of primer pairs capable of specifically amplifying 36P6D5 mRNAs are also described in the Examples that follow. As will be understood by the skilled artisan, a great many different primers and probes may be prepared based on the sequences provided herein and used effectively to amplify and/or detect a 36P6D5 mRNA.

As used herein, a polynucleotide is said to be "isolated" when it is substantially separated from contaminant polynucleotides that correspond or are complementary to genes other than the 36P6D5 gene or that encode polypeptides other than 36P6D5 gene product or fragments thereof. A skilled artisan can readily employ nucleic acid isolation procedures to obtain an isolated 36P6D5 polynucleotide.

The 36P6D5 polynucleotides of the invention are useful for a variety of purposes, including but not limited to their use as probes and primers for the amplification and/or detection of the 36P6D5 gene(s), mRNA(s), or fragments thereof; as reagents for the diagnosis and/or prognosis of prostate cancer and other cancers; as coding sequences capable of directing the expression of 36P6D5 polypeptides; as tools for modulating or inhibiting the expression of the 36P6D5 gene(s) and/or translation of the 36P6D5 transcript(s); and as therapeutic agents.

Isolation of 36P6D5-Encoding Nucleic Acid Molecules

The 36P6D5 cDNA sequences described herein enable the isolation of other polynucleotides encoding 36P6D5 gene product(s), as well as the isolation of polynucleotides encoding 36P6D5 gene product homologs, alternatively spliced isoforms, allelic variants, and mutant forms of the 36P6D5 gene product. Various molecular cloning methods that can be employed to isolate full length cDNAs encoding a 36P6D5 gene are well known (See, e.g., Sambrook, J. et al., 1989, Molecular Cloning: A Laboratory Manual, 2d ed., Cold Spring Harbor Press, New York; Ausubel et al., eds., 1995, Current Protocols in Molecular Biology, Wiley and Sons). For example, lambda phage cloning methodologies may be conveniently employed, using commercially available cloning systems (e.g., Lambda ZAP Express, Stratagene). Phage clones containing 36P6D5 gene cDNAs may be identified by probing with a labeled 36P6D5 cDNA or a fragment thereof. For example, in one embodiment, the 36P6D5 cDNA (SEQ ID NO: 1) or a portion thereof can be synthesized and used as a probe to retrieve overlapping and full length cDNAs corresponding to a 36P6D5 gene. The 36P6D5 gene itself may be isolated by screening genomic DNA libraries, bacterial artificial chromosome libraries (BACs), yeast artificial chromosome libraries (YACs), and the like, with 36P6D5 DNA probes or primers.

Recombinant DNA Molecules and Host-vector Systems

The invention also provides recombinant DNA or RNA molecules containing a 36P6D5 polynucleotide, including but not limited to phages, plasmids, phagemids, cosmids, YACs, BACs, as well as various viral and non-viral vectors well known in the art, and cells transformed or transfected with such recombinant DNA or RNA molecules. As used herein, a recombinant DNA or RNA molecule is a DNA or RNA molecule that has been subjected to molecular manipulation in vitro. Methods for generating such molecules are well known (see, e.g., Sambrook et al, 1989, supra).

The invention further provides a host-vector system comprising a recombinant DNA molecule containing a 36P6D5 polynucleotide within a suitable prokaryotic or eukaryotic host cell. Examples of suitable eukaryotic host cells include a yeast cell, a plant cell, or an animal cell, such as a mammalian cell or an insect cell (e.g., a baculovirus-infectible cell such as an Sf9 or HighFive cell). Examples of suitable mammalian cells include various prostate cancer cell lines such as PrEC, LNCaP and TsuPr1, other transfectable or transducible prostate cancer cell lines, as well as a number of mammalian cells routinely used for the expression of recombinant proteins (e.g., COS, CHO, 293, 293T cells). More particularly, a polynucleotide comprising the coding sequence of 36P6D5 may be used to generate 36P6D5 proteins or fragments thereof using any number of host-vector systems routinely used and widely known in the art.

A wide range of host-vector systems suitable for the expression of 36P6D5 proteins or fragments thereof are available (see, e.g., Sambrook et al., 1989, supra; Current Protocols in Molecular Biology, 1995, supra). Preferred vectors for mammalian expression include but are not limited to pcDNA 3.1 myc-His-tag (Invitrogen) and the retroviral vector pSRαtkneo (Muller et al., 1991, MCB 11:1785). Using these expression vectors, 36P6D5 may be preferably expressed in several prostate cancer and non-prostate cell lines, including for example 293, 293T, rat-1, NIH 3T3 and TsuPr1. The host-vector systems of the invention are useful for the production of a 36P6D5 protein or fragment thereof. Such host-vector systems may be employed to study the functional properties of 36P6D5 and 36P6D5 mutations.

Recombinant human 36P6D5 protein may be produced by mammalian cells transfected with a construct encoding 36P6D5. In an illustrative embodiment described in the Examples, 293T cells can be transfected with an expression plasmid encoding 36P6D5, the 36P6D5 protein is expressed in the 293T cells, and the recombinant 36P6D5 protein can be isolated using standard purification methods (e.g., affinity purification using anti-36P6D5 antibodies). In another embodiment, also described in the Examples herein, the 36P6D5 coding sequence is subcloned into the retroviral vector pSRαMSVtkneo and used to infect various mammalian cell lines, such as NIH 3T3, TsuPr1, 293 and rat-1 in order to establish 36P6D5 expressing cell lines. Various other expression systems well known in the art may also be employed. Expression constructs encoding a leader peptide joined in frame to the 36P6D5 coding sequence may be used for the generation of a secreted form of recombinant 36P6D5 protein.

Proteins encoded by the 36P6D5 genes, or by fragments thereof, will have a variety of uses, including but not limited to generating antibodies and in methods for identifying ligands and other agents and cellular constituents that bind to a 36P6D5 gene product. Antibodies raised against a 36P6D5 protein (like 36P6D5 polynucleotides) or fragment thereof may be useful in diagnostic and prognostic assays, and imaging methodologies in the management of human cancers characterized by expression of 36P6D5 protein, including but not limited to cancers of the kidney lung, colon, prostate, brain, bladder, pancreas, ovaries, lung, and breast (see e.g. FIGS. 4, 6 and 7). Such antibodies may be expressed intracellularly and used in methods of treating patients with such cancers. Various immunological assays useful for the detection of 36P6D5 proteins are contemplated, including but not limited to FACS analysis, various types of radioimmunoassays, enzyme-linked immunosorbent assays (ELISA), enzyme-linked immunofluorescent assays (ELIFA), immunocytochemical methods, and the like. Such antibodies may be labeled and used as immunological imaging reagents capable of detecting 36P6D5 expressing cells (e.g., in radioscintigraphic imaging methods). 36P6D5 proteins may also be particularly useful in generating cancer vaccines, as further described below.

36P6D5 Polypeptides

Another aspect of the present invention provides 36P6D5 proteins and polypeptide fragments thereof. The 36P6D5 proteins of the invention include those specifically identified herein, as well as allelic variants, conservative substitution variants and homologs that can be isolated/generated and characterized without undue experimentation following the methods outlined below. Fusion proteins that combine parts of different 36P6D5 proteins or fragments thereof, as well as fusion proteins of a 36P6D5 protein and a heterologous polypeptide are also included. Such 36P6D5 proteins will be collectively referred to as the 36P6D5 proteins, the proteins of the invention, or 36P6D5. As used herein, the term "36P6D5 polypeptide" refers to a polypeptide fragment or a 36P6D5 protein of at least 6 amino acids, preferably at least 15 amino acids.

Specific embodiments of 36P6D5 proteins comprise a polypeptide having the amino acid sequence of human 36P6D5 as shown in SEQ ID NO: 2. Alternatively, embodiments of 36P6D5 proteins comprise variant polypeptides having alterations in the amino add sequence of human 36P6D5 as shown in SEQ ID NO: 2.

In general, naturally occurring allelic variants of human 36P6D5 will share a high degree of structural identity and homology (e.g., 90% or more identity). Typically, allelic variants of the 36P6D5 proteins will contain conservative amino acid substitutions within the 36P6D5 sequences described herein or will contain a substitution of an amino acid from a corresponding position in a 36P6D5 homologue. One class of 36P6D5 allelic variants will be proteins that share a high degree of homology with at least a small region of a particular 36P6D5 amino acid sequence, but will further contain a radical departure from the sequence, such as a non-conservative substitution, truncation, insertion or frame shift.

Conservative amino acid substitutions can frequently be made in a protein without altering either the conformation or the function of the protein. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

Embodiments of the invention disclosed herein include a wide variety of art accepted variants of 36P6D5 proteins such as polypeptides having amino acid insertions, deletions and substitutions. 36P6D5 variants can be made using methods known in the art such as site-directed mutagenesis, alanine scanning, and PCR mutagenesis. Site-directed mutagenesis (Carter et al., 1986, Nucl. Acids Res. 13:4331; Zoller et al., 1987, Nucl. Acids Res. 10:6487), cassette mutagenesis (Wells et al., 1985, Gene 34:315), restriction selection mutagenesis (Wells et al., 1986, Philos. Trans. R. Soc. London Ser. A, 317:415) or other known techniques can be performed on the cloned DNA to produce the 36P6D5 variant DNA. Scanning ammo acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions (Creighton, The Proteins, (W.H. Freeman & Co., N.Y.); Chothia, 1976, J. Mol. Biol., 150:1). If alanine substitution does not yield adequate amounts of variant, an isosteric amino acid can be used.

As defined herein, 36P6D5 variants have the distinguishing attribute of having at least one epitope in common with a 36P6D5 protein having the amino acid sequence of SEQ ID NO: 2, such that an antibody that specifically binds to a 36P6D5 variant will also specifically bind to the 36P6D5 protein having the amino acid sequence of SEQ ID NO: 2. A polypeptide ceases to be a variant of the protein shown in SEQ ID NO: 2 when it no longer contains an epitope capable of being recognized by an antibody that specifically binds to a 36P6D5 protein. Those skilled in the art understand that antibodies that recognize proteins bind to epitopes of varying size, and a grouping of the order of about six amino acids, contiguous or not, is regarded as a typical number of amino acids in a minimal epitope. See e.g. Hebbes et al., Mol Immunol (1989) 26(9):865-73; Schwartz et al., J Immunol (1985) 135(4):2598-608. As there are approximately 20 amino acids that can be included at a given position within the minimal 6 amino acid epitope, an approximation of the odds of such an epitope occurring by chance are about $20^6$ or about 1 in 64 million. Another specific class of 36P6D5 protein variants shares 90% or more identity with the amino acid sequence of SEQ ID NO: 2. Another specific class of 36P6D5 protein variants comprises one or more of the 36P6D5 biological motifs described below.

As discussed above, embodiments of the claimed invention include polypeptides containing less than the 235 amino acid sequence of the 36P6D5 protein shown in SEQ ID NO: 2 (and the polynucleotides encoding such polypeptides). For example, representative embodiments of the invention disclosed herein include polypeptides consisting of about amino acid 1 to about amino acid 10 of the 36P6D5 protein shown in SEQ ID NO: 2, polypeptides consisting of about amino acid 20 to about amino acid 30 of the 36P6D5 protein shown in SEQ ID NO: 2, polypeptides consisting of about amino acid 30 to about amino acid 40 of the 36P6D5 protein shown in SEQ ID NO: 2, polypeptides consisting of about amino acid 40 to about amino acid 50 of the 36P6D5 protein shown in SEQ ID NO: 2, polypeptides consisting of about amino acid 50 to about amino acid 60 of the 36P6D5 protein shown in SEQ ID NO: 2, polypeptides consisting of about amino acid 60 to about amino acid 70 of the 36P6D5 protein shown in SEQ ID NO: 2, polypeptides consisting of about amino acid 70 to about amino acid 80 of the 36P6D5 protein shown in SEQ ID NO: 2, polypeptides consisting of about amino acid 80 to about amino acid 90 of the 36P6D5 protein shown in SEQ ID NO: 2 and polypeptides consisting of about amino acid 90 to about amino acid 100 of the 36P6D5 protein shown in SEQ ID NO: 2, etc. Following this scheme, polypeptides consisting of portions of the amino acid sequence of amino acids 100-235 of the 36P6D5 protein are typical embodiments of the invention. Polypeptides consisting of larger portions of the 36P6D5 protein are also contemplated. For example polypeptides consisting of about amino acid 1 (or 20 or 30 or 40 etc.) to about amino acid 20, (or 30, or 40 or 50 etc.) of the 36P6D5 protein shown in SEQ ID NO: 2 may be generated by a variety of techniques well known in the art.

Additional illustrative embodiments of the invention disclosed herein include 36P6D5 polypeptides containing the amino acid residues of one or more of the biological motifs contained within the 36P6D5 polypeptide sequence as shown in SEQ ID NO: 2. In one embodiment, typical polypeptides of the invention can contain one or more of the 36P6D5 N-glycosylation sites such as NVTA at residues 120-123 and/or NHSD at residues 208-211 (SEQ ID NO: 2). In another embodiment, typical polypeptides of the invention can contain one or more of the 36P6D5 protein kinase C phosphorylation sites such as SIR at residues 43-45 and/or STR at residues 160-162 (SEQ ID NO: 2). In another embodiment, typical polypeptides of the invention can contain one or more of the 36P6D5 casein kinase II phosphorylation sites such as SIGE at residues 46-49 and/or TYDD at residues 155-158 (SEQ ID NO: 2). In another embodiment, typical polypeptides of the invention can contain one or more of the N-myristoylation sites such as GGGRSK at residues 81-86, GINIAI at residues 108-113 and/or GNVTAT at residues 119-124 (SEQ ID NO: 2). In another embodiment, typical polypeptides of the invention can contain the amino acid permease signature AGGLLKVVFVVFASLCAWYSGYLLAELIPDAP at residues 5-36 (SEQ ID NO: 2). In another embodiment, typical polypeptides of the invention can contain the signal sequence shown in FIG. 1. In yet another embodiment, typical polypeptides of the invention can contain one or more immunogenic epitopes identified by a process described herein such as those shown in Table 1. Related embodiments of these inventions include polypeptides containing combinations of the different motifs discussed above with preferable embodiments being those which contain no insertions, deletions or substitutions either within the motifs or the intervening sequences of these polypeptides. In addition, embodiments which include a number of either N-terminal and/or C-terminal amino acid residues on either side of these motifs may be desirable (to, for example, include a greater portion of the polypeptide architecture in which the motif is located). Typically the number of N-terminal and/or C-terminal amino acid residues on either side of a motif is between about 5 to about 50 amino acid residues.

Illustrative examples of such embodiments includes a polypeptide having one or more motifs selected from the group consisting of SIR and/or SIGE and/or NHSD (SEQ ID NO: 2). Alternatively polypeptides having other combinations of the biological motifs disclosed herein are also contemplated such as a polypeptide having SIR and any one of the other biological motifs such as SIGE or a polypeptide having TYDD and any one of the other biological motifs such as GGGRSK etc. (SEQ ID NO: 2).

Polypeptides consisting of one or more of the 36P6D5 motifs discussed above are useful in elucidating the specific characteristics of a malignant phenotype in view of the observation that the 36P6D5 motifs discussed above are associated with growth dysregulation and because 36P6D5 is overexpressed in cancers (FIGS. 4, 6 and 7). Casein kinase II and protein kinase C for example are enzymes known to be associated with the development of the malignant phenotype (see e.g. Chen et al., 1998, Lab Invest., 78(2):165-174; Gaiddon et al., 1995, Endocrinology 136(10):4331-4338; Hall et al., 1996, Nucleic Acids Research 24(6):1119-1126; Peterziel et al., 1999, Oncogene 18(46):6322-6329; and O'Brian, 1998, Oncol. Rep. 5(2): 305-309). Moreover, both glycosylation and myristoylation are protein modifications also associated with cancer and cancer progression (see e.g. Dennis et al., 1999, Biochim. Biophys. Acta 1473(1):21-34; Raju et al., 1997, Exp. Cell Res. 235(1):145-154).

The polypeptides of the preceding paragraphs have a number of different specific uses. As 36P6D5 is shown to be expressed in a variety of cancers including kidney, prostate, bladder, ovarian, breast, pancreas, colon and lung cancer cell lines and/or patient samples (see e.g. FIGS. 4, 6 and 7), these polypeptides may be used in methods assessing the status of 36P6D5 gene products in normal versus cancerous tissues and elucidating the malignant phenotype. Typically, polypeptides encoding specific regions of the 36P6D5 protein may be used to assess the presence of perturbations (such as deletions, insertions, point mutations etc.) in specific regions of the 36P6D5 gene products (such as regions containing the RNA binding motifs). Exemplary assays can utilize antibodies targeting a 36P6D5 polypeptide containing the amino acid residues of one or more of the biological motifs contained within the 36P6D5 polypeptide sequence in order to evaluate the characteristics of this region in normal versus cancerous tissues. Alternatively, 36P6D5 polypeptides containing the amino acid residues of one or more of the biological motifs contained within the 36P6D5 polypeptide sequence can be used to screen for factors that interact with that region of 36P6D5.

As discussed above, redundancy in the genetic code permits variation in 36P6D5 gene sequences. In particular, one skilled in the art will recognize specific codon preferences by a specific host species and can adapt the disclosed sequence as preferred for a desired host. For example, preferred codon sequences typically have rare codons (i.e., codons having a usage frequency of less than about 20% in known sequences of the desired host) replaced with higher frequency codons. Codon preferences for a specific organism may be calculated, for example, by utilizing codon usage tables available on the Internet at the following address: http://www.dna.affrc.go.jp/~nakamura/codon.html. Nucleotide sequences that have been optimized for a particular host species by replacing any codons having a usage frequency of less than about 20% are referred to herein as "codon optimized sequences."

Additional sequence modifications are known to enhance protein expression in a cellular host. These include elimination of sequences encoding spurious polyadenylation signals, exon/intron splice site signals, transposon-like repeats, and/or other such well-characterized sequences that may be deleterious to gene expression. The GC content of the sequence may be adjusted to levels average for a given cellular host, as calculated by reference to known genes expressed in the host cell. Where possible, the sequence may also be modified to avoid predicted hairpin secondary mRNA structures. Other useful modifications include the addition of a translational initiation consensus sequence at the start of the open reading frame, as described in Kozak, 1989, Mol. Cell Biol., 9:5073-5080. Nucleotide sequences that have been optimized for expression in a given host species by elimination of spurious polyadenylation sequences, elimination of exon/intron splicing signals, elimination of transposon-like repeats and/or optimization of GC content in addition to codon optimization are referred to herein as an "expression enhanced sequence."

36P6D5 proteins may be embodied in many forms, preferably in isolated form. As used herein, a protein is said to be "isolated" when physical, mechanical or chemical methods are employed to remove the 36P6D5 protein from cellular constituents that are normally associated with the protein. A skilled artisan can readily employ standard purification methods to obtain an isolated 36P6D5 protein. A purified 36P6D5 protein molecule will be substantially free of other proteins or molecules that impair the binding of 36P6D5 to antibody or other ligand. The nature and degree of isolation and purification will depend on the intended use. Embodiments of a 36P6D5 protein include a purified 36P6D5 protein and a functional, soluble 36P6D5 protein. In one form, such functional, soluble 36P6D5 proteins or fragments thereof retain the ability to bind antibody or other ligand.

The invention also provides 36P6D5 polypeptides comprising biologically active fragments of the 36P6D5 amino acid sequence, such as a polypeptide corresponding to part of the amino acid sequence for 36P6D5 as shown in SEQ ID NO: 2. Such polypeptides of the invention exhibit properties of the 36P6D5 protein, such as the ability to elicit the generation of antibodies that specifically bind an epitope associated with the 36P6D5 protein.

36P6D5 polypeptides can be generated using standard peptide synthesis technology or using chemical cleavage methods well known in the art based on the amino acid sequences of the human 36P6D5 proteins disclosed herein. Alternatively, recombinant methods can be used to generate nucleic acid molecules that encode a polypeptide fragment of a 36P6D5 protein. In this regard, the 36P6D5-encoding nucleic acid molecules described herein provide means for generating defined fragments of 36P6D5 proteins. 36P6D5 polypeptides are particularly useful in generating and characterizing domain specific antibodies (e.g., antibodies recognizing an extracellular or intracellular epitope of a 36P6D5 protein), in identifying agents or cellular factors that bind to 36P6D5 or a particular structural domain thereof and in various therapeutic contexts, including but not limited to cancer vaccines.

36P6D5 polypeptides containing particularly interesting structures can be predicted and/or identified using various analytical techniques well known in the art, including, for example, the methods of Chou-Fasman, Garnier-Robson, Kyte-Doolittle, Eisenberg, Karplus-Schultz or Jameson-Wolf analysis, or on the basis of immunogenicity. Fragments containing such structures are particularly useful in generating subunit specific anti-36P6D5 antibodies or in identifying cellular factors that bind to 36P6D5.

In an embodiment described in the examples that follow, 36P6D5 can be conveniently expressed in cells (such as 293T cells) transfected with a commercially available expression vector such as a CMV-driven expression vector encoding 36P6D5 with a C-terminal 6×His and MYC tag (pcDNA3.1/mycHIS, Invitrogen or Tag5, GenHunter Corporation, Nashville Tenn.). The Tag5 vector provides an IgGK secretion signal that can be used to facilitate the production of a secreted 36P6D5 protein in transfected cells. The secreted HIS-tagged 36P6D5 in the culture media may be purified using a nickel column using standard techniques.

Modifications of 36P6D5 such as covalent modifications are included within the scope of this invention. One type of covalent modification includes reacting targeted amino acid residues of a 36P6D5 polypeptide with an organic derivatizing agent that is capable of reacting with selected side chains or the N- or C-terminal residues of the 36P6D5. Another type of covalent modification of the 36P6D5 polypeptide included within the scope of this invention comprises altering the native glycosylation pattern of the polypeptide. "Altering the native glycosylation pattern" is intended for purposes herein to mean deleting one or more carbohydrate moieties found in native sequence 36P6D5 (either by removing the underlying glycosylation site or by deleting the glycosylation by chemical and/or enzymatic means), and/or adding one or more glycosylation sites that are not present in the native sequence 36P6D5. In addition, the phrase includes qualitative changes in the glycosylation of the native proteins, involving a change in the nature and proportions of the various carbohydrate moieties present. Another type of covalent modification of 36P6D5 comprises linking the 36P6D5 polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The 36P6D5 of the present invention may also be modified in a way to form a chimeric molecule comprising 36P6D5 fused to another, heterologous polypeptide or amino acid sequence. In one embodiment, such a chimeric molecule comprises a fusion of the 36P6D5 with a polyhistidine epitope tag, which provides an epitope to which immobilized nickel can selectively bind. The epitope tag is generally placed at the amino- or carboxyl-terminus of the 36P6D5. In an alternative embodiment, the chimeric molecule may comprise a fusion of the 36P6D5 with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a 36P6D5 polypeptide in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

36P6D5 Antibodies

The term "antibody" is used in the broadest sense and specifically covers single anti-36P6D5 monoclonal antibodies (including agonist, antagonist and neutralizing antibodies) and anti-36P6D5 antibody compositions with polyepitopic specificity. The term "monoclonal antibody" (mAb) as used herein refers to an antibody obtained from a population of substantially homogeneous antibodies, i.e. the antibodies comprising the individual population are identical except for possible naturally-occurring mutations that may be present in minor amounts.

Another aspect of the invention provides antibodies that bind to 36P6D5 proteins and polypeptides. The most preferred antibodies will specifically bind to a 36P6D5 protein and will not bind (or will bind weakly) to non-36P6D5 proteins and polypeptides. Anti-36P6D5 antibodies that are particularly contemplated include monoclonal and polyclonal antibodies as well as fragments containing the antigen binding domain and/or one or more complementarity determining regions of these antibodies. As used herein, an antibody fragment is defined as at least a portion of the variable region of the immunoglobulin molecule that binds to its target, i.e., the antigen binding region.

36P6D5 antibodies of the invention may be particularly useful in prostate cancer diagnostic and prognostic assays, and imaging methodologies. Intracellularly expressed antibodies (e.g., single chain antibodies) may be therapeutically useful in treating cancers in which the expression of 36P6D5 is involved, such as for example advanced and metastatic prostate cancers. Such antibodies may be useful in the treatment, diagnosis, and/or prognosis of other cancers, to the extent 36P6D5 is also expressed or overexpressed in other types of cancers such as prostate, kidney, bladder, ovarian, breast, pancreas, colon and lung cancers.

36P6D5 antibodies may also be used therapeutically by, for example, modulating or inhibiting the biological activity of a 36P6D5 protein or targeting and destroying cancer cells expressing a 36P6D5 protein or 36P6D5 binding partner. Because 36P6D5 is a secreted protein, antibodies may be therapeutically useful for blocking 36P6D5's ability to bind to its receptor or interact with other proteins through which it exerts its biological activity.

The invention also provides various immunological assays useful for the binding to, detection and quantification of 36P6D5 and mutant 36P6D5 proteins and polypeptides. Such methods and assays generally comprise one or more 36P6D5 antibodies capable of recognizing and binding a 36P6D5 or mutant 36P6D5 protein, as appropriate, and may be performed within various immunological assay formats well known in the art, including but not limited to various types of radioimmunoassays, enzyme-linked immunosorbent assays (ELISA), enzyme-linked immunofluorescent assays (ELIFA), and the like. In addition, immunological imaging methods capable of detecting prostate cancer and other cancers expressing 36P6D5 are also provided by the invention, including but not limited to radioscintigraphic imaging methods using labeled 36P6D5 antibodies. Such assays may be clinically useful in the detection, monitoring, and prognosis of 36P6D5 expressing cancers such as prostate, breast, pancreas, colon and ovarian cancer cell lines.

36P6D5 antibodies may also be used in methods for purifying 36P6D5 and mutant 36P6D5 proteins and polypeptides and for isolating 36P6D5 homologues and related molecules. For example, in one embodiment, the method of purifying a 36P6D5 protein comprises incubating a 36P6D5 antibody, which has been coupled to a solid matrix, with a lysate or other solution containing 36P6D5 under conditions that permit the 36P6D5 antibody to bind to 36P6D5; washing the solid matrix to eliminate impurities; and eluting the 36P6D5 from the coupled antibody. Other uses of the 36P6D5 antibodies of the invention include generating anti-idiotypic antibodies that mimic the 36P6D5 protein.

Various methods for the preparation of antibodies are well known in the art. For example, antibodies may be prepared by immunizing a suitable mammalian host using a 36P6D5 protein, peptide, or fragment, in isolated or immunoconjugated form (Harlow, and Lane, eds., 1988, Antibodies: A Laboratory Manual, CSH Press; Harlow, 1989, Antibodies, Cold Spring Harbor Press, NY). In addition, fusion proteins of 36P6D5 may also be used, such as a 36P6D5 GST-fusion protein. In a particular embodiment, a GST fusion protein comprising all or most of the open reading frame amino acid sequence of SEQ ID NO: 2 may be produced and used as an immunogen to generate appropriate antibodies. In another embodiment, a 36P6D5 peptide may be synthesized and used as an immunogen.

In addition, naked DNA immunization techniques known in the art may be used (with or without purified 36P6D5 protein or 36P6D5 expressing cells) to generate an immune response to the encoded immunogen (for review, see Donnelly et al., 1997, Ann. Rev. Immunol. 15:617-648).

The amino acid sequence of the 36P6D5 as shown in SEQ ID NO: 2 may be used to select specific regions of the 36P6D5 protein for generating antibodies. For example, hydrophobicity and hydrophilicity analyses of the 36P6D5 amino acid sequence may be used to identify hydrophilic regions in the 36P6D5 structure. Regions of the 36P6D5 protein that show immunogenic structure, as well as other regions and domains, can readily be identified using various other methods known in the art, such as Chou-Fasman, Garnier-Robson, Kyte-Doolittle, Eisenberg, Karplus-Schultz or Jameson-Wolf analysis.

Illustrating this, the binding of peptides from 36P6D5 proteins to the human MHC class I molecule HLA-A2 are predicted and shown in Table 1 below. Specifically, the complete amino acid sequences of 36P6D5 proteins was entered into the HLA Peptide Motif Search algorithm found in the Bioinformatics and Molecular Analysis Section (BIMAS) Web site (http://bimas.dcrt.nih.gov/). The HLA Peptide Motif Search algorithm was developed by Dr. Ken Parker based on binding of specific peptide sequences in the groove of HLA Class I molecules and specifically HLA-A2 (see e.g. Falk et al., Nature 351: 290-6 (1991); Hunt et al., Science 255:1261-3 (1992); Parker et al., J. Immunol. 149:3580-7 (1992); Parker et al., J. Immunol. 152:163-75 (1994)). This algorithm allows location and ranking of 8-mer, 9-mer, and 10-mer peptides from a complete protein sequence for predicted binding to HLA-A2 as well as other HLA Class I molecules. Most HLA-A2 binding peptides are 9-mers favorably containing a leucine (L) at position 2 and a valine (V) or leucine (L) at position 9 (Parker et al., J. Immunol. 149:3580-7 (1992)). The results of 36P6D5 predicted binding peptides are shown in Table 1 below. In Table 1, the top 10 ranking candidates for each family member are shown along with their location, the amino acid sequence of each specific peptide, and an estimated binding score. The binding score corresponds to the estimated half-time of dissociation of complexes containing the peptide at 37° C. at pH 6.5. Peptides with the highest binding score are predicted to be the most tightly bound to HLA Class I on the cell surface and thus represent the best immunogenic targets for T-cell recognition. Actual binding of peptides to HLA-A2 can be evaluated by stabilization of HLA-A2 expression on the antigen-processing defective cell line T2 (see e.g. Xue et al., Prostate 30:73-8 (1997) and Peshwa et al., Prostate 36:129-38 (1998)). Immunogenicity of specific peptides can be evaluated in vitro by stimulation of CD8+ cytotoxic T lymphocytes (CTL) in the presence of dendritic cells.

Methods for preparing a protein or polypeptide for use as an immunogen and for preparing immunogenic conjugates of a protein with a carrier such as BSA, KLH, or other carrier proteins are well known in the art. In some circumstances, direct conjugation using, for example, carbodiimide reagents may be used; in other instances linking reagents such as those supplied by Pierce Chemical Co., Rockford, Ill., may be effective. Administration of a 36P6D5 immunogen is conducted generally by injection over a suitable time period and with use of a suitable adjuvant, as is generally understood in the art. During the immunization schedule, titers of antibodies can be taken to determine adequacy of antibody formation.

36P6D5 monoclonal antibodies are preferred and may be produced by various means well known in the art. For example, immortalized cell lines that secrete a desired monoclonal antibody may be prepared using the standard hybridoma technology of Kohler and Milstein or modifications that immortalize producing B cells, as is generally known. The immortalized cell lines secreting the desired antibodies are screened by immunoassay in which the antigen is the 36P6D5 protein or a 36P6D5 fragment. When the appropriate immortalized cell culture secreting the desired antibody is identified, the cells may be expanded and antibodies produced either from in vitro cultures or from ascites fluid.

The antibodies or fragments may also be produced, using current technology, by recombinant means. Regions that bind specifically to the desired regions of the 36P6D5 protein can also be produced in the context of chimeric or CDR grafted antibodies of multiple species origin. Humanized or human 36P6D5 antibodies may also be produced and are preferred for use in therapeutic contexts. Methods for humanizing murine and other non-human antibodies by substituting one or more of the non-human antibody CDRs for corresponding human antibody sequences are well known (see for example, Jones et al., 1986, Nature 321:522-525; Riechmann et al., 1988, Nature 332:323-327; Verhoeyen et al., 1988, Science 239:1534-1536). See also, Carter et al., 1993, Proc. Natl. Acad. Sci. USA 89:4285 and Sims et al., 1993, J. Immunol. 151:2296. Methods for producing fully human monoclonal antibodies include phage display and transgenic methods (for review, see Vaughan et al., 1998, Nature Biotechnology 16:535-539).

Fully human 36P6D5 monoclonal antibodies may be generated using cloning technologies employing large human Ig gene combinatorial libraries (i.e., phage display) (Griffiths and Hoogenboom, Building an in vitro immune system: human antibodies from phage display libraries. In: Clark, M., ed., 1993, Protein Engineering of Antibody Molecules for Prophylactic and Therapeutic Applications in Man, Nottingham Academic, pp 45-64; Burton and Barbas, Human Antibodies from combinatorial libraries. Id., pp 65-82). Fully human 36P6D5 monoclonal antibodies may also be produced using transgenic mice engineered to contain human immunoglobulin gene loci as described in PCT Patent Application WO98/24893, Kucherlapati and Jakobovits et al., published Dec. 3, 1997 (see also, Jakobovits, 1998, Exp. Opin. Invest. Drugs 7(4):607-614). This method avoids the in vitro manipulation required with phage display technology and efficiently produces high affinity authentic human antibodies.

Reactivity of 36P6D5 antibodies with a 36P6D5 protein may be established by a number of well known means, including western blot, immunoprecipitation, ELISA, and FACS analyses using, as appropriate, 36P6D5 proteins, peptides, 36P6D5-expressing cells or extracts thereof.

A 36P6D5 antibody or fragment thereof of the invention may be labeled with a detectable marker or conjugated to a second molecule. Suitable detectable markers include, but are not limited to, a radioisotope, a fluorescent compound, a bioluminescent compound, chemiluminescent compound, a metal chelator or an enzyme. A second molecule for conjugation to the 36P6D5 antibody can be selected in accordance with the intended use. For example, for therapeutic use, the second molecule can be a toxin or therapeutic agent. Further, bi-specific antibodies specific for two or more 36P6D5 epitopes may be generated using methods generally known in the art. Homodimeric antibodies may also be generated by cross-linking techniques known in the art (e.g., Wolff et al., 1993, Cancer Res. 53: 2560-2565).

36P6D5 Transgenic Animals

Nucleic acids that encode 36P6D5 or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA that is integrated into the genome of a cell from which a transgenic animal develops. In one embodiment, cDNA encoding 36P6D5 can be used to clone genomic DNA encoding 36P6D5 in accordance with established techniques and the genomic sequences used to generate transgenic animals that contain cells that express DNA encoding 36P6D5. Methods for generating transgenic animals, particularly animals such as mice or rats, have become conventional in the art and are described, for example, in U.S. Pat. Nos. 4,736,866 and 4,870,009. Typically, particular cells would be targeted for 36P6D5 transgene incorporation with tissue-specific enhancers. Transgenic animals that include a copy of a transgene encoding 36P6D5 introduced into the germ line of the animal at an embryonic stage can be used to examine the effect of increased expression of DNA encoding 36P6D5. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of 36P6D5 can be used to construct a 36P6D5 "knock out" animal that has a defective or altered gene encoding 36P6D5 as a result of homologous recombination between the endogenous gene encoding 36P6D5 and altered genomic DNA encoding 36P6D5 introduced into an embryonic cell of the animal. For example, cDNA encoding 36P6D5 can be used to clone genomic DNA encoding 36P6D5 in accordance with established techniques. A portion of the genomic DNA encoding 36P6D5 can be deleted or replaced with another gene, such as a gene encoding a selectable marker that can be used to monitor integration. Typically, several kilobases of unaltered flanking DNA (both at the 5' and 3' ends) are included in the vector (see e.g., Thomas and Capecchi, 1987, Cell 51:503) for a description of homologous recombination vectors]. The vector is introduced into an embryonic stem cell line (e.g., by electroporation) and cells in which the introduced DNA has homologously recombined with the endogenous DNA are selected (see e.g., Li et al., 1992, Cell 69:915). The selected cells are then injected into a blastocyst of an animal (e.g., a mouse or rat) to form aggregation chimeras (see e.g., Bradley, in Robertson, ed., 1987, Teratocarcinomas and Embryonic Stem Cells: A Practical Approach, (IRL, Oxford), pp. 113-152). A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the 36P6D5 polypeptide.

Methods for the Detection of 36P6D5

Another aspect of the present invention relates to methods for detecting 36P6D5 polynucleotides and 36P6D5 proteins and variants thereof, as well as methods for identifying a cell that expresses 36P6D5. The expression profile of 36P6D5 makes it a potential diagnostic marker for local and/or metastasized disease. Northern blot analysis suggests that different tissues express different isoforms of 36P6D5. The 36P6D5 isoforms in prostate cancer appear to be different from the isoform expressed in normal prostate. In this context, the status of 36P6D5 gene products may provide information useful for predicting a variety of factors including susceptibility to advanced stage disease, rate of progression, and/or tumor aggressiveness. As discussed in detail below, the status of 36P6D5 gene products in patient samples may be analyzed by a variety protocols that are well known in the art including immunohistochemical analysis, the variety of Northern blotting techniques including in situ hybridization, RT-PCR analysis (for example on laser capture micro-dissected samples), western blot analysis and tissue array analysis.

More particularly, the invention provides assays for the detection of 36P6D5 polynucleotides in a biological sample, such as serum, bone, prostate, and other tissues, urine, semen, cell preparations, and the like. Detectable 36P6D5 polynucleotides include, for example, a 36P6D5 gene or fragments thereof, 36P6D5 mRNA, alternative splice variant 36P6D5 mRNAs, and recombinant DNA or RNA molecules containing a 36P6D5 polynucleotide. A number of methods for amplifying and/or detecting the presence of 36P6D5 polynucleotides are well known in the art and may be employed in the practice of this aspect of the invention.

In one embodiment, a method for detecting a 36P6D5 mRNA in a biological sample comprises producing cDNA from the sample by reverse transcription using at least one primer; amplifying the cDNA so produced using a 36P6D5 polynucleotides as sense and antisense primers to amplifying 36P6D5 cDNAs therein; and detecting the presence of the amplified 36P6D5 cDNA. Optionally, the sequence of the amplified 36P6D5 cDNA can be determined. In another embodiment, a method of detecting a 36P6D5 gene in a biological sample comprises first isolating genomic DNA from the sample; amplifying the isolated genomic DNA using 36P6D5 polynucleotides as sense and antisense primers to amplify the 36P6D5 gene therein; and detecting the presence of the amplified 36P6D5 gene. Any number of appropriate sense and antisense probe combinations may be designed from the nucleotide sequences provided for the 36P6D5 (SEQ ID NO: 1) and used for this purpose.

The invention also provides assays for detecting the presence of a 36P6D5 protein in a tissue of other biological sample such as serum, bone, prostate, and other tissues, urine, cell preparations, and the like. Methods for detecting a 36P6D5 protein are also well known and include, for example, immunoprecipitation, immunohistochemical analysis, Western Blot analysis, molecular binding assays, ELISA, ELIFA and the like. For example, in one embodiment, a method of detecting the presence of a 36P6D5 protein in a biological sample comprises first contacting the sample with a 36P6D5 antibody, a 36P6D5-reactive fragment thereof, or a recombinant protein containing an antigen binding region of a 36P6D5 antibody; and then detecting the binding of 36P6D5 protein in the sample thereto.

Methods for identifying a cell that expresses 36P6D5 are also provided. In one embodiment, an assay for identifying a cell that expresses a 36P6D5 gene comprises detecting the presence of 36P6D5 mRNA in the cell. Methods for the detection of particular mRNAs in cells are well known and include, for example, hybridization assays using complementary DNA probes (such as in situ hybridization using labeled 36P6D5 riboprobes, Northern blot and related techniques) and various nucleic acid amplification assays (such as RT-PCR using complementary primers specific for 36P6D5, and other amplification type detection methods, such as, for example, branched DNA, SISBA, TMA and the like). Alternatively, an assay for identifying a cell that expresses a 36P6D5 gene comprises detecting the presence of 36P6D5 protein in the cell or secreted by the cell. Various methods for the detection of proteins are well known in the art and may be employed for the detection of 36P6D5 proteins and 36P6D5 expressing cells.

36P6D5 expression analysis may also be useful as a tool for identifying and evaluating agents that modulate 36P6D5 gene expression. For example, 36P6D5 expression is significantly upregulated in prostate cancer, and may also be expressed in other cancers. Identification of a molecule or biological agent that could inhibit 36P6D5 expression or over-expression in cancer cells may be of therapeutic value. Such an agent may be identified by using a screen that quantifies 36P6D5 expression by RT-PCR, nucleic acid hybridization or antibody binding.

Assays for Circulating and Excreted 36P6D5

Mature 36P6D5 protein has an N-terminal signal sequence in the cDNA encoded ORF. Because 36P6D5 is a secreted protein expressed in cancers of the prostate, kidney, bladder, breast, colon, ovary, pancreas, and possibly other cancers, tumors expressing 36P6D5 would be expected to secrete 36P6D5 into the vasculature, and/or excreted into urine or semen, where the protein may be detected and quantified using assays and techniques well known in the molecular diagnostic field. Detecting and quantifying the levels of circulating or excreted 36P6D5 is expected to have a number of uses in the diagnosis, staging, and prognosis of cancers expressing 36P6D5, including but not limited to cancers of the prostate, kidney, bladder, breast, colon, ovary and pancreas. A number of different technical approaches for the detection and quantification of proteins in serum, urine or semen are well known in the art.

Because 36P6D5 is a secreted protein expressed in cancers of the prostate, kidney, bladder, breast, colon, ovary, pancreas, and possibly other cancers, assays for detecting and quantifying 36P6D5 in blood or serum are expected to be useful for the detection, diagnosis, prognosis, and/or staging of a 36P6D5 expressing tumor in an individual. For example, 36P6D5 expression in normal tissues is found predominantly in pancreas (FIG. 3), with lower levels of expression detected in prostate and small intestine. However, high level expression is detected in xenografts derived from prostate cancer as well as cell lines derived from cancers of the breast, colon, pancreas and ovary (FIG. 4). Accordingly, detection of serum 36P6D5 may provide an indication of the presence of a prostate, breast, colon, ovarian or pancreatic tumor. Diagnosis of cancer may be made on the basis of this information and/or other information. In respect of prostate cancer, for example, such other information may include serum PSA measurements, DRE and/or ultrasonography. Further, the level of 36P6D5 detected in the serum may provide information useful in staging or prognosis. For example, as supported by the data presented in FIGS. 9 and 10, as cell populations expand and growth through the stroma and microvasculature, higher levels of 36P6D5 are expected to be observed in serum. In this context, very high levels of 36P6D5 protein in serum may suggest larger and/or more aggressive tumors.

In addition, peripheral blood and bone marrow may be conveniently assayed for the presence of 36P6D5 protein and/or 36P6D5 expressing cancer cells, including but not limited to prostate, bladder, colon, pancreatic, kidney and ovarian cancers, using RT-PCR to detect 36P6D5 expression. The presence of RT-PCR amplifiable 36P6D5 mRNA provides an indication of the presence of the cancer. RT-PCR detection assays for tumor cells in peripheral blood are currently being evaluated for use in the diagnosis and management of a number of human solid tumors. In the prostate cancer field, these include RT-PCR assays for the detection of cells expressing PSA and PSM (Verkaik et al., 1997, Urol. Res. 25: 373-384; Ghossein et al., 1995, J. Clin. Oncol. 13: 1195-2000; Heston et al., 1995, Clin. Chem. 41: 1687-1688). RT-PCR assays are well known in the art.

In one embodiment, a capture ELISA is used to detect and quantify 36P6D5 in serum, urine or semen. A capture ELISA for 36P6D5 comprises, generally, at least two monoclonal antibodies of different isotypes that recognize distinct epitopes of the 36P6D5 protein, or one anti-36P6D5 monoclonal antibody and a specific polyclonal serum derived from a different species (e.g., rabbit, goat, sheep, hamster, etc.). In this assay, one reagent serves as the capture (or coating) antibody and the other as the detection antibody. As shown in Table 2, clinical serum samples from and pancreatic cancer patients, and normal male donors were screened for 36P6D5 protein using a capture ELISA as described above and in FIG. 10. Supernatants from PC-3-36P6D5 and Du4475 cells, and from PC-3-neo cells, served as positive and negative controls, respectively for 36P6D5 protein detection. ND: not detected or below detection sensitivity. 36P6D5 protein was detected in 7/10 colon cancer patients and 6/10 pancreatic cancer patients, one of which had relatively high levels (29.70 ng/ml), but only in 1/6 normal male donors. In a related embodiment, FACS analysis is used for the detection of cells expressing 36P6D5 protein, for example those that have escaped the local site of disease and have migrated to other sites such as the lymphatic system.

As discussed in detail below, levels of 36P6D5 including 36P6D5 serum levels may be used to provide an indication of the presence, extent and aggressiveness of a 36P6D5 expressing tumor. As noted, above 36P6D5 shares a number of characteristics with PSA which is the most important, accurate, and clinically useful biochemical marker in the prostate. Any process that disrupts the normal architecture of the prostate allows diffusion of PSA into the stroma and microvasculature. Consequently, clinically important increases in serum prostate-specific antigen levels are seen with prostatic cancers. In particular, the greater number of malignant cells and the stromal disruption associated with cancer account for the increased serum prostate-specific antigen level. In this context, serum prostate-specific antigen levels correlate positively with clinical stage, tumor volume, histologic grade, and the presence of capsular perforation and seminal vesicle invasion. See e.g. Bostwick, D. G. Am. J. Clin. Pathol. 102 (4 Suppl 1): S31-S37 (1994).

Using PSA as an analogous molecule, is likely that because 36P6D5 is also a secreted molecule that exhibits a restricted pattern of tissue expression (including the prostate), the increasing load of malignant cells and the stromal disruption that occurs with cancer will make the serum 36P6D5 antigen levels correlate positively with one or more clinically relevant factors such as clinical stage, tumor volume, histologic grade, and the presence of capsular perforation and seminal vesicle invasion. Serum 36P6D5 measurements over time would be expected to provide further information, wherein an increase in 36P6D5 would be expected to reflect progression and the rate of the increase would be expected to correlate with aggressiveness. Similarly, a decline in serum 36P6D5 would be expected to reflect a slower growing or regressing tumor. The identification of 36P6D5 in serum may be useful to detect tumor initiation and early stage disease. In patients who have undergone surgery or therapy, serum 36P6D5 levels would be useful for monitoring treatment response and potential recurrence.

Monitoring the Status of 36P6D5 and its Products

Assays that evaluate the status of the 36P6D5 gene and 36P6D5 gene products in an individual may provide information on the growth or oncogenic potential of a biological sample from this individual. For example, because 36P6D5 mRNA is so highly expressed in prostate cancers as compared to normal prostate tissue, assays that evaluate the relative levels of 36P6D5 mRNA transcripts or proteins in a biological sample may be used to diagnose a disease associated with 36P6D5 dysregulation such as cancer and may provide prognostic information useful in defining appropriate therapeutic options.

Because 36P6D5 is expressed, for example, in various prostate cancer xenograft tissues and cancer cell lines, and cancer patient samples, the expression status of 36P6D5 can provide information useful for determining information including the presence, stage and location of displasic, precancerous and cancerous cells, predicting susceptibility to various stages of disease, and/or for gauging tumor aggressiveness. Moreover, the expression profile makes it a potential imaging reagent for metastasized disease. Consequently, an important aspect of the invention is directed to the various molecular prognostic and diagnostic methods for examining the status of 36P6D5 in biological samples such as those from individuals suffering from, or suspected of suffering from a pathology characterized by dysregulated cellular growth such as cancer.

Oncogenesis is known to be a multistep process where cellular growth becomes progressively dysregulated and cells progress from a normal physiological state to precancerous and then cancerous states (see e.g. Alers et al., Lab Invest. 77(5): 437-438 (1997) and Isaacs et al., Cancer Surv. 23: 19-32 (1995)). In this context, examining a biological sample for evidence of dysregulated cell growth (such as aberrant 36P6D5 expression in prostate cancers) can allow the early detection of such aberrant cellular physiology before a pathology such as cancer has progressed to a stage at which therapeutic options are more limited. In such examinations, the status of 36P6D5 in a biological sample of interest (such as one suspected of having dysregulated cell growth) can be compared, for example, to the status of 36P6D5 in a corresponding normal sample (e.g. a sample from that individual (or alternatively another individual) that is not effected by a pathology, for example one not suspected of having dysregulated cell growth) with alterations in the status of 36P6D5 in the biological sample of interest (as compared to the normal sample) providing evidence of dysregulated cellular growth. In addition to using a biological sample that is not effected by a pathology as a normal sample, one can also use a predetermined normative value such as a predetermined normal level of mRNA expression (see e.g. Grever et al., J. Comp. Neurol. 1996 Dec. 9; 376(2):306-14 and U.S. Pat. No. 5,837,501) to compare 36P6D5 in normal versus suspect samples.

The term "status" in this context is used according to its art accepted meaning and refers to the condition or state of a gene and its products. As specifically described herein, the status of 36P6D5 can be evaluated by a number of parameters known in the art. Typically an alteration in the status of 36P6D5 comprises a change in the location of 36P6D5 expressing cells and/or an increase in 36P6D5 mRNA and/or protein expression.

Typically, skilled artisans use a number of parameters to evaluate the condition or state of a gene and its products. These include, but are not limited to the location of expressed gene products (including the location of 36P6D5 expressing cells) as well as the, level, and biological activity of expressed gene products (such as 36P6D5 mRNA polynucleotides and polypeptides). Alterations in the status of 36P6D5 can be evaluated by a wide variety of methodologies well known in the art, typically those discussed below. Typically an alteration in the status of 36P6D5 comprises a change in the location of 36P6D5 and/or 36P6D5 expressing cells and/or an increase in 36P6D5 mRNA and/or protein expression.

As discussed in detail herein, in order to identify a condition or phenomenon associated with dysregulated cell growth, the status of 36P6D5 in a biological sample may be evaluated by a number of methods utilized by skilled artisans including, but not limited to genomic Southern analysis (to examine, for example perturbations in the 36P6D5 gene), northerns and/or PCR analysis of 36P6D5 mRNA (to examine, for example alterations in the polynucleotide sequences or expression levels of 36P6D5 mRNAs), and western and/or immunohistochemical analysis (to examine, for example alterations in polypeptide sequences, alterations in polypeptide localization within a sample, alterations in expression levels of 36P6D5 proteins and/or associations of 36P6D5 proteins with polypeptide binding partners). Detectable 36P6D5 polynucleotides include, for example, a 36P6D5 gene or fragments thereof, 36P6D5 mRNA, alternative splice variants 36P6D5 mRNAs, and recombinant DNA or RNA molecules containing a 36P6D5 polynucleotide.

The expression profile of 36P6D5 makes it a potential diagnostic marker for local and/or metastasized disease. In particular, the status of 36P6D5 may provide information useful for predicting susceptibility to particular disease stages, progression, and/or tumor aggressiveness. The invention provides methods and assays for determining 36P6D5 status and diagnosing cancers that express 36P6D5, such as cancers of the prostate, bladder, bladder, kidney, ovaries, breast, pancreas, colon and lung. 36P6D5 status in patient samples may be analyzed by a number of means well known in the art, including without limitation, immunohistochemical analysis, in situ hybridization, RT-PCR analysis on laser capture micro-dissected samples, western blot analysis of clinical samples and cell lines, and tissue array analysis. Typical protocols for evaluating the status of the 36P6D5 gene and gene products can be found, for example in Ausubul et al. eds., 1995, Current Protocols In Molecular Biology, Units 2 [Northern Blotting], 4 [Southern Blotting], 15 [Immunoblotting] and 18 [PCR Analysis].

As described above, the status of 36P6D5 in a biological sample can be examined by a number of well known procedures in the art. For example, the status of 36P6D5 in a biological sample taken from a specific location in the body can be examined by evaluating the sample for the presence or absence of 36P6D5 expressing cells (e.g. those that express 36P6D5 mRNAs or proteins). This examination can provide evidence of dysregulated cellular growth for example, when 36P6D5 expressing cells are found in a biological sample that does not normally contain such cells (such as a lymph node). Such alterations in the status of 36P6D5 in a biological sample are often associated with dysregulated cellular growth. Specifically, one indicator of dysregulated cellular growth is the metastases of cancer cells from an organ of origin (such as the bladder, kidney or prostate gland) to a different area of the body (such as a lymph node). In this context, evidence of dysregulated cellular growth is important for example because occult lymph node metastases can be detected in a substantial proportion of patients with prostate cancer, and such metastases are associated with known predictors of disease progression (see e.g. J Urol 1995 August; 154(2 Pt 1):474-8).

In one aspect, the invention provides methods for monitoring 36P6D5 gene products by determining the status of 36P6D5 gene products expressed by cells in a test tissue sample from an individual suspected of having a disease associated with dysregulated cell growth (such as hyperplasia or cancer) and then comparing the status so determined to the status of 36P6D5 gene products in a corresponding normal sample, the presence of aberrant 36P6D5 gene products in the test sample relative to the normal sample providing an indication of the presence of dysregulated cell growth within the cells of the individual.

In another aspect, the invention provides assays useful in determining the presence of cancer in an individual, comprising detecting a significant increase in 36P6D5 mRNA or protein expression in a test cell or tissue sample relative to expression levels in the corresponding normal cell or tissue. The presence of 36P6D5 mRNA may, for example, be evaluated in tissue samples including but not limited to prostate, kidney, bladder, ovarian, breast, pancreas, colon and lung issues (see e.g. FIGS. 4, 6 and 7). The presence of significant 36P6D5 expression in any of these tissues may be useful to indicate the emergence, presence and/or severity of these cancers, since the corresponding normal tissues do not express 36P6D5 mRNA or express it at lower levels.

In a related embodiment, 36P6D5 status may be determined at the protein level rather than at the nucleic acid level. For example, such a method or assay would comprise determining the level of 36P6D5 protein expressed by cells in a test tissue sample and comparing the level so determined to the level of 36P6D5 expressed in a corresponding normal sample. In one embodiment, the presence of 36P6D5 protein is evaluated, for example, using immunohistochemical methods. 36P6D5 antibodies or binding partners capable of detecting 36P6D5 protein expression may be used in a variety of assay formats well known in the art for this purpose.

In other related embodiments, one can evaluate the integrity 36P6D5 nucleotide and amino acid sequences in a biological sample in order to identify perturbations in the structure of these molecules such as insertions, deletions, substitutions and the like. Such embodiments are useful because perturbations in the nucleotide and amino acid sequences are observed in a large number of proteins associated with a growth dysregulated phenotype (see, e.g., Marrogi et al., 1999, J. Cutan. Pathol. 26(8):369-378). In this context, a wide variety of assays for observing perturbations in nucleotide and amino acid sequences are well known in the art. For example, the size and structure of nucleic acid or amino acid sequences of 36P6D5 gene products may be observed by the Northern, Southern, Western, PCR and DNA sequencing protocols discussed herein. In addition, other methods for observing perturbations in nucleotide and amino acid sequences such as single strand conformation polymorphism analysis are well known in the art (see, e.g., U.S. Pat. Nos. 5,382,510 and 5,952,170).

In another embodiment, one can examine the methylation status of the 36P6D5 gene in a biological sample. Aberrant demethylation and/or hypermethylation of CpG islands in gene 5' regulatory regions frequently occurs in immortalized and transformed cells and can result in altered expression of various genes. For example, promoter hypermethylation of the pi-class glutathione S-transferase (a protein expressed in normal prostate but not expressed in >90% of prostate carcinomas) appears to permanently silence transcription of this gene and is the most frequently detected genomic alteration in prostate carcinomas (De Marzo et al., Am. J. Pathol. 155(6): 1985-1992 (1999)). In addition, this alteration is present in at least 70% of cases of high-grade prostatic intraepithelial neoplasia (PIN) (Brooks et al, Cancer Epidemiol. Biomarkers Prev., 1998, 7:531-536). In another example, expression of the LAGE-I tumor specific gene (which is not expressed in normal prostate but is expressed in 25-50% of prostate cancers) is induced by deoxy-azacytidine in lymphoblastoid cells, suggesting that tumoral expression is due to demethylation (Lethe et al., Int. J. Cancer 76(6): 903-908 (1998)). In this context, a variety of assays for examining methylation status, of a gene are well known in the art. For example, one can utilize in Southern hybridization approaches methylation-sensitive restriction enzymes which can not cleave sequences that contain methylated CpG sites in order to assess the overall methylation status of CpG islands. In addition, MSP (methylation specific PCR) can rapidly profile the methylation status of all the CpG sites present in a CpG island of a given gene. This procedure involves initial modification of DNA by sodium bisulfite (which will convert all unmethylated cytosines to uracil) followed by amplification using primers specific for methylated versus unmethylated DNA. Protocols involving methylation interference can also be found for example in Current Protocols In Molecular Biology, Units 12, Frederick M. Ausubul et al. eds., 1995.

Gene amplification provides an additional method of assessing the status of 36P6D5, a locus that maps to 21q22.2-22.3, a region shown to be perturbed in a variety of cancers. Gene amplification may be measured in a sample directly, for example, by conventional Southern blotting, Northern blotting to quantitate the transcription of mRNA (Thomas, 1980, Proc. Natl. Acad. Sci. USA, 77:5201-5205), dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

In addition to the tissues discussed above, biopsied tissue or peripheral blood or bone marrow may be conveniently assayed for the presence of cancer cells, including but not limited to prostate, kidney, bladder, ovarian, breast, pancreas, colon and lung cancers using for example, Northern, dot blot or RT-PCR analysis to detect 36P6D5 expression (see e.g. FIGS. 4, 6 and 7). The presence of RT-PCR amplifiable 36P6D5 mRNA provides an indication of the presence of the cancer. RT-PCR detection assays for tumor cells in peripheral blood are currently being evaluated for use in the diagnosis and management of a number of human solid tumors. In the prostate cancer field, these include RT-PCR assays for the detection of cells expressing PSA and PSM (Verkaik et al, 1997, Urol. Res. 25:373-384; Ghossein et al., 1995, J. Clin. Oncol. 13:1195-2000; Heston et al., 1995, Clin. Chem. 41:1687-1688). RT-PCR assays are well known in the art.

A related aspect of the invention is directed to predicting susceptibility to developing cancer in an individual. In one embodiment, a method for predicting susceptibility to cancer comprises detecting 36P6D5 mRNA or 36P6D5 protein in a tissue sample, its presence indicating susceptibility to cancer, wherein the degree of 36P6D5 mRNA expression present is proportional to the degree of susceptibility. In a specific embodiment, the presence of 36P6D5 in prostate tissue is examined, with the presence of 36P6D5 in the sample providing an indication of prostate cancer susceptibility (or the emergence or existence of a prostate tumor). In another specific embodiment, the presence of 36P6D5 in tissue is examined, with the presence of 36P6D5 in the sample providing an indication of cancer susceptibility (or the emergence or existence of a tumor). In a closely related embodiment, one can evaluate the integrity 36P6D5 nucleotide and amino acid sequences in a biological sample in order to identify perturbations in the structure of these molecules such as insertions, deletions, substitutions and the like, with the presence of one or more perturbations in 36P6D5 gene products in the sample providing an indication of cancer susceptibility (or the emergence or existence of a tumor).

Yet another related aspect of the invention is directed to methods for gauging tumor aggressiveness. In one embodiment, a method for gauging aggressiveness of a tumor comprises determining the level of 36P6D5 mRNA or 36P6D5 protein expressed by cells in a sample of the tumor, comparing the level so determined to the level of 36P6D5 mRNA or 36P6D5 protein expressed in a corresponding normal tissue taken from the same individual or a normal tissue reference sample, wherein the degree of 36P6D5 mRNA or 36P6D5 protein expression in the tumor sample relative to the normal sample indicates the degree of aggressiveness. In a specific embodiment, aggressiveness of a tumor is evaluated by determining the extent to which 36P6D5 is expressed in the tumor cells, with higher expression levels indicating more aggressive tumors. In a closely related embodiment, one can evaluate the integrity of 36P6D5 nucleotide and amino acid sequences in a biological sample in order to identify perturbations in the structure of these molecules such as insertions, deletions, substitutions and the like, with the presence of one or more perturbations indicating more aggressive tumors.

The invention additionally provides methods of examining a biological sample for evidence of dysregulated cellular growth. In one embodiment, the method comprises comparing the status of 36P6D5 in the biological sample to the status of 36P6D5 in a corresponding normal sample, wherein alterations in the status of 36P6D5 in the biological sample are associated with dysregulated cellular growth. The status of 36P6D5 in the biological sample can be evaluated by, for example, examining levels of 36P6D5 mRNA expression or levels of 36P6D5 protein expression. In one embodiment, an alteration in the status of 36P6D5 is identified by the presence of 36P6D5 expressing cells in a biological sample from a tissue in which 36P6D5 expressing cells are normally absent.

In another aspect, the invention provides assays useful in determining the presence of cancer in an individual, comprising detecting a significant increase in 36P6D5 mRNA or protein expression in a test cell or tissue sample relative to expression levels in the corresponding normal cell or tissue. The presence of 36P6D5 mRNA may, for example, be evaluated in tissue samples including but not limited to colon, lung, prostate, pancreas, bladder, breast, ovary, cervix, testis, head and neck, brain, stomach, bone, etc. The presence of significant 36P6D5 expression in any of these tissues may be useful to indicate the emergence, presence and/or severity of these cancers or a metastasis of cancer originating in another tissue, since the corresponding normal tissues do not express 36P6D5 mRNA or express it at lower levels.

Yet another related aspect of the invention is directed to methods for observing the progression of a malignancy in an individual over time. In one embodiment, methods for observing the progression of a malignancy in an individual over time comprise determining the level of 36P6D5 mRNA or 36P6D5 protein expressed by cells in a sample of the tumor, comparing the level so determined to the level of 36P6D5 mRNA or 36P6D5 protein expressed in an equivalent tissue sample taken from the same individual at a different time, wherein the degree of 36P6D5 mRNA or 36P6D5 protein expression in the tumor sample over time provides information on the progression of the cancer. In a specific embodiment, the progression of a cancer is evaluated by determining the extent to which 36P6D5 expression in the tumor cells alters over time, with higher expression levels indicating a progression of the cancer. In a closely related embodiment, one can evaluate the integrity 36P6D5 nucleotide and amino acid sequences in a biological sample in order to identify perturbations in the structure of these molecules such as insertions, deletions, substitutions and the like, with the presence of one or more perturbations indicating a progression of the cancer.

The above diagnostic approaches may be combined with any one of a wide variety of prognostic and diagnostic protocols known in the art. For example, another embodiment of the invention disclosed herein is directed to methods for observing a coincidence between the expression of 36P6D5 gene and 36P6D5 gene products (or perturbations in 36P6D5 gene and 36P6D5 gene products) and a factor that is associated with malignancy as a means of diagnosing and prognosticating the status of a tissue sample. In this context, a wide variety of factors associated with malignancy may be utilized such as the expression of genes otherwise associated with malignancy (including PSA, PSCA and PSM expression) as well as gross cytological observations (see e.g. Bocking et al., 1984, Anal. Quant. Cytol. 6(2):74-88; Eptsein, 1995, Hum. Pathol. 26(2):223-9; Thorson et al., 1998, Mod. Pathol. 11(6):

543-51; Baisden et al., 1999, Am. J. Surg. Pathol. 23(8):918-24). Methods for observing a coincidence between the expression of 36P6D5 gene and 36P6D5 gene products (or perturbations in 36P6D5 gene and 36P6D5 gene products) and an additional factor that is associated with malignancy are useful for example, because the presence of a set or constellation of specific factors that coincide provides information crucial for diagnosing and prognosticating the status of a tissue sample.

In a typical embodiment, methods for observing a coincidence between the expression of 36P6D5 gene and 36P6D5 gene products (or perturbations in 36P6D5 gene and 36P6D5 gene products) and a factor that is associated with malignancy entails detecting the overexpression of 36P6D5 mRNA or protein in a tissue sample, detecting the overexpression of PSA mRNA or protein in a tissue sample, and observing a coincidence of 36P6D5 mRNA or protein and PSA mRNA or protein overexpression. In a specific embodiment, the expression of 36P6D5 and PSA mRNA in prostate tissue is examined. In a preferred embodiment, the coincidence of 36P6D5 and PSA mRNA overexpression in the sample provides an indication of prostate cancer, prostate cancer susceptibility or the emergence or existence of a prostate tumor.

Methods for detecting and quantifying the expression of 36P6D5 mRNA or protein are described herein and use of standard nucleic acid and protein detection and quantification technologies is well known in the art. Standard methods for the detection and quantification of 36P6D5 mRNA include in situ hybridization using labeled 36P6D5 riboprobes, Northern blot and related techniques using 36P6D5 polynucleotide probes, RT-PCR analysis using primers specific for 36P6D5, and other amplification type detection methods, such as, for example, branched DNA, SISBA, TMA and the like. In a specific embodiment, semi-quantitative RT-PCR may be used to detect and quantify 36P6D5 mRNA expression as described in the Examples that follow. Any number of primers capable of amplifying 36P6D5 may be used for this purpose, including but not limited to the various primer sets specifically described herein. Standard methods for the detection and quantification of protein may be used for this purpose. In a specific embodiment, polyclonal or monoclonal antibodies specifically reactive with the wild-type 36P6D5 protein may be used in an immunohistochemical assay of biopsied tissue.

Identifying Molecules that Interact with 36P6D5

The 36P6D5 protein sequences disclosed herein allow the skilled artisan to identify proteins, small molecules and other agents that interact with 36P6D5 and pathways activated by 36P6D5 via any one of a variety of art accepted protocols. For example one can utilize one of the variety of so-called interaction trap systems (also referred to as the "two-hybrid assay"). In such systems, molecules that interact reconstitute a transcription factor and direct expression of a reporter gene, the expression of which is then assayed. Typical systems identify protein-protein interactions in vivo through reconstitution of a eukaryotic transcriptional activator and are disclosed for example in U.S. Pat. Nos. 5,955,280, 5,925,523, 5,846,722 and 6,004,746.

Alternatively one can identify molecules that interact with 36P6D5 protein sequences by screening peptide libraries. In such methods, peptides that bind to selected receptor molecules such as 36P6D5 are identified by screening libraries that encode a random or controlled collection of amino acids. Peptides encoded by the libraries are expressed as fusion proteins of bacteriophage coat proteins, and bacteriophage particles are then screened against the receptors of interest.

Peptides having a wide variety of uses, such as therapeutic or diagnostic reagents, may thus be identified without any prior information on the structure of the expected ligand or receptor molecule. Typical peptide libraries and screening methods that can be used to identify molecules that interact with 36P6D5 protein sequences are disclosed for example in U.S. Pat. Nos. 5,723,286 and 5,733,731.

Alternatively, cell lines expressing 36P6D5 can be used to identify protein-protein interactions mediated by 36P6D5. This possibility can be examined using immunoprecipitation techniques as shown by others (Hamilton B J, et al. Biochem. Biophys. Res. Commun. 1999, 261:646-51). Typically 36P6D5 protein can be immunoprecipitated from 36P6D5 expressing prostate cancer cell lines using anti-36P6D5 antibodies. Alternatively, antibodies against His-tag can be used in a cell line engineered to express 36P6D5 (vectors mentioned above). The immunoprecipitated complex can be examined for protein association by procedures such as western blotting, $^{35}$S-methionine labeling of proteins, protein microsequencing, silver staining and two dimensional gel electrophoresis.

Small molecules that interact with 36P6D5 can be identified through related embodiments of such screening assays. For example, small molecules can be identified that interfere with protein function, including molecules that interfere with 36P6D5's ability to mediate phosphorylation and de-phosphorylation, second messenger signaling and tumorigenesis. Typical methods are discussed for example in U.S. Pat. No. 5,928,868 and include methods forming hybrid ligands in which at least one ligand is a small molecule. In an illustrative embodiment, the hybrid ligand is introduced into cells that in turn contain a first and a second expression vector. Each expression vector includes DNA for expressing a hybrid protein that encodes a target protein linked to a coding sequence for a transcriptional module. The cells further contains a reporter gene, the expression of which is conditioned on the proximity of the first and second hybrid proteins to each other, an event that occurs only if the hybrid ligand binds to target sites on both hybrid proteins. Those cells that express the reporter gene are selected and the unknown small molecule or the unknown hybrid protein is identified.

A typical embodiment of this invention consists of a method of screening for a molecule that interacts with a 36P6D5 amino acid sequence shown in FIG. 1 (SEQ ID NO: 2), comprising the steps of contacting a population of molecules with the 36P6D5 amino acid sequence, allowing the population of molecules and the 36P6D5 amino acid sequence to interact under conditions that facilitate an interaction, determining the presence of a molecule that interacts with the 36P6D5 amino acid sequence and then separating molecules that do not interact with the 36P6D5 amino acid sequence from molecules that do interact with the 36P6D5 amino acid sequence. In a specific embodiment, the method further includes purifying a molecule that interacts with the 36P6D5 amino acid sequence. In a preferred embodiment, the 36P6D5 amino acid sequence is contacted with a library of peptides.

Using 36P6D5 to Modulate Cellular Microenvironments

A variety of secreted proteins have been described in prostate cancer, a number of which have been shown to participate in the process of tumor formation and progression (Inoue K Clin Cancer Res. 2000; 6:2104-19, Dow J K, deVere White R W. Urology. 2000; 55:800-6). In the process of tumor progression, cancer cells to secrete and express molecules that allow them to grow in both the microenvironment of the local prostate as well as the bone microenvironment. A unique feature of prostate cancer is that in the process of tumor progression, cancer cells become metastatic to bone and recent studies suggest that this predilection to metastasize to the bone is based on the ability of prostate cancer cells to secrete and express molecules that allow them to grow in the bone microenvironment (Koeneman K S, Yeung F, Chung L W. Prostate 1999: 39:246). In this context, the data presented herein (see e.g. FIGS. 8 and 9) suggests that 36P6D5 plays a role (1) in targeting prostate cells to the bone, (2) allowing the growth of prostate cells in the bone microenvironment, (3) inducing the differentiation of prostate tumor cells or bone marrow cells to osteoblasts or (4) supporting the interaction of bone stroma with prostate cancer cells thereby creating a favorable environment for the growth of cancer cells. Consequently, this molecule can be used in methods for conditioning media and/or mimicking the microenvironment in which prostate cancer cells can metastasize.

Figure 8:
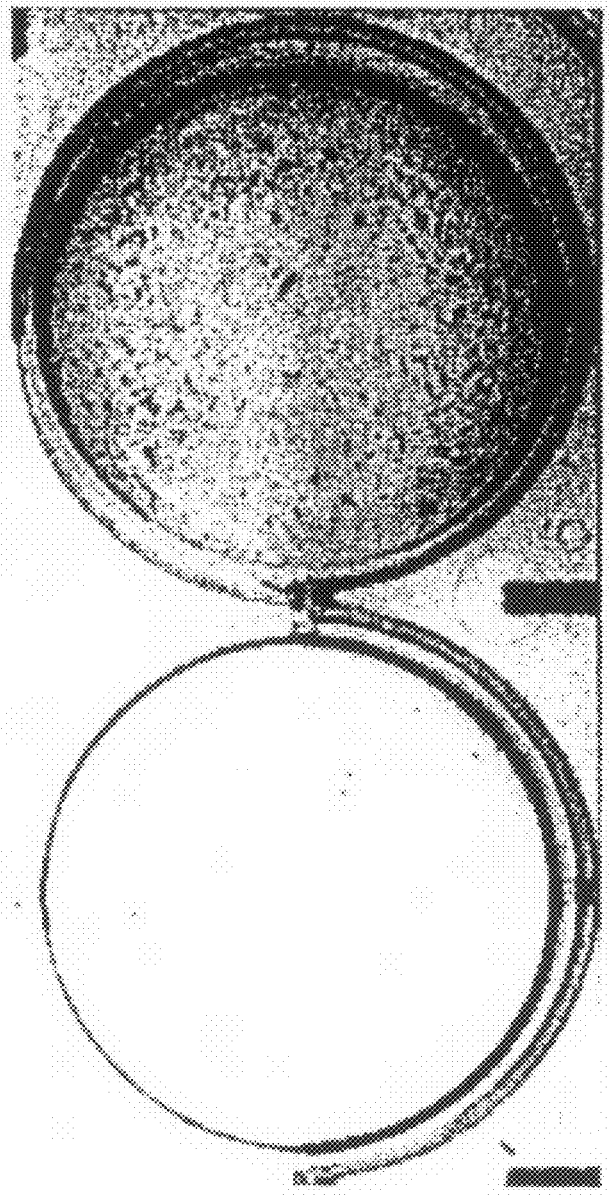
FIG. 8. Binding of 36P6D5 to LAPC9 AD. A single cell suspension of LAPC9 AD xenograft cells were allowed to adhere overnight to a 6 well plate. The cells were incubated in the presence of control or 36P6D5-AP fusion protein. The alkaline phosphate substrate, BM purple, was used for detection.

In order to test the possibility that 36P6D5 interacts with cells normally located in the prostate and bone microenvironments, the 36P6D5 protein was expressed as a recombinant protein (pTag5 36P6D5). Purified recombinant-36P6D5 was then incubated with a variety of relevant cell types, including prostate epithelial cells, prostate tumor cell lines, prostate stromal cells, osteosarcoma and bone stromal cells. Binding of 36P6D5 to intact cells is detected by FACS analysis and by calorimetric assay. Our studies indicated that, when the recombinant 36P6D5 AP-fusion protein is incubated in the presence of prostate cancer cells derived from LAPC4 and LAPC9 xenografts, it binds to LAPC9 and LAPC4 xenograft cells. Binding of 36P6D5 to the cell surface was detected using calorimetric change in AP substrate (FIG. 8). In contrast, no color conversion was observed when cells were incubated with the appropriate control. This analysis is valuable as it identifies a cell population that binds and may respond to 36P6D5. In addition, the identification of a target cell population may provide a means of isolating and identifying 36P6D5 receptors. This information can be used in a variety of therapeutic application and small molecule design.

Using the data presented herein (see e.g. FIG. 8), one can employ methods to modulate cancer cell phenotypes and dissect the different stages of metastasis by reproducing the microenvironment of the local prostate in which cancer cells originate as well metastatic cellular microenvironment, thereby generating a cancer model in which artisans can assess novel therapeutic and diagnostic compositions and methods. An illustrative method consists of modulating the microenvironment of a cell by exposing the cell to a 36P6D5 polypeptide so that the polypeptide binds to the cell, thereby modulating the microenvironment of the cell. A related method in this context consists of modulating the microenvironment of a cell by exposing the cell to a molecule that interacts with a 36P6D5 polypeptide (such as an anti-36P6D5 antibody) that inhibits or facilitates the binding of the polypeptide to the cell, thereby modulating the microenvironment of the cell. Such methods for generating or modulating a specific microenvironmental milieu satisfy a need in the art to generate a variety diverse microenvironments based on observations that cancer cells (including prostate cancer cells) are differentially regulated depending upon the factors present in the cell microenvironment (see e.g. Levesque et al., Endocrinology 139(5): 2375-2381 (1998). Consequently the identification 36P6D5 proteins as molecules which are both secreted by and bind to cells in this microenvironment allows the skilled artisan to use this information to include and/or manipulate 36P6D in contexts that more faithfully reproduce and modulate the events occurring in the progression of cancers.

A number of experiments can designed to investigate how 36P6D5 may contribute to the growth of prostate cancer cells. In a first typical set of experiments, prostate cancer epithelial cells are incubated in the presence or absence of recombinant 36P6D5, and evaluated for proliferation using a well-documented calorimetric assay. In parallel, PC3 cells engineered to stably express 36P6D5 are evaluated for cell growth potential. In a second typical set of experiments, tagged prostate cancer cells, such as PC3 cells engineered to express the Green Fluorescence Protein (GFP), are grown in the presence of bone stromal cells. The cells are incubated in the presence or absence of recombinant 36P6D5, and evaluated for cell growth by measuring increase in GFP.

Using the disclosure provided herein, it is possible to examine the role of 36P6D5 in bone metastasis. In order to determine whether 36P6D5 induces prostate cells to become osteomimetic, primary prostate cells as well as cell lines can be grown in the presence or absence of recombinant purified 36P6D5. Cells can be then examined for the expression of early and late markers of bone maturation, including osteonectin, osteopontin, alkaline phosphatase and osteocalcin. One can also determine whether 36P6D5 is inducing the expression of growth factors supportive of prostate cell growth in a traditionally protective microenvironment such as the bone. PCR and ELISA techniques can be used to investigate the expression and secretion of FGF, HGF and IGF in cells grown in the presence or absence of recombinant purified 36P6D5. Similar experiments can be performed using bone marrow cells to determine whether 36P6D5 induces the differentiation of chondrocyte progenitors to mature osteocytes. These experiments may be valuable in demonstrating the role of 36P6D5 in supporting the creation of an environment favorable for prostate cancer growth in bone, and identifying targets for therapeutic intervention.

Using the disclosure provided herein, it is possible to examine the role of 36P6D5 in Cell-Cell Interaction. It is possible that 36P6D5 plays a role in recruiting prostate cells to the bone by enhancing prostate cell interaction with stromal cells or osteocytes. GFP expressing prostate cancer cells can be grown in the presence or absence of recombinant 36P6D5 protein. GPF cells can be incubated with control or 36P6D5 treated stromal cells and osteocytes for various amounts of time. Non-adherent cells can be removed and adhesion to stroma and osteocytes can be evaluated by measuring the amount of GFP in the culture. This data will be critical in considering inhibitors of factors which modulate the microenvironment of the local prostate in which cancer cells originate and grow as the colonization of metastatic sites by cancer cells.

Therapeutic Methods and Compositions

The identification of 36P6D5 as a gene that is highly expressed in cancers of the prostate (and possibly other cancers), opens a number of therapeutic approaches to the treatment of such cancers. As discussed above, it is possible that 36P6D5 is secreted from cancer cells and in this way modulates proliferation signals. Its potential role as a transcription factor and its high expression in prostate cancer makes it a potential target for small molecule-mediated therapy.

Accordingly, therapeutic approaches aimed at inhibiting the activity of the 36P6D5 protein are expected to be useful for patients suffering from prostate cancer and other cancers expressing 36P6D5. These therapeutic approaches aimed at inhibiting the activity of the 36P6D5 protein generally fall into two classes. One class comprises various methods for inhibiting the binding or association of the 36P6D5 protein with its binding partner or with other proteins. Another class comprises a variety of methods for inhibiting the transcription of the 36P6D5 gene or translation of 36P6D5 mRNA.

36P6D5 as a Target for Antibody-Based Therapy

The structural features of 36P6D5 indicate that this molecule is an attractive target for antibody-based therapeutic strategies. A number of typical antibody strategies are known in the art for targeting both extracellular and intracellular molecules (see e.g. complement and ADCC mediated killing as well as the use of intrabodies discussed below). Because 36P6D5 is expressed by cancer cells of various lineages and not by corresponding normal cells, systemic administration of 36P6D5-immunoreactive compositions would be expected to exhibit excellent sensitivity without toxic, non-specific and/or non-target effects caused by binding of the immunotherapeutic molecule to non-target organs and tissues. Antibodies specifically reactive with domains of 36P6D5 can be useful to treat 36P6D5-expressing cancers systemically, either as conjugates with a toxin or therapeutic agent, or as naked antibodies capable of inhibiting cell proliferation or function.

36P6D5 antibodies can be introduced into a patient such that the antibody binds to 36P6D5 and modulates or perturbs a function such as an interaction with a binding partner and consequently mediates the growth inhibition and/or destruction of the cells and the tumor and/or inhibits the growth of the cells or the tumor. Mechanisms by which such antibodies exert a therapeutic effect may include complement-mediated cytolysis, antibody-dependent cellular cytotoxicity, modulating the physiological function of 36P6D5, inhibiting ligand binding or signal transduction pathways, modulating tumor cell differentiation, altering tumor angiogenesis factor profiles, and/or by inducing apoptosis. 36P6D5 antibodies can be conjugated to toxic or therapeutic agents and used to deliver the toxic or therapeutic agent directly to 36P6D5-bearing tumor cells. Examples of toxic agents include, but are not limited to, calchemicin, maytansinoids, radioisotopes such as $^{131}$I, ytrium, and bismuth.

Cancer immunotherapy using anti-36P6D5 antibodies may follow the teachings generated from various approaches that have been successfully employed in the treatment of other types of cancer, including but not limited to colon cancer (Arlen et al., 1998, Crit. Rev. Immunol. 18:133-138), multiple myeloma (Ozaki et al., 1997, Blood 90:3179-3186; Tsunenari et al., 1997, Blood 90:2437-2444), gastric cancer (Kasprzyk et al., 1992, Cancer Res. 52:2771-2776), B-cell lymphoma (Funakoshi et al., 1996, J. Immunother. Emphasis Tumor Immunol. 19:93-101), leukemia (Zhong et al., 1996, Leuk. Res. 20:581-589), colorectal cancer (Moun et al., 1994, Cancer Res. 54:6160-6166; Velders et al., 1995, Cancer Res. 55:4398-4403), and breast cancer (Shepard et al., 1991, J. Clin. Immunol. 11:117-127). Some therapeutic approaches involve conjugation of naked antibody to a toxin, such as the conjugation of $^{131}$I to anti-CD20 antibodies (e.g., Rituxan™, IDEC Pharmaceuticals Corp.), while others involve co-administration of antibodies and other therapeutic agents, such as Herceptin™ (trastuzumab) with paclitaxel (Genentech, Inc.). For treatment of prostate cancer, for example, 36P6D5 antibodies can be administered in conjunction with radiation, chemotherapy or hormone ablation.

Although 36P6D5 antibody therapy may be useful for all stages of cancer, antibody therapy may be particularly appropriate in advanced or metastatic cancers. Treatment with the antibody therapy of the invention may be indicated for patients who have received previously one or more chemotherapy, while combining the antibody therapy of the invention with a chemotherapeutic or radiation regimen may be preferred for patients who have not received chemotherapeutic treatment. Additionally, antibody therapy may enable the use of reduced dosages of concomitant chemotherapy, particularly for patients who do not tolerate the toxicity of the chemotherapeutic agent very well.

It may be desirable for some cancer patients to be evaluated for the presence and level of 36P6D5 expression, preferably using immunohistochemical assessments of tumor tissue, quantitative 36P6D5 imaging, or other techniques capable of reliably indicating the presence and degree of 36P6D5 expression. Immunohistochemical analysis of tumor biopsies or surgical specimens may be preferred for this purpose. Methods for immunohistochemical analysis of tumor tissues are well known in the art.

Anti-36P6D5 monoclonal antibodies useful in treating prostate and other cancers include those that are capable of initiating a potent immune response against the tumor and those that are capable of direct cytotoxicity. In this regard, anti-36P6D5 monoclonal antibodies (mAbs) may elicit tumor cell lysis by either complement-mediated or antibody-dependent cell cytotoxicity (ADCC) mechanisms, both of which require an intact Fc portion of the immunoglobulin molecule for interaction with effector cell Fc receptor sites or complement proteins. In addition, anti-36P6D5 mAbs that exert a direct biological effect on tumor growth are useful in the practice of the invention. Potential mechanisms by which such directly cytotoxic mAbs may act include inhibition of cell growth, modulation of cellular differentiation, modulation of tumor angiogenesis factor profiles, and the induction of apoptosis. The mechanism by which a particular anti-36P6D5 mAb exerts an anti-tumor effect may be evaluated using any number of in vitro assays designed to determine ADCC, ADMMC, complement-mediated cell lysis, and so forth, as is generally known in the art.

The use of murine or other non-human monoclonal antibodies, or human/mouse chimeric mAbs may induce moderate to strong immune responses in some patients. In some cases, this will result in clearance of the antibody from circulation and reduced efficacy. In the most severe cases, such an immune response may lead to the extensive formation of immune complexes which, potentially, can cause renal failure. Accordingly, preferred monoclonal antibodies used in the practice of the therapeutic methods of the invention are those that are either fully human or humanized and that bind specifically to the target 36P6D5 antigen with high affinity but exhibit low or no antigenicity in the patient.

Therapeutic methods of the invention contemplate the administration of single anti-36P6D5 mAbs as well as combinations, or cocktails, of different mAbs. Such mAb cocktails may have certain advantages inasmuch as they contain mAbs that target different epitopes, exploit different effector mechanisms or combine directly cytotoxic mAbs with mAbs that rely on immune effector functionality. Such mAbs in combination may exhibit synergistic therapeutic effects. In addition, the administration of anti-36P6D5 mAbs may be combined with other therapeutic agents, including but not limited to various chemotherapeutic agents, androgen-blockers, and immune modulators (e.g., IL-2, GM-CSF). The anti-36P6D5 mAbs may be administered in their "naked" or unconjugated form, or may have therapeutic agents conjugated to them.

The anti-36P6D5 antibody formulations may be administered via any route capable of delivering the antibodies to the tumor site. Potentially effective routes of administration include, but are not limited to, intravenous, intraperitoneal, intramuscular, intratumor, intradermal, and the like. Treatment will generally involve the repeated administration of the anti-36P6D5 antibody preparation via an acceptable route of administration such as intravenous injection (IV), typically at a dose in the range of about 0.1 to about 10 mg/kg body weight. Doses in the range of 10-500 mg mAb per week may be effective and well tolerated.

Based on clinical experience with the Herceptin mAb in the treatment of metastatic breast cancer, an initial loading dose of approximately 4 mg/kg patient body weight IV followed by weekly doses of about 2 mg/kg IV of the anti-36P6D5 mAb preparation may represent an acceptable dosing regimen. Preferably, the initial loading dose is administered as a 90 minute or longer infusion. The periodic maintenance dose may be administered as a 30 minute or longer infusion, provided the initial dose was well tolerated. However, as one of skill in the art will understand, various factors will influence the ideal dose regimen in a particular case. Such factors may include, for example, the binding affinity and half life of the Ab or mAbs used, the degree of 36P6D5 expression in the patient, the extent of circulating shed 36P6D5 antigen, the desired steady-state antibody concentration level, frequency of treatment, and the influence of chemotherapeutic agents used in combination with the treatment method of the invention.

Optimally, patients should be evaluated for the level of circulating shed 36P6D5 antigen in serum in order to assist in the determination of the most effective dosing regimen and related factors. Such evaluations may also be used for monitoring purposes throughout therapy, and may be useful to gauge therapeutic success in combination with evaluating other parameters (such as serum PSA levels in prostate cancer therapy).

Inhibition of 36P6D5 Protein Function

The invention includes various methods and compositions for inhibiting the binding of 36P6D5 to its binding partner or ligand, or its association with other protein(s) as well as methods for inhibiting 36P6D5 function.

Inhibition of 36P6D5 with Intracellular Antibodies

In one approach, recombinant vectors encoding single chain antibodies that specifically bind to 36P6D5 may be introduced into 36P6D5 expressing cells via gene transfer technologies, wherein the encoded single chain anti-36P6D5 antibody is expressed intracellularly, binds to 36P6D5 protein, and thereby inhibits its function. Methods for engineering such intracellular single chain antibodies are well known. Such intracellular antibodies, also known as "intrabodies", may be specifically targeted to a particular compartment within the cell, providing control over where the inhibitory activity of the treatment will be focused. This technology has been successfully applied in the art (for review, see Richardson and Marasco, 1995, TIBTECH vol. 13). Intrabodies have been shown to virtually eliminate the expression of otherwise abundant cell surface receptors. See, for example, Richardson et al., 1995, Proc. Natl. Acad. Sci. USA 92: 3137-3141; Beerli et al., 1994, J. Biol. Chem. 289: 23931-23936; Deshane et al., 1994, Gene Ther. 1: 332-337.

Single chain antibodies comprise the variable domains of the heavy and light chain joined by a flexible linker polypeptide, and are expressed as a single polypeptide. Optionally, single chain antibodies may be expressed as a single chain variable region fragment joined to the light chain constant region. Well known intracellular trafficking signals may be engineered into recombinant polynucleotide vectors encoding such single chain antibodies in order to precisely target the expressed intrabody to the desired intracellular compartment. For example, intrabodies targeted to the endoplasmic reticulum (ER) may be engineered to incorporate a leader peptide and, optionally, a C-terminal ER retention signal, such as the KDEL amino acid motif Intrabodies intended to exert activity in the nucleus may be engineered to include a nuclear localization signal. Lipid moieties may be joined to intrabodies in order to tether the intrabody to the cytosolic side of the plasma membrane. Intrabodies may also be targeted to exert function in the cytosol. For example, cytosolic intrabodies may be used to sequester factors within the cytosol, thereby preventing them from being transported to their natural cellular destination.

In one embodiment, intrabodies may be used to capture 36P6D5 in the nucleus, thereby preventing its activity within the nucleus. Nuclear targeting signals may be engineered into such 36P6D5 intrabodies in order to achieve the desired targeting. Such 36P6D5 intrabodies may be designed to bind specifically to a particular 36P6D5 domain. In another embodiment, cytosolic intrabodies that specifically bind to the 36P6D5 protein may be used to prevent 36P6D5 from gang access to the nucleus, thereby preventing it from exerting any biological activity within the nucleus (e.g., preventing 36P6D5 from forming transcription complexes with other factors).

In order to specifically direct the expression of such intrabodies to particular tumor cells, the transcription of the intrabody may be placed under the regulatory control of an appropriate tumor-specific promoter and/or enhancer. In order to target intrabody expression specifically to prostate, for example, the PSA promoter and/or promoter/enhancer may be utilized (See, for example, U.S. Pat. No. 5,919,652).

Inhibition of 36P6D5 with Recombinant Proteins

In another approach, recombinant molecules that are capable of binding to 36P6D5 thereby preventing 36P6D5 from accessing/binding to its binding partner(s) or associating with other protein(s) are used to inhibit 36P6D5 function. Such recombinant molecules may, for example, contain the reactive part(s) of a 36P6D5 specific antibody molecule. In a particular embodiment, the 36P6D5 binding domain of a 36P6D5 binding partner may be engineered into a dimeric fusion protein comprising two 36P6D5 ligand binding domains linked to the Fc portion of a human IgG, such as human IgG1. Such IgG portion may contain, for example, the $C_H2$ and $C_H3$ domains and the hinge region, but not the $C_H1$ domain. Such dimeric fusion proteins may be administered in soluble form to patients suffering from a cancer associated with the expression of 36P6D5, including but not limited to prostate, bladder, ovarian, breast, pancreas, colon and lung cancers, where the dimeric fusion protein specifically binds to 36P6D5 thereby blocking 36P6D5 interaction with a binding partner. Such dimeric fusion proteins may be further combined into multimeric proteins using known antibody linking technologies.

Inhibition of 36P6D5 Transcription or Translation

Within another class of therapeutic approaches, the invention provides various methods and compositions for inhibiting the transcription of the 36P6D5 gene. Similarly, the invention also provides methods and compositions for inhibiting the translation of 36P6D5 mRNA into protein.

In one approach, a method of inhibiting the transcription of the 36P6D5 gene comprises contacting the 36P6D5 gene with a 36P6D5 antisense polynucleotide. In another approach, a method of inhibiting 36P6D5 mRNA translation comprises contacting the 36P6D5 mRNA with an antisense polynucleotide. In another approach, a 36P6D5 specific ribozyme may be used to cleave the 36P6D5 message, thereby inhibiting translation. Such antisense and ribozyme based methods may also be directed to the regulatory regions of the 36P6D5 gene, such as the 36P6D5 start site, promoter and/or enhancer elements. Similarly, proteins capable of inhibiting a 36P6D5 gene transcription factor may be used to inhibit 36P6D5 mRNA transcription. The various polynucleotides and compositions useful in the aforementioned methods have been described above. In another approach, one can inhibit the translation of the 36P6D6 gene using morpholino antisense technology. The use of antisense and ribozyme molecules to inhibit transcription and translation is well known in the art.

Other factors that inhibit the transcription of 36P6D5 through interfering with 36P6D5 transcriptional activation may also be useful for the treatment of cancers expressing 36P6D5. Similarly, factors that are capable of interfering with 36P6D5 processing may be useful for the treatment of cancers expressing 36P6D5. Cancer treatment methods utilizing such factors are also within the scope of the invention.

General Considerations for Therapeutic Strategies

Gene transfer and gene therapy technologies may be used for delivering therapeutic polynucleotide molecules to tumor cells synthesizing 36P6D5 (i.e., antisense, ribozyme, polynucleotides encoding intrabodies and other 36P6D5 inhibitory molecules). A number of gene therapy approaches are known in the art. Recombinant vectors encoding 36P6D5 antisense polynucleotides, ribozymes, factors capable of interfering with 36P6D5 transcription, and so forth, may be delivered to target tumor cells using such gene therapy approaches.

The above therapeutic approaches may be combined with any one of a wide variety of chemotherapy or radiation therapy regimens. These therapeutic approaches may also enable the use of reduced dosages of chemotherapy and/or less frequent administration, particularly in patients that do not tolerate the toxicity of the chemotherapeutic agent well.

The anti-tumor activity of a particular composition (e.g., antisense, ribozyme, intrabody), or a combination of such compositions, may be evaluated using various in vitro and in vivo assay systems. In vitro assays for evaluating therapeutic potential include cell growth assays, soft agar assays and other assays indicative of tumor promoting activity, binding assays capable of determining the extent to which a therapeutic composition will inhibit the binding of 36P6D5 to a binding partner, etc.

In vivo, the effect of a 36P6D5 therapeutic composition may be evaluated in a suitable animal model. For example, xenogenic prostate cancer models wherein human prostate cancer explants or passaged xenograft tissues are introduced into immune compromised animals, such as nude or SCID mice, are appropriate in relation to prostate cancer and have been described (Klein et al., 1997, Nature Medicine 3:402-408). For example, PCT Patent Application WO98/16628, Sawyers et al., published Apr. 23, 1998, describes various xenograft models of human prostate cancer capable of recapitulating the development of primary tumors, micrometastasis, and the formation of osteoblastic metastases characteristic of late stage disease. Efficacy may be predicted using assays that measure inhibition of tumor formation, tumor regression or metastasis, and the like. See, also, the Examples below.

In vivo assays that qualify the promotion of apoptosis may also be useful in evaluating potential therapeutic compositions. In one embodiment, xenografts from bearing mice treated with the therapeutic composition may be examined for the presence of apoptotic foci and compared to untreated control xenograft-bearing mice. The extent to which apoptotic foci are found in the tumors of the treated mice provides an indication of the therapeutic efficacy of the composition.

The therapeutic compositions used in the practice of the foregoing methods may be formulated into pharmaceutical compositions comprising a carrier suitable for the desired delivery method. Suitable carriers include any material that when combined with the therapeutic composition retains the anti-tumor function of the therapeutic composition and is non-reactive with the patient's immune system. Examples include, but are not limited to, any of a number of standard pharmaceutical carriers such as sterile phosphate buffered saline solutions, bacteriostatic water, and the like (see, generally, Remington's Pharmaceutical Sciences 16$^{th}$ Ed., A. Osal., Ed., 1980).

Therapeutic formulations may be solubilized and administered via any route capable of delivering the therapeutic composition to the tumor site. Potentially effective routes of administration include, but are not limited to, intravenous, parenteral, intraperitoneal, intramuscular, intratumor, intradermal, intraorgan, orthotopic, and the like. A preferred formulation for intravenous injection comprises the therapeutic composition in a solution of preserved bacteriostatic water, sterile unpreserved water, and/or diluted in polyvinylchloride or polyethylene bags containing 0.9% sterile Sodium Chloride for Injection, USP. Therapeutic protein preparations may be lyophilized and stored as sterile powders, preferably under vacuum, and then reconstituted in bacteriostatic water containing, for example, benzyl alcohol preservative, or in sterile water prior to injection.

Dosages and administration protocols for the treatment of cancers using the foregoing methods will vary with the method and the target cancer and will generally depend on a number of other factors appreciated in the art.

Cancer Vaccines

As noted above, the expression profile of 36P6D5 shows that it is highly expressed in advanced and metastasized prostate cancer. This expression pattern is reminiscent of the Cancer-Testis (CT) antigens or MAGEs, which are testis-specific genes that are up-regulated in melanomas and other cancers (Van den Eynde and Boon, Int J Clin Lab Res. 27:81-86, 1997). Due to their tissue-specific expression and high expression levels in cancer, the MAGEs are currently being investigated as targets for cancer vaccines (Durrant, Anticancer Drugs 8:727-733, 1997; Reynolds et al., Int J Cancer 72:972-976, 1997).

The invention further provides cancer vaccines comprising a 36P6D5 protein or fragment thereof, as well as DNA based vaccines. In view of the expression of 36P6D5 cancer vaccines are expected to be effective at specifically preventing and/or treating 36P6D5 expressing cancers without creating non-specific effects on non-target tissues. The use of a tumor antigen in a vaccine for generating humoral and cell-mediated immunity for use in anti-cancer therapy is well known in the art and has been employed in prostate cancer using human PSMA and rodent PAP immunogens (Hodge et al., 1995, Int. J. Cancer 63:231-237; Fong et al., 1997, J. Immunol. 159: 3113-3117). Such methods can be readily practiced by employing a 36P6D5 protein, or fragment thereof, or a 36P6D5-encoding nucleic acid molecule and recombinant vectors capable of expressing and appropriately presenting the 36P6D5 immunogen. An illustrative example of a typical technique consists of a method of generating an immune response (e.g. a humoral response) in a mammal comprising the steps exposing the mammal's immune system to an immunoreactive epitope (e.g. an epitope of the 36P6D5 protein shown in SEQ ID NO: 2) so that the mammal generates an immune response that is specific for that epitope is generated (e.g. antibodies that specifically recognize that epitope).

For example, viral gene delivery systems may be used to deliver a 36P6D5-encoding nucleic acid molecule. Various viral gene delivery systems that can be used in the practice of this aspect of the invention include, but are not limited to, vaccinia, fowlpox, canarypox, adenovirus, influenza, poliovirus, adeno-associated virus, lentivirus, and sindbus virus (Restifo, 1996, Curr. Opin. Immunol. 8:658-663). Non-viral delivery systems may also be employed by using naked DNA encoding a 36P6D5 protein or fragment thereof introduced into the patient (e.g., intramuscularly) to induce an anti-tumor response. In one embodiment, the full-length human 36P6D5 cDNA may be employed. In another embodiment, 36P6D5 nucleic acid molecules encoding specific cytotoxic T lymphocyte (CTL) epitopes may be employed. CTL epitopes can be determined using specific algorithms (e.g., Epimer, Brown University) to identify peptides within a 36P6D5 protein that are capable of optimally binding to specified HLA alleles.

Various ex vivo strategies may also be employed. One approach involves the use of dendritic cells to present 36P6D5 antigen to a patient's immune system. Dendritic cells express MHC class I and II, B7 co-stimulator, and IL-12, and are thus highly specialized antigen presenting cells. In prostate cancer, autologous dendritic cells pulsed with peptides of the prostate-specific membrane antigen (PSMA) are being used in a Phase I clinical trial to stimulate prostate cancer patients' immune systems (Tjoa et al., 1996, Prostate 28:65-69; Murphy et al., 1996, Prostate 29:371-380). Dendritic cells can be used to present 36P6D5 peptides to T cells in the context of MHC class I and II molecules. In one embodiment, autologous dendritic cells are pulsed with 36P6D5 peptides capable of binding to MHC molecules. In another embodiment, dendritic cells are pulsed with the complete 36P6D5 protein. Yet another embodiment involves engineering the overexpression of the 36P6D5 gene in dendritic cells using various implementing vectors known in the art, such as adenovirus (Arthur et al., 1997, Cancer Gene Ther. 4:17-25), retrovirus (Henderson et al., 1996, Cancer Res. 56:3763-3770), lentivirus, adeno-associated virus, DNA transfection (Ribas et al., 1997, Cancer Res. 57:2865-2869), and tumor-derived RNA transfection (Ashley et al., 1997, J. Exp. Med. 186: 1177-1182). Cells expressing 36P6D5 may also be engineered to express immune modulators, such as GM-CSF, and used as immunizing agents.

Anti-idiotypic anti-36P6D5 antibodies can also be used in anti-cancer therapy as a vaccine for inducing an immune response to cells expressing a 36P6D5 protein. Specifically, the generation of anti-idiotypic antibodies is well known in the art and can readily be adapted to generate anti-idiotypic anti-36P6D5 antibodies that mimic an epitope on a 36P6D5 protein (see, for example, Wagner et al., 1997, Hybridoma 16: 33-40; Foon et al., 1995, J. Clin. Invest. 96:334-342; Herlyn et al., 1996, Cancer Immunol. Immunother. 43:65-76). Such an anti-idiotypic antibody can be used in cancer vaccine strategies.

Genetic immunization methods may be employed to generate prophylactic or therapeutic humoral and cellular immune responses directed against cancer cells expressing 36P6D5. Constructs comprising DNA encoding a 36P6D5 protein/immunogen and appropriate regulatory sequences may be injected directly into muscle or skin of an individual, such that the cells of the muscle or skin take-up the construct and express the encoded 36P6D5 protein/immunogen. Expression of the 36P6D5 protein immunogen results in the generation of prophylactic or therapeutic humoral and cellular immunity against bone, colon, pancreatic prostate, kidney, bladder and ovarian cancers. Various prophylactic and therapeutic genetic immunization techniques known in the art may be used (for review, see information and references published at Internet address www.genweb.com).

Diagnostic Compositions and Kits

For use in the diagnostic and therapeutic applications described or suggested above, kits are also provided by the invention. Such kits may comprise a carrier means being compartmentalized to receive in close confinement one or more container means such as vials, tubes, and the like, each of the container means comprising one of the separate elements to be used in the method. For example, one of the container means may comprise a probe that is or can be detectably labeled. Such probe may be an antibody or polynucleotide specific for a 36P6D5 protein or a 36P6D5 gene or message, respectively. Where the kit utilizes nucleic acid hybridization to detect the target nucleic acid, the kit may also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radioisotope label.

The kit of the invention will typically comprise the container described above and one or more other containers comprising materials desirable from a commercial and user standpoint, including buffers, diluents, filters, needles, syringes, and package inserts with instructions for use. A label may be present on the on the container to indicate that the composition is used for a specific therapy or non-therapeutic application, and may also indicate directions for either in vivo or in vitro use, such as those described above.

Accordingly, the invention also provides diagnostic compositions comprising 36P6D5-related molecules. Such molecules include the various 36P6D5 polynucleotides, primers, probes, proteins, fragments, antibodies described herein. The molecules included in the diagnostic composition may optionally be labeled with a detectable marker. 36P6D5 diagnostic compositions may further comprise appropriate buffers, diluents, and other ingredients as desired.

EXAMPLES

Various aspects of the invention are further described and illustrated by way of the several examples which follow, none of which are intended to limit the scope of the invention.

Example 1

SSH-Generated Isolation of cDNA Fragment of the 36P6D5 Gene

Materials and Methods

LAPC Xenografts:

LAPC xenografts were obtained from Dr. Charles Sawyers (UCLA) and generated as described (Klein et al, 1997, Nature Med. 3: 402-408). Androgen dependent LAPC-4 xenografts (LAPC-4 AD) were grown subcutaneously in male SCID mice and were passaged as small tissue chunks in recipient males. LAPC-4 AD xenografts were grown intratibially as follows. LAPC-4 AD xenograft tumor tissue grown subcutaneously was minced into 1-2 $mm^3$ sections while the tissue was bathed in 1× Iscoves medium, minced tissue was then centrifuged at 1.3K rpm for 4 minutes, the supernatant was resuspended in 10 ml ice cold 1× Iscoves medium and centrifuged at 1.3K rpm for 4 minutes. The pellet was then resuspended in 1× Iscoves with 1% pronase E and incubated for 20 minutes at room temperature with mild rocking agitation followed by incubation on ice for 2-4 minutes. Filtrate was centrifuged at 1.3K rmp for 4 minutes, and the pronase was removed from the aspirated pellet by resuspending in 10 ml Iscoves and re-centrifuging. Clumps of cells were then plated in PrEGM medium and grown overnight. The cells were then harvested, filtered, washed 2×RPMI, and counted. Approximately 50,000 cells were mixed with and equal volume of ice-cold Matrigel on ice, and surgically injected into the proximal tibial metaphyses of SCID mice via a 27 gauge needle. After 10-12 weeks, LAPC-4 tumors growing in bone marrow were recovered.

Cell Lines:

Human cell lines (e.g., HeLa) were obtained from the ATCC and were maintained in DMEM with 5% fetal calf serum.

RNA Isolation:

Tumor tissue and cell lines were homogenized in Trizol reagent (Life Technologies, Gibco BRL) using 10 ml/g tissue or 10 ml/$10^8$ cells to isolate total RNA. Poly A RNA was purified from total RNA using Qiagen's Oligotex mRNA Mini and Midi kits. Total and mRNA were quantified by spectrophotometric analysis (O.D. 260/280 nm) and analyzed by gel electrophoresis.

Oligonucleotides:

The following HPLC purified oligonucleotides were used.

DPNCDN (cDNA synthesis primer):

(SEQ ID NO: 3)
5'TTTGATCAAGCTT$_{30}$3'

Adaptor 1:

(SEQ ID NO: 4)
5'CTAATACGACTCACTATAGGGCTCGAGCGGCCGCCCGGGCAG3'

(SEQ ID NO: 5)
3'GGCCCGTCCTAG5'

Adaptor 2:

(SEQ ID NO: 6)
5'GTAATACGACTCACTATAGGGCAGCGTGGTCGCGGCCGAG3'

(SEQ ID NO: 7)
3'CGGCTCCTAG5'

PCR primer 1:

(SEQ ID NO: 8)
5'CTAATACGACTCACTATAGGGC3'

Nested primer (NP)1:

(SEQ ID NO: 9)
5'TCGAGCGGCCGCCCGGGCAGGA3'

Nested primer (NP)2:

(SEQ ID NO: 10)
5'AGCGTGGTCGCGGCCGAGGA3'

Suppression Subtractive Hybridization:

Suppression Subtractive Hybridization (SSH) was used to identify cDNAs corresponding to genes which may be differentially expressed in prostate cancer. The SSH reaction utilized cDNA from LAPC-4 AD xenografts growing in two different environments, namely the subcutaneous ("LAPC-4 AD SQ") and intratibial ("LAPC-4 AD IT") growth environments, wherein the LAPC-4 AD IT xenograft was used as the source of the "tester" cDNA, while the LAPC-4 AD SQ xenograft was used as the source of the "driver" cDNA.

Double stranded cDNAs corresponding to tester and driver cDNAs were synthesized from 2 µg of poly(A)$^+$ RNA isolated from the relevant xenograft tissue, as described above, using CLONTECH's PCR-Select cDNA Subtraction Kit and 1 ng of oligonucleotide DPNCDN as primer. First- and second-strand synthesis were carried out as described in the Kit's user manual protocol (CLONTECH Protocol No. PT1117-1, Catalog No. K1804-1). The resulting cDNA was digested with Dpn II for 3 hrs. at 37° C. Digested cDNA was extracted with phenol/chloroform (1:1) and ethanol precipitated.

Driver cDNA was generated by combining Dpn II digested cDNA from the human cell lines HeLa, 293, A431, Colo205, and mouse liver. Tester cDNA was generated by diluting 1 µl of Dpn II digested cDNA from the relevant xenograft source (see above) (400 ng) in 5 µl of water. The diluted cDNA (2 µl, 160 ng) was then ligated to 2 µl of Adaptor 1 and Adaptor 2 (10 µM), in separate ligation reactions, in a total volume of 10 µl at 16° C. overnight, using 400 u of T4 DNA ligase (CLONTECH). Ligation was terminated with 1 µl of 0.2 M EDTA and heating at 72° C. for 5 min.

The first hybridization was performed by adding 1.5 µl (600 ng) of driver cDNA to each of two tubes containing 1.5 µl (20 ng) Adaptor 1- and Adaptor 2-ligated tester cDNA. In a final volume of 4 µl, the samples were overlaid with mineral oil, denatured in an MJ Research thermal cycler at 98° C. for 1.5 minutes, and then were allowed to hybridize for 8 hrs at 68° C. The two hybridizations were then mixed together with an additional 1 µl of fresh denatured driver cDNA and were allowed to hybridize overnight at 68° C. The second hybridization was then diluted in 200 µl of 20 mM Hepes, pH 8.3, 50 mM NaCl, 0.2 mM EDTA, heated at 70° C. for 7 min. and stored at −20° C.

PCR Amplification, Cloning and Sequencing of Gene Fragments Generated from SSH:

To amplify gene fragments resulting from SSH reactions, two PCR amplifications were performed. In the primary PCR reaction 1 µl of the diluted final hybridization mix was added to 1 µl of PCR primer 1 (10 µM) 0.5 µl dNTP mix (10 µM), 2.5 µl 10× reaction buffer (CLONTECH) and 0.5 µl 50× Advantage cDNA polymerase Mix (CLONTECH) in a final volume of 25 µl. PCR 1 was conducted using the following conditions: 75° C. for 5 min., 94° C. for 25 sec., then 27 cycles of 94° C. for 10 sec, 66° C. for 30 sec, 72° C. for 1.5 min. Five separate primary PCR reactions were performed for each experiment. The products were pooled and diluted 1:10 with water. For the secondary PCR reaction, 1 µl from the pooled and diluted primary PCR reaction was added to the same reaction mix as used for PCR 1, except that primers NP1 and NP2 (10 µM) were used instead of PCR primer 1. PCR 2 was performed using 10-12 cycles of 94° C. for 10 sec, 68° C. for 30 sec, 72° C. for 1.5 minutes. The PCR products were analyzed using 2% agarose gel electrophoresis.

The PCR products were inserted into pCR2.1 using the T/A vector cloning kit (Invitrogen). Transformed E. coli were subjected to blue/white and ampicillin selection. White colonies were picked and arrayed into 96 well plates and were grown in liquid culture overnight. To identify inserts, PCR amplification was performed on 1 µl of bacterial culture using the conditions of PCR1 and NP1 and NP2 as primers. PCR products were analyzed using 2% agarose gel electrophoresis.

Bacterial clones were stored in 20% glycerol in a 96 well format. Plasmid DNA was prepared, sequenced, and subjected to nucleic acid homology searches of the GenBank, dBest, and NCI-CGAP databases.

RT-PCR Expression Analysis:

First strand cDNAs were generated from 1 µg of mRNA with oligo (dT)12-18 priming using the Gibco-BRL Superscript Preamplification system. The manufacturers protocol was used and included an incubation for 50 min at 42° C. with reverse transcriptase followed by RNAse H treatment at 37° C. for 20 min. After completing the reaction, the volume was increased to 200 µl with water prior to normalization. First strand cDNAs from 16 different normal human tissues were obtained from Clontech.

Normalization of the first strand cDNAs from multiple tissues was performed by using the primers 5'atatcgc-cgcgctcgtcgtcgacaa3' (SEQ ID NO: 11) and 5'agccacacg-cagctcattgtagaagg 3' (SEQ ID NO: 12) to amplify β-actin. First strand cDNA (5 µl) was amplified in a total volume of 50 µl containing 0.4 µM primers, 0.2 µM each dNTPs, 1×PCR buffer (Clontech, 10 mM Tris-HCL, 1.5 mM MgCl$_2$, 50 mM KCl, pH8.3) and 1× Klentaq DNA polymerase (Clontech). Five µl of the PCR reaction was removed at 18, 20, and 22 cycles and used for agarose gel electrophoresis. PCR was performed using an MJ Research thermal cycler under the following conditions: initial denaturation was at 94° C. for 15 sec, followed by a 18, 20, and 22 cycles of 94° C. for 15, 65° C. for 2 min, 72° C. for 5 sec. A final extension at 72° C. was carried out for 2 min. After agarose gel electrophoresis, the band intensities of the 283 bp β-actin bands from multiple tissues were compared by visual inspection. Dilution factors for the first strand cDNAs were calculated to result in equal β-actin band intensities in all tissues after 22 cycles of PCR. Three rounds of normalization were required to achieve equal band intensities in all tissues after 22 cycles of PCR.

To determine expression levels of the 36P6D5 gene, 5 µl of normalized first strand cDNA was analyzed by PCR using 25, 30, and 35 cycles of amplification using the following primer pairs:

```
36P6D5.1   GCATTCTTGGCATCGTTATTCAG   (SEQ ID NO: 13)

36P6D5.2   TAACTGGGAATGTGACAGCAACAC  (SEQ ID NO: 14)
```

Semi quantitative expression analysis was achieved by comparing the PCR products at cycle numbers that give light band intensities.

Results:

The SSH experiment described in the Materials and Methods, supra, led to the isolation of numerous candidate gene fragment clones (SSH clones). All candidate clones were sequenced and subjected to homology analysis against all sequences in the major public gene and EST databases in order to provide information on the identity of the corresponding gene and to help guide the decision to analyze a particular gene for differential expression. In general, gene fragments which had no homology to any known sequence in any of the searched databases, and thus considered to represent novel genes, as well as gene fragments showing homology to previously sequenced expressed sequence tags ESTs), were subjected to differential expression analysis by RT-PCR and/or Northern analysis.

One of the SHH clones comprising about 423 bp, showed no homology to any known gene, and was designated 36P6D5. Initial expression analysis of 36P6D5 by RT-PCR showed highest expression in LAPC-4 AD (IT) and normal prostate compared to the other samples. This clone, therefore, was utilized for obtaining a full length cDNA encoding 36P6D5 as described in Example 2, below.

Example 2

Isolation of Full Length cDNA Encoding the 36P6D5 Gene

The isolated 36P6D5 gene fragment of 423 bp was used as a probe to identify the full length cDNA for 36P6D5 in a human prostate cDNA library. This resulted in the isolation of a 931 bp cDNA, clone 36P6D5-GTC4, which encodes a 235 amino acid ORF with significant homology to two previously reported sequences, the 2-19 protein precursor (Genbank P98173) and a gene isolated from human osteoblasts termed GS3786 (Q92520).

The nucleotide and deduced amino acid sequences of the clone 36P6D5-GTC4 cDNA are shown in FIG. 1. The encoded amino acid sequence exhibits an N-terminal signal sequence, which predicts the protein to be secreted (using the PSORT program). amino Acid sequence alignments of the 36P6D5 protein with 2-19 protein precursor and osteoblast protein GS3786 are shown in FIG. 2.

Example 3

Northern Blot Analysis of 36P6D5 Gene Expression

36P6D5 mRNA expression in normal human tissues was first analyzed by Northern blotting two multiple tissue blots obtained from Clontech (Palo Alto, Calif.), comprising a total of 16 different normal human tissues, using labeled 36P6D5 cDNA as a probe. RNA samples were quantitatively normalized with a β-actin probe. The results are shown in FIG. 3 and indicate that, within the 16 tissues tested, the 36P6D5 gene is predominantly expressed in pancreas, with very low level expression also detected in prostate and small intestine.

In addition, in order to analyze 36P6D5 expression in human cancer tissues and cell lines, RNAs derived from LAPC-4 human prostate cancer xenografts and a panel of non-prostate cancer cell lines were analyzed by Northern blot using the 36P6D5 cDNA as probe. All RNA samples were quantitatively normalized by ethidium bromide staining and subsequent analysis with a labeled β-actin probe. The results of this analysis are presented in FIG. 4, and show 36P6D5 expression in LAPC-4 prostate cancer xenografts growing subcutaneously and intratibially, in all cases at higher levels relative to normal prostate. Additionally, significant expression was detected in several non-prostate cancer cell lines including pancreatic (Capan-1), colon (CaCo-2, Colo-205), breast (CAMA-1, DU4475), and ovarian (SW626, CAOV-3, OV1063) cancer cells, also at high levels in some cases. In particular, the highest level of expression was detected in the breast cancer cell line DU4475.

Example 4

Production and Purification of Recombinant 36P6D5

To express recombinant 36P6D5 for use in a number of contexts such as analyzing the subcellular localization of 36P6D5 protein, a partial or the full length cDNA can cloned into any one of a variety of expression vectors such as those that provide a 6H is tag at the carboxyl-terminus (e.g. pcDNA 3.1 myc-his, InVitrogen).

In a typical embodiment, in order to drive high level expression of 36P6D5 protein, the 36P6D5 cDNA encoding amino acids 30-235 (minus N-terminal signal sequence) was cloned into the pAPTag5 mammalian secretion vector (Gen-Hunter) with and without fusion to the provided alkaline phosphatase (AP) cDNA sequence. This vector provides a C-terminal 6×His and MYC tag for purification and detection and an N-terminal Ig leader sequence to drive secretion. 293T cells stably expressing either pAPTag5-36P6D5 or pTag5-36P6D5 (not fused to AP) serve as a source of recombinant protein for purification as visualized by an anti-His Western blot of conditioned media from these cell lines (FIG. 5). The HIS-tagged 36P6D5 proteins present in the conditioned media are purified using the following method. Conditioned media is concentrated 5-10 fold and simultaneously buffer exchanged into a phosphate buffer (pH 8.0) containing 500 mM, NaCl and 20 mM imidazole (buffer A) using an amicon ultrafiltration unit with a 10 kd MW cutoff membrane. The prep is batch bound to 0.1 to 0.5 ml of nickel metal affinity resin (Ni-NTA, Qiagen) and washed extensively with buffer A. The HIS-tagged SGP-28/CRISP-3 protein is then eluted with a 0 to 400 mM gradient of imidazole in phosphate buffer (pH 6.3) containing 300 mM NaCl and then dialyzed extensively against PBS. The purified protein may then be used for growth assays, ligand binding studies, or as immunogen for generating antibody reagents.

Additional embodiments of typical constructs are provided below.

pcDNA3.1/MycHis Construct

To express 36P6D5 in mammalian cells, the 705 bp (235 amino acid) 36P6D5 ORF was cloned into pcDNA3.1/McHis_Version A (Invitrogen, Carlsbad, Calif.). Protein expression is driven from the cytomegalovirus (CMV) promoter. The recombinant protein has the myc and six histidines fused to the C-terminus. The pcDNA3.1/MycHis vector also contains the bovine growth hormone (BGH) polyadenylation signal and transcription termination sequence to enhance mRNA stability along with the SV40 origin for episomal replication and simple vector rescue in cell lines expressing the large T antigen. The Neomycin resistance gene allows for selection of mammalian cells expressing the protein and the ampicillin resistance gene and ColE1 origin permits selection and maintenance of the plasmid in *E. coli*.

pAPtag

The 36P6D5 protein without the signal sequence (amino acids 30 to 235) was cloned into pAPtag-5 (GenHunter Corp. Nashville, Tenn.). This construct generates an alkaline phosphatase fusion at the C-terminus of the 36P6D5 protein while fusing the IgGK signal sequence to N-terminus. The resulting recombinant 36P6D5 protein is optimized for secretion into the media of transfected mammalian cells and can be used to identify proteins such as ligands or receptors that interact with the 36P6D5 protein. Protein expression is driven from the CMV promoter and the recombinant protein also contains myc and six histidines fused to the C-terminus of alkaline phosphatase. The Zeosin resistance gene allows for selection of mammalian cells expressing the protein and the ampicillin resistance gene permits selection of the plasmid in *E. coli*.

ptag5

The 36P6D5 protein without the signal sequence (amino acids 30 to 235) was also cloned into pTag-5. This vector is similar to pAPtag but without the alkaline phosphatase fusion.

pSRa Constructs

To generate mammalian cell lines expressing 36P6D5 constitutively, the 705 bp (235 amino acid) ORF was cloned into pSRa constructs. Amphotropic and ecotropic retroviruses are generated by transfection of pSRa constructs into the 293T-10A1 packaging line or co-transfection of pSRa and a helper plasmid (φ□) in 293 cells, respectively. The retrovirus can be used to infect a variety of mammalian cell lines, resulting in the integration of the cloned gene, 36P6D5, into the host cell-lines. Protein expression is driven from a long terminal repeat (LTR). The Neomycin resistance gene allows for selection of mammalian cells expressing the protein and the ampicillin resistance gene and ColE1 origin permits selection and maintenance of the plasmid in *E. coli*. An additional pSRa construct was made that fused the FLAG tag to the C-terminus to allow detection using anti-FLAG antibodies. The FLAG nucleotide sequence was added to cloning primer at the 3' end of the ORF.

Additional pSRa constructs can be made to produce both N-terminal and C-terminal GFP and myc/6 HIS fusion proteins of the full-length 36P6D5 protein.

Example 5

Production of Recombinant 36P6D5 in a Baculovirus System

To generate recombinant 36P6D5 protein in a baculovirus expression system, 36P6D5 cDNA is cloned into the baculovirus transfer vector pBlueBac 4.5 (Invitrogen) which provides a His-tag at the N-terminus. Specifically, pBlueBac-36P6D5 is co-transfected with helper plasmid pBac-N-Blue (Invitrogen) into SF9 (*Spodoptera frugiperda*) insect cells to generate recombinant baculovirus (see Invitrogen instruction manual for details). Baculovirus is then collected from cell supernatant and purified by plaque assay.

Recombinant 36P6D5 protein is then generated by infection of HighFive insect cells (InVitrogen) with the purified baculovirus. Recombinant 36P6D5 protein may be detected using 36P6D5-specific antibody. 36P6D5 protein may be purified and used in various cell based assays or as immunogen to generate polyclonal and monoclonal antibodies specific for 36P6D5.

Example 6

Generation of 36P6D5 Polyclonal Antibodies

To generate polyclonal sera to 36P6D5 a peptide was synthesized corresponding to amino acids 163-177 (MVTYDDGSTRLNNDA) (SEQ ID NO: 12) of the SGP-28/CRISP-3 protein sequence was coupled to Keyhole limpet hemacyanin (KLH) and was used to immunize a rabbit as follows. The rabbit was initially immunized with 200 ug of peptide-KLH mixed in complete Freund's adjuvant. The rabbit was then injected every two weeks with 200 ug of peptide-KLH in incomplete Freund's adjuvant. Bleeds were taken approximately 7-10 days following each immunization. ELISA and Western blotting analyses were used to determine specificity and titer of the rabbit serum to the immunizing peptide and 36P6D5 protein respectively. Affinity purified 36P6D5 polyclonal antibodies were prepared by passage of crude serum from immunized rabbit over an affinity matrix comprised of 36P6D5 peptide (MVTYDDGSTRLNNDA) (amino acids 163-177 of SEQ ID NO: 2) covalently coupled to Affigel 15 (BioRad). After extensive washing of the matrix with PBS, antibodies specific to 36P6D5 peptide were eluted with low pH glycine buffer (0.1M, pH 2.5), immediately neutralized, and extensively dialyzed against PBS.

To test the rabbit polyclonal antibody for reactivity with 36P6D5 protein, Western blot analysis was carried out against conditioned media of 293T cells transfected with the pAPTag5-36P6D5 or PTag5-36P6D5 expression vectors. Affinity purified rabbit anti-36P6D5 pAb (1 µg/ml) recognizes both forms of recombinant 36P6D5 protein secreted from 293T cells (FIG. 5).

Example 7

Generation of 36P6D5 Monoclonal Antibodies

In order to generate 36P6D5 monoclonal antibodies, purified 293T-expressed HIS-tagged 36P6D5 protein is used to immunize Balb/C mice. Balb C mice are initially immunized intraperitoneally with 50 µg of 36P6D5 protein mixed in complete Freund's adjuvant. Mice are subsequently immunized every 2 weeks with 50 µg of 36P6D5 protein mixed in Freund's incomplete adjuvant for a total of 3 immunizations. Reactivity of serum from immunized mice to full length 36P6D5 protein is monitored by ELISA using the immunogen and by Western blot using conditioned media from cells expressing 36P6D5 protein. Mice showing the strongest reactivity are rested for 3 weeks and given a final injection of fusion protein in PBS and then sacrificed 4 days later. The spleens of the sacrificed mice are then harvested and fused to SPO/2 myeloma cells or other suitable myeloma fusion partner using standard procedures (Harlow and Lane, 1988). Supernatants from growth wells following HAT selection are screened by ELISA and Western blot to identify 36P6D5 specific antibody producing clones.

The binding affinity of a 36P6D5 monoclonal antibody may be determined using standard technology. Affinity measurements quantify the strength of antibody to epitope binding and may be used to help define which 36P6D5 monoclonal antibodies are preferred for diagnostic or therapeutic use. The BIAcore system (Uppsala, Sweden) is a preferred method for determining binding affinity. The BIAcore system uses surface plasmon resonance (SPR, Welford K. 1991, Opt. Quant. Elect. 23:1; Morton and Myszka, 1998, Methods in Enzymology 295: 268) to monitor biomolecular interactions in real time. BIAcore analysis conveniently generates association rate constants, dissociation rate constants, equilibrium dissociation constants, and affinity constants.

Figures 9A, 9B:
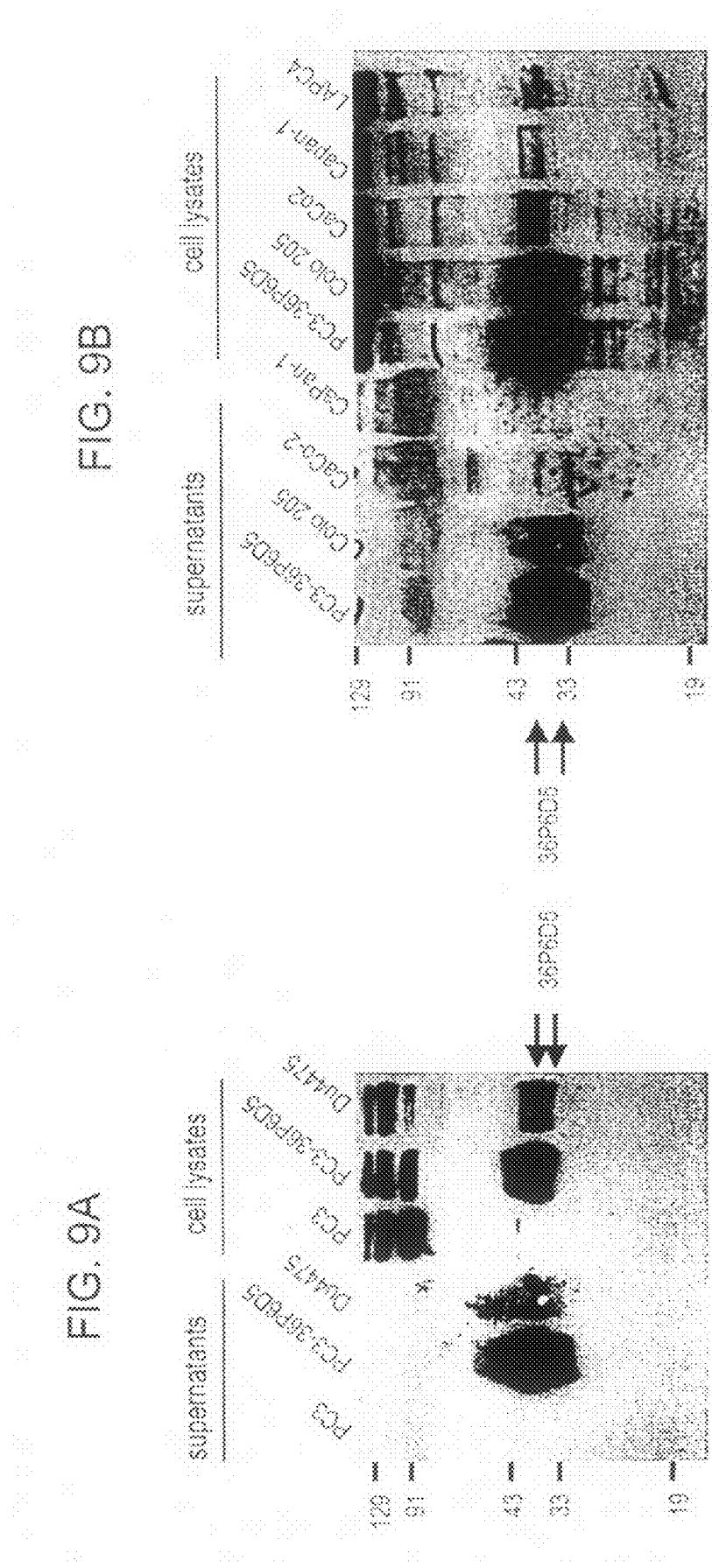
FIGS. 9A-9B. Human cancer cells express and secrete 36P6D5 protein. Conditioned media and/or cell lysates from a variety of cancer cell lines representing cancers derived from prostate (LAPC4 xenograft), colon (Colo 205, CaCo-1), breast (Du4475), and pancreatic (Capan-1) tissues, as well as PC3 prostate cancer cells engineered to overexpress 36P6D5 protein, were subjected to Western analysis using an anti-36P6D5 murine pAb. The specific anti-36P6D5 immunoreactive bands representing endogenous 36P6D5 protein are indicated with arrows and run approximately between 35 and 40 kD. The molecular weight of 36P6D5 calculated from the amino acid sequence is 26 kD suggesting that endogenous 36P6D5 protein is post-translationally modified, possibly by glycosylation.

In a specific illustration of a typical method for generating 36P6D5 monoclonal antibodies, purified 293T-expressed HIS-tagged 36P6D5 protein was used to immunize 3 female Balb C mice. Balb C mice were initially immunized intraperitoneally (IP) with 50 µg of 36P6D5 protein mixed in Ribi adjuvant and boosted 2 additional times IP in 2 week intervals with 25 ug of 36P6D5 protein in Ribi adjuvant. Following the third boost, mice were subsequently immunized with 25 ug of protein IP in PBS. ELISA analysis of test bleeds following the fourth immunization indicated a titer of at least $2\times10^6$ for each of the immunized mice toward the immunogen. The serum from the immunized mice specifically recognize endogenous 36P6D5 protein in cell lysates and conditioned media from a variety of cancer cell lines including cell lines derived from prostate (LAPC4 xenograft), colon (Colo 205, CaCo-2), breast (DU4475), and pancreatic (Capan-1) cancers (FIG. 9). In addition, purified polyclonal antibodies from the sera were used to develop a capture ELISA that specifically detects 36P6D5 protein in the supernatants of PC-3-36P6D5 and DU4475 cell lines and in clinical serum samples (Table 2). For generation of anti-36P6D5 hybridomas, mice are given a final boost of 25 ug of 36P6D5 IP, sacrificed 3 days later and harvested spleen cells are fused to myeloma partners using standard procedures (Harlow and Lane, 1988). Supernatants from fused hybridoma growth wells are screened by ELISA and Western blot to identify 36P6D5 specific antibody producing clones.

Using these antibodies, 36P6D5 protein was detected in several cancer cell lines including those derived from colon, pancreas, and breast, and in prostate cancer xenografts (FIG. 9). In addition, 36P6D5 protein was detected in conditioned medium of cells that express the protein endogenously, demonstrating that it is a secreted protein and that it may serve as a diagnostic serum marker. Indeed, using a sensitive capture ELISA (FIG. 10), 36P6D5 protein was detected in 7/10 colon cancer samples and 6/10 pancreatic cancer samples, but only 1/6 normal male samples (Table 2). These results provide evidence that 36P6D5 may serve as a diagnostic and possibly a therapeutic target for colon and pancreatic cancer as well as other cancers including those derived from prostate and breast tissues.

Example 8

Identification of Potential Signal Transduction Pathways

To determine whether 36P6D5 directly or indirectly activates known signal transduction pathways in cells, luciferase (luc) based transcriptional reporter assays are carried out in cells expressing 36P6D5. These transcriptional reporters contain consensus binding sites for known transcription factors which lie downstream of well characterized signal transduction pathways. The reporters and examples of there associated transcription factors, signal transduction pathways, and activation stimuli are listed below.

1. NFkB-luc, NFkB/Rel; Ik-kinase/SAPK; growth/apoptosis/stress
2. SRE-luc, SRF/TCF/ELK1; MAPK/SAPK; growth/differentiation
3. AP-1-luc, FOS/JUN; MAPK/SAPK/PKC; growth/apoptosis/stress
4. ARE-luc, androgen receptor; steroids/MAPK; growth/differentiation/apoptosis
5. p53-luc, p53; SAPK; growth/differentiation/apoptosis
6. CRE-luc, CREB/ATF2; PKA/p38; growth/apoptosis/stress 36P6D5-mediated effects may be assayed in cells showing mRNA expression, such as the 36P6D5-expressing cancer cell lines shown in FIG. 4. Luciferase reporter plasmids may be introduced by lipid mediated transfection (TFX-50, Promega). Luciferase activity, an indicator of relative transcriptional activity, is measured by incubation of cells extracts with luciferin substrate and luminescence of the reaction is monitored in a luminometer.

Example 9

In Vitro Assays of 36P6D5 Function

The expression profile of 36P6D5 in cancer suggests a functional role in tumor initiation, progression and/or maintenance. 36P6D5 may function as a secreted factor that stimulates the proliferation of prostate cancer cells in bone. 36P6D5 function can be assessed in mammalian cells using in vitro approaches. For mammalian expression, 36P6D5 can be cloned into a number of appropriate vectors, including pcDNA 3.1 myc-His-tag and the retroviral vector pSRαtkneo (Muller et al., 1991, MCB 11:1785). Using such expression vectors, 36P6D5 can be expressed in several cancer cell lines, including for example PC-3, NIH 3T3, LNCaP and 293T. Expression of 36P6D5 can be monitored using anti-36P6D5 antibodies.

Mammalian cell lines expressing 36P6D5 can be tested in several in vitro and in vivo assays, including cell proliferation in tissue culture, activation of apoptotic signals, primary and metastatic tumor formation in SCID mice, and in vitro invasion using a membrane invasion culture system (MICS) (Welch et al., Int. J. Cancer 43: 449-457). 36P6D5 cell phenotype is compared to the phenotype of cells that lack expression of 36P6D5.

Cell lines expressing 36P6D5 can also be assayed for alteration of invasive and migratory properties by measuring passage of cells through a matrigel coated porous membrane chamber (Becton Dickinson). Passage of cells through the membrane to the opposite side is monitored using a fluorescent assay (Becton Dickinson Technical Bulletin #428) using calcein-Am (Molecular Probes) loaded indicator cells. Cell lines analyzed include parental and 36P6D5 overexpressing PC3, 3T3 and LNCaP cells. To assay whether 36P6D5 has chemoattractant properties, parental indicator cells are monitored for passage through the porous membrane toward a gradient of 36P6D5 conditioned media compared to control media. This assay may also be used to qualify and quantify specific neutralization of the 36P6D5 induced effect by candidate cancer therapeutic compositions. Cells can also be monitored for changes in growth, adhesiveness, and invasiveness in the presence and absence of exogenously added purified 36P6D5 protein.

In another functional assay, cells stably expressing 36P6D5 can be analyzed for their ability to form colonies in soft agar. In these experiments, cells used in such procedures (e.g. NIH-3T3 cells), can be transfected to stably express 36P6D5 or neo or activated-Ras (as the test gene, the negative and the positive controls, respectively) in order to assess the transforming capabilities of 36P6D5. Typically experiments are performed in duplicate and the assays are evaluated approximately 4 weeks after cell plating. Where experimental observations demonstrate that 36P6D5 induces an increase in colony formation relative to a negative control (e.g. neo) such results indicate that 36P6D5 has significant transforming capabilities.

In another functional assay, parental cells and cells expressing 36P6D5 can be compared for their ability to induce cytoplasmic accumulation of cAMP. In a typical embodiment, cells such as an LAPC xenograft (or any of a variety of other cells such as 293T cells) can be exposed to 36P6D5 and/or transfected with empty pcDNA4 HIS MAX vector or with pcDNA4 HIS MAX 36P6D5. Typically, cells are starved in 1% fetal bovine serum (FBS) overnight and incubated with media alone or in the presence of a secretory molecule or 10% FBS. The cells are then lysed and analyzed for cAMP content by enzyme linked immunoassay (EIA) according to the manufacturer's recommendations (Linco Research, St Charles, Mich.).

Many genes identified as playing a role in oncogenesis function by activating the CAMP signaling pathway. Typically, in the absence of ligand, signaling molecules are normally in an inactive state. Upon ligand binding or overexpression, such molecules acquire an active conformation and complex with G proteins. This interaction results in the dissociation of G protein subunits and the activation of adenylate cyclase, resulting in CAMP accumulation (Birnbaumer L, Cell 1992, 71:1069). Enhanced production of cAMP results in the activation of several downstream signaling pathways that mediate the effect of such molecules. A demonstration that cells contacted by or transfected with 36P6D5 leads to the accumulation of CAMP in response to FBS would indicate that 36P6D5 functions as a signaling molecule under these conditions.

Example 10

In Vivo Assay for 36P6D5 Tumor Growth Promotion

The effect of the 36P6D5 protein on tumor cell growth may be evaluated in vivo by gene overexpression in tumor-bearing mice. For example, SCID mice can be injected SQ on each flank with $1 \times 10^6$ of a number of prostate, breast, colon, pancreatic, and ovarian cell lines containing tkNeo empty vector or 36P6D5. At least two strategies may be used: (1) Constitutive 36P6D5 expression under regulation of an LTR promoter, and (2) Regulated expression under control of an inducible vector system, such as ecdysone, tet, etc. Tumor volume is then monitored at the appearance of palpable tumors and followed over time to determine if 36P6D5 expressing cells grow at a faster rate. Additionally, mice may be implanted with $1 \times 10^5$ of the same cells orthotopically to determine if 36P6D5 has an effect on local growth in the target tissue (i.e., prostate) or on the ability of the cells to metastasize, specifically to lungs, lymph nodes, liver, bone marrow, etc. In relation to prostate cancer, the effect of 36P6D5 on bone tumor formation and growth may be assessed by injecting prostate tumor cells intratibially, as described in Example 1.

These assays are also useful to determine the 36P6D5 inhibitory effect of candidate therapeutic compositions, such as for example, 36P6D5 antibodies, 36P6D5 antisense molecules and ribozymes.

Example 11

In Vitro Assay of 36P6D5 Protein Interaction

Cell lines expressing 36P6D5 can also be used to identify protein-protein interactions mediated by 36P6D5. The observation that 36P6D5 is a secreted molecule that binds to cells (see e.g. FIG. 8) provides evidence that this molecule interacts with other proteins on the cell surface. This interaction can be examined using immunoprecipitation techniques as shown by others (Hamilton B J, et al. Biochem. Biophys. Res. Commun. 1999, 261:646-51). 36P6D5 protein can be immunoprecipitated from 36P6D5 expressing prostate cancer cell lines and examined for protein association by western blotting. Protein interaction may be also studied by a two yeast hybrid system, as described by Shnyreva et. Al. (Shnyreva M et al, J Biol Chem. 2000. 19; 275; 15498-503). These assays may also be used to analyze the effect of potential cancer therapeutics on 36P6D5 function.

To determine the contribution of the various domains contained within the 36P6D5 ORF to 36P6D5 function, 36P6D5 mutants can be generated lacking one or more domains. Cell lines expressing mutant 36P6D5 protein will be evaluated for alteration in proliferation, invasion, migration, transcriptional activation and protein-protein interaction.

Example 12

Chromosomal Localization of 36P6D5

The chromosomal localization of 36P6D5 was determined using the GeneBridge4 radiation hybrid panel (Walter et al., 1994, Nat. Genetics 7:22) (Research Genetics, Huntsville Ala.). The following PCR primers were used to localize 36P6D5:

36P6D5.7 ATACCCAAAGAACGAAGCTGACAC (SEQ ID NO: 17)

36P6D5.8 TACTCATCAAATATGGGCTGTTGG (SEQ ID NO: 18)

The resulting mapping vector for the 93 radiation hybrid panel DNAs was:

000101110110100100100110110011111111101011111111011
111010000001011101100111000110111000100 1011

This the mapping program which can be found at internet address http://www-genome.wi.mit.edu/cgi-bin/contig/rhmapper.pl maps 36P6D5 to chromosome 21q22.2-22.3.

Example 13

Detecting Expression of 36P6D5 Proteins in Human Cancers

As shown in FIG. 9, a subset of cancer cells express and secrete 36P6D5 protein. Conditioned media and/or cell lysates from a variety of cancer cell lines representing cancers derived from prostate (LAPC4 xenograft), colon (Colo 205, CaCo-1), breast (Du4475), and pancreatic (Capan-1) tissues, as well as PC3 prostate cancer cells engineered to overexpress 36P6D5 protein, were subjected to Western analysis using an anti-36P6D5 murine pAb. Briefly, cells (~25 ug total protein) and conditioned media (25 ul of neat, 0.22 uM filtered media) were solubilized in SDS-PAGE sample buffer and separated on a 10-20% SDS-PAGE gel and transferred to nitrocellulose. Blots were blocked in Tris-buffered saline (TBS)+3% non-fat milk and then probed with a 1:1,000 dilution (in TBS+0.15% Tween-20+1% milk) of serum derived from mice immunized with purified 36P6D5 protein. Blots were then washed and incubated with a 1:4,000 dilution of anti-mouse IgG-HRP conjugated secondary antibody. Following washing, anti-36P6D5 immunoreactive bands were developed and visualized by enhanced chemiluminescence and exposure to autoradiographic film. The specific anti-36P6D5 immunoreactive bands representing endogenous 36P6D5 protein are indicated with arrows and run approximately between 35 and 40 kD. The molecular weight of 36P6D5 calculated from the amino acid sequence is 26 kD suggesting that endogenous 36P6D5 protein is post-translationally modified, possibly by glycosylation. These results demonstrate that 36P6D5 may be useful as a diagnostic and therapeutic target for prostate, colon, breast, pancreatic and potentially other human cancers.

Figure 10:
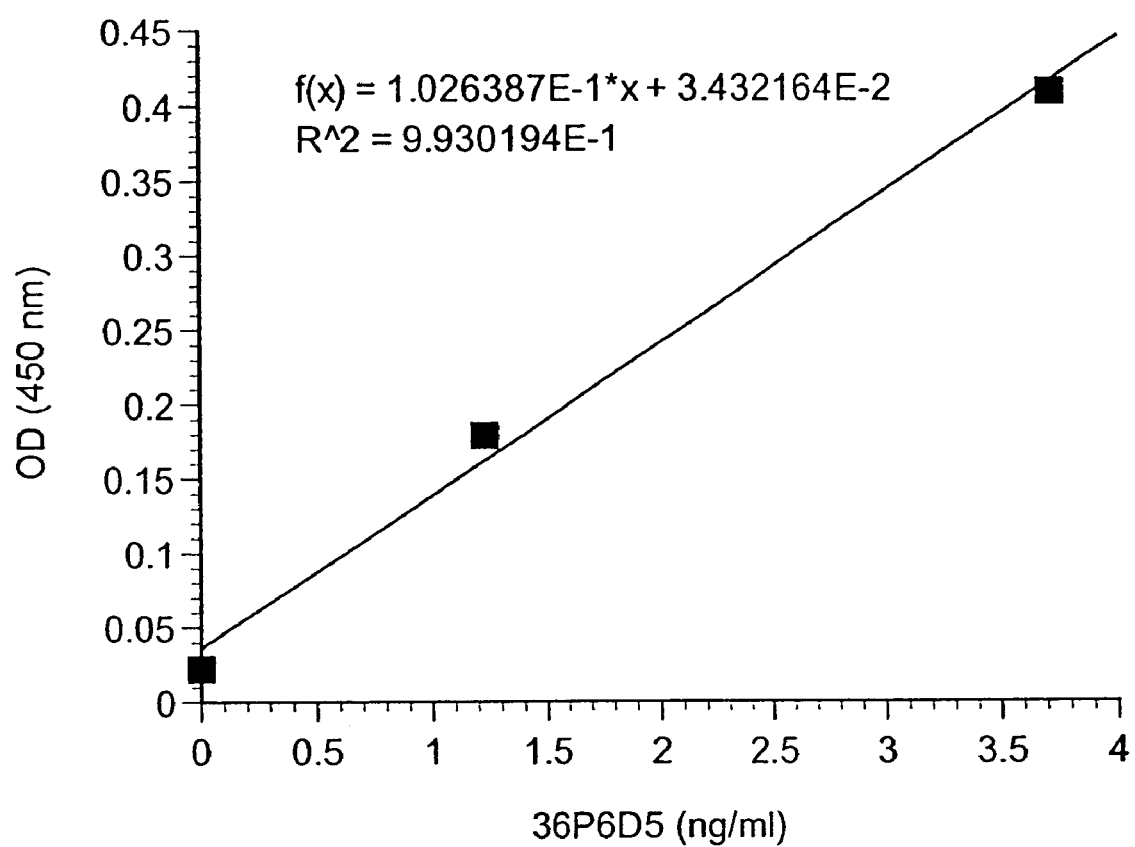
FIG. 10. A sensitive and specific capture ELISA detects 36P6D5 protein in supernatants of human cancer cell lines. A capture ELISA was developed using protein G purified murine anti-36P6D5 pAb as capture Ab and a biotinylated form of the same pAb as detection Ab. Shown is the standard curve generated using the Tag5-36P6D5 protein and specific detection and quantitation of 36P6D5 present in supernatants derived from PC-3-Neo transfected cells (O.D.=0.023, 36P6D5 protein concentration in ng/ml=N.D.), PC-3 cells overexpressing 36P6D5 (O.D.=0.186, 36P6D5 protein concentration in ng/ml=1.48) and endogenous 36P6D5 protein secreted by Du4475 breast cancer cells (O.D.=0.085, 36P6D5 protein concentration in ng/ml=0.50).

As shown in FIG. 10, a sensitive and specific capture ELISA detects 36P6D5 protein in supernatants of human cancer cell lines. A capture ELISA was developed using protein G purified murine anti-36P6D5 pAb as capture Ab and a biotinylated form of the same pAb as detection Ab. Briefly, 1 ug of purified murine anti-36P6D5 pAb was used to coat wells of an ELISA plate. Following blocking with PBS containing 3% milk, 50 ul of conditioned media from either PC3-neo, PC3-36P6D5, or DU4475 cells or various amounts of purified Tag5-36P6D5 protein spiked into tissue culture media were added to wells and incubated for 2 hours at room temperature. Wells were washed 4× with PBS+0.05% Tween-20 (PBS-T) and 1× with PBS. Wells were then incubated for 1 hour with 3 ug/ml of biotinylated anti-3606D5 pAb in PBS-T+1% milk (TBS-TM, 50 ul/well) and washed as above. Wells were then incubated with 50 ul of a 1:8,000 dilution of avidin-HRP complex (Neutralite™, Southern Biotechnology, Inc) in TBS-TM for 1 hour. Following washing, wells were then developed by addition of 200 ul of TMB substrate. The reaction was stopped by the addition of 50 ul of 1M H2SO4 and optical densities of wells were read at 450 nM. Shown is the standard curve generated using the Tag5-36P6D5 protein and specific detection and quantitation of 36P6D5 present in supernatants derived from PC-3 cells overexpressing 36P6D5 and endogenous 36P6D5 protein secreted by Du4475 breast cancer cells.

Figure 11A:
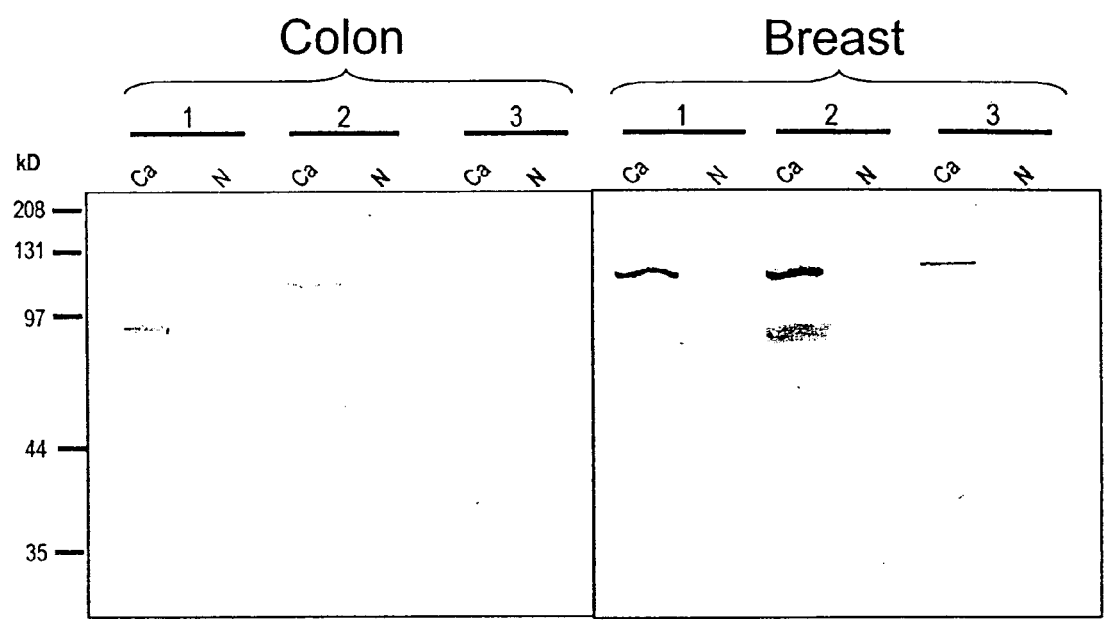
FIGS. 11A-11B. Detection of 36P6D5 expression in human cancers. Cell lysates from Colon, breast and kidney cancer tissues (Ca), as well as their normal matched adjacent tissues (N) were subjected to Western analysis using an anti-36P6D antibody. The specific anti-36P6D5 immunoreactive bands represent a monomeric form of the 36P6D5 protein, which runs approximately between 35 and 40 kD, and multimeric forms of the protein, which run approximately at 90 and 120 kD.
Figure 11B:
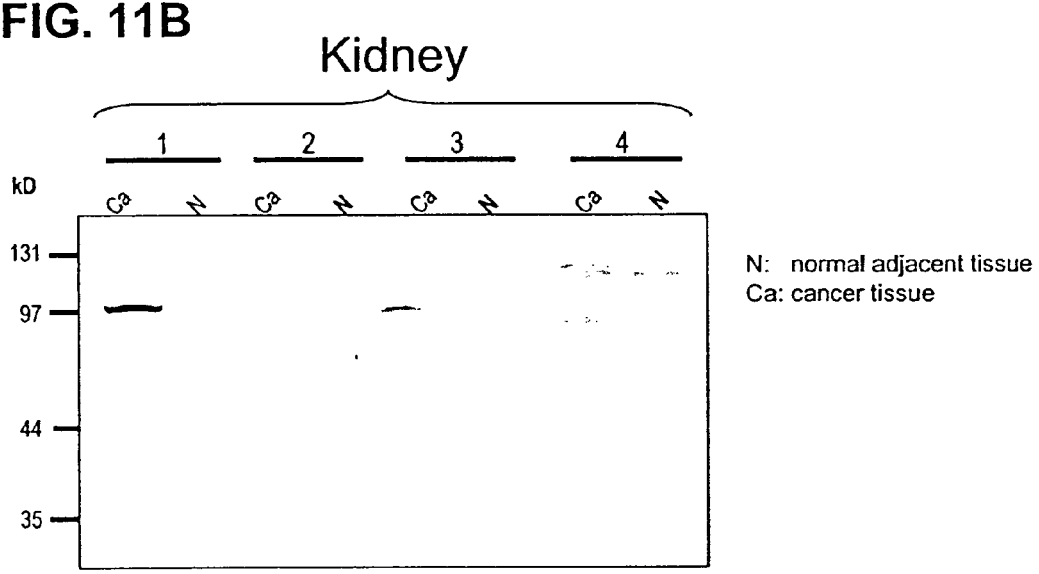

FIG. 11 also shows 36P6D5 expression in human cancers. As shown in FIG. 11, in a typical method for detecting expression of 36P6D5 in human cancers, cell lysates from Colon, breast and kidney cancer tissues (Ca), as well as their normal matched adjacent tissues (N) were subjected to Western analysis using an anti-36P6D5 mouse monoclonal antibody. Briefly, tissues (~25 ug total protein) were solubilized in SDS-PAGE sample buffer and separated on a 10-20% SDS-PAGE gel and transferred to nitrocellulose. Blots were blocked in Tris-buffered saline (TBS)+3% non-fat milk and then probed with 2 μg/ml (in TBS+0.15% Tween-20+1% milk) of purified anti-36P6D5 antibody. Blots were then washed and incubated with a 1:4,000 dilution of anti-mouse IgG-HRP conjugated secondary antibody. Following washing, anti-36P6D5 Immunoreactive bands were developed and visualized by enhanced chemiluminescence and exposure to autoradiographic film. The specific anti-36P6D5 immunoreactive bands represent a monomeric form of the 36P6D5 protein, which runs approximately between 35 and 40 kD, and multimeric forms of the protein, which run approximately at 90 and 120 kD. These results demonstrate that 36P6D5 may be useful as a diagnostic and therapeutic target for colon, breast, kidney and potentially other human cancers.

Throughout this application, various publications are referenced within parentheses. The disclosures of these publications are hereby incorporated by reference herein in their entireties.

The present invention is not to be limited in scope by the embodiments disclosed herein, which are intended as single illustrations of individual aspects of the invention, and any which are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

TABLE 1 predicted binding of peptides from 36P6D5 proteins to the human MHC class I molecule HLA-A2

| Rank | Start Position | Subsequence Residue Listing | Score (Estimate of half time of disassociation) |
|---|---|---|---|
| 1 | 7 | GLLKVVFVV (SEQ ID NO: 19) | 1407.5 |
| 2 | 97 | LMGEQLGNV (SEQ ID NO: 20) | 104.7 |

TABLE 1-continued predicted binding of peptides from 36P6D5 proteins to the human MHC class I molecule HLA-A2

| Rank | Start Position | Subsequence Residue Listing | Score (Estimate of half time of disassociation) |
|---|---|---|---|
| 3 | 27 | LLAELIPDA (SEQ ID NO: 21) | 79.6 |
| 4 | 188 | WVFIAAKGL (SEQ ID NO: 22) | 31.8 |
| 5 | 11 | VVFVVFASL (SEQ ID NO: 23) | 22.3 |
| 6 | 6 | GGLLKVVFV (SEQ ID NO: 24) | 21.2 |
| 7 | 190 | FIAAKGLEL (SEQ ID NO: 25) | 13.5 |
| 8 | 89 | KICFEDNLL (SEQ ID NO: 26) | 10.3 |
| 9 | 109 | INIAIVNYV (SEQ ID NO: 27) | 9.8 |
| 10 | 181 | NMKFRSSWV (SEQ ID NO: 28) | 9.7 |

TABLE 2

36P6D5 is detected in serum samples derived from cancer patients.

| | 36P6D5 Sample (ng/ml) |
|---|---|
| normal (M) | ND |
| normal (M) | ND |
| normal (M) | ND |
| normal (M) | ND |
| normal (M) | 1.31 |
| normal (M) | ND |
| | (1/6) |
| PC3-neo | ND |
| PC-3-36P6D5 | 3.38 |
| Du4475 | 0.92 |
| colon | ND |
| colon | 3.08 |
| colon | 0.31 |
| colon | ND |
| colon | 0.92 |
| colon | 0.77 |
| colon | 0.62 |
| colon | 1.23 |
| colon | 0.46 |
| colon | ND |
| | (7/10) |
| pancreatic | 0.15 |
| pancreatic | 0.38 |
| pancreatic | 29.70 |
| pancreatic | ND |
| pancreatic | 1.38 |
| pancreatic | 0.23 |
| pancreatic | ND |
| pancreatic | ND |
| pancreatic | 0.38 |
| pancreatic | ND |
| | (6/10) |

Clinical serum samples from and pancreatic cancer patients, and normal male donors were screened for 36P6D5 protein using a capture ELISA as described in FIG. 10. Supernatants from PC-3-36P6D5 and Du4475 cells, and from PC-3-neo cells, served as positive and negative controls, respectively for 36P6D5 protein detection. ND: not detected or below detection sensitivity. 36P6D5 protein was detected in 7/10 colon cancer patients and 6/10 pancreatic cancer patients, one of which had relatively high levels (29.70 ng/ml), but only in 1/6 normal male donors.

The invention claimed is:

1. A method of detecting the presence of breast, colon, kidney or pancreatic cancer expressing 36P6D5 protein that comprises determining the level of 36P6D5 protein expressed by cells in a breast, colon, kidney or pancreatic test tissue sample from an individual, wherein the 36P6D5 protein comprises SEQ ID NO:2, and comparing the level so determined to the level of 36P6D5 expressed in a corresponding normal breast, colon, kidney or pancreatic tissue sample, the presence of elevated 36P6D5 protein in the test sample relative to the normal sample providing an indication of the presence of such cancer in the individual.

2. The method of claim 1, wherein determining the level of 36P6D5 protein expressed by the cells comprises contacting the cells with an antibody that specifically binds 36P6D5 protein comprising the amino acid sequence of SEQ ID NO:2.

3. The method of claim 2, wherein the antibody comprises a polyclonal antibody.

4. The method of claim 2, wherein the antibody comprises a monoclonal antibody.

5. A method of monitoring 36P6D5 gene products comprising determining the status of 36P6D5 gene products expressed by cells in a test breast, colon, kidney or pancreatic tissue sample from an individual, wherein the 36P6D5 gene product is a protein comprising SEQ ID NO:2, and comparing the status so determined to the status of 36P6D5 gene products in a corresponding normal breast, colon, kidney or pancreatic sample, the presence of elevated status of 36P6D5 gene products in the test sample relative to the normal sample providing an indication of dysregulated breast, colon, kidney or pancreatic cell growth within the individual.

6. A method of examining a biological breast, colon, kidney or pancreatic sample for evidence of dysregulated cellular growth comprising comparing the status of 36P6D5 in the biological breast, colon, kidney or pancreatic sample to the status of 36P6D5 in a corresponding normal breast, colon, kidney or pancreatic sample, wherein the status of 36P6D5 in the biological sample is evaluated by examining levels of 36P6D5 protein expression, wherein the 36P6D5 protein comprises SEQ ID NO:2, and wherein elevations in the status of 36P6D5 in the biological sample are associated with dysregulated breast, colon, kidney or pancreatic cellular growth.

7. A method of diagnosing the presence of breast, colon, kidney or pancreatic cancer in an individual comprising:
  (a) determining the level of 36P6D5 protein expressed in a test breast, colon, kidney or pancreatic sample obtained from the individual, wherein the 36P6D5 protein comprises SEQ ID NO:2; and (b) comparing the level so determined to the level of 36P6D5 protein expressed in a comparable known normal breast, colon, kidney or pancreatic tissue sample, the presence of elevated 36P6D5 protein in the test sample relative to the normal tissue sample providing an indication of the presence of cancer.

8. The method of claim 7, wherein the sample is a colon sample.

9. The method of claim 7, wherein determining the level of 36P6D5 protein expressed in the test sample comprises contacting the sample with an antibody that specifically binds 36P6D5 protein comprising the amino acid sequence of SEQ ID NO:2.

10. The method of claim 9, wherein the antibody comprises a polyclonal antibody.

11. The method of claim 9, wherein the antibody comprises a monoclonal antibody.

12. The method of claim 1, wherein breast tissue is examined.

13. The method of claim 1, wherein colon tissue is examined.

14. The method of claim 1, wherein kidney tissue is examined.

15. The method of claim 1, wherein pancreatic tissue is examined.

16. The method of claim 5, wherein the status of the 36P6D5 gene products is determined in a test breast tissue sample.

17. The method of claim 5, wherein the status of the 36P6D5 gene products is determined in a test colon tissue sample.

18. The method of claim 5, wherein the status of the 36P6D5 gene products is determined in a test kidney tissue sample.

19. The method of claim 5, wherein the status of the 36P6D5 gene products is determined in a test pancreatic tissue sample.

20. The method of claim 6, wherein a breast sample is examined.

21. The method of claim 6, wherein a colon sample is examined.

22. The method of claim 6, wherein a kidney sample is examined.

23. The method of claim 6, wherein a pancreatic sample is examined.

24. The method of claim 7, wherein the sample is a breast sample.

25. The method of claim 7, wherein the sample is a kidney sample.

26. The method of claim 7, wherein the sample is a pancreatic sample.

* * * * *

SEQUENCE LISTING

<160> NUMBER OF SEQ ID NOS: 28

<210> SEQ ID NO 1
<211> LENGTH: 913
<212> TYPE: DNA
<213> ORGANISM: Homo Sapiens

<400> SEQUENCE: 1
ctggctgcgg tcgcctggga gctgccgcca gggccaggag gggagcggca cctggaagat      60
gcgcccattg gctggtggcc tgctcaaggt ggtgttcgtg gtcttcgcct ccttgtgtgc     120
ctggtattcg gggtacctgc tcgcagagct cattccagat gcaccctgt ccagtgctgc     180

-continued

```
ctatagcatc cgcagcatcg gggagaggcc tgtcctcaaa gctccagtcc ccaaaaggca    240
aaaatgtgac cactggactc cctgcccatc tgacacctat gcctacaggt tactcagcgg    300
aggtggcaga agcaagtacg ccaaaatctg ctttgaggat aacctactta tgggagaaca    360
gctgggaaat gttgccagag gaataaacat tgccattgtc aactatgtaa ctgggaatgt    420
gacagcaaca cgatgttttg atatgtatga aggcgataac tctggaccga tgacaaagtt    480
tattcagagt gctgctccaa atccctgct cttcatggtg acctatgacg acggaagcac    540
aagactgaat aacgatgcca agaatgccat agaagcactt ggaagtaaag aaatcaggaa    600
catgaaattc aggtctagct gggtatttat tgcagcaaaa ggcttggaac tccctccga     660 aattcagaga gaaagatca accactctga tgctaagaac aacagatatt ctggctggcc     720
tgcagagatc cagatagaag gctgcatacc caaagaacga agctgacact gcagggtcct    780
gagtaaatgt gttctgtata acaaatgca gctggaatcg ctcaagaatc ttatttttct    840
aaatccaaca gcccatattt gatgagtatt ttgggtttgt tgtaaaccaa tgaacatttg    900
ctagttgtaa aaa                                                       913
```

```
<210> SEQ ID NO 2
<211> LENGTH: 235
<212> TYPE: PRT
<213> ORGANISM: Homo Sapiens

<400> SEQUENCE: 2

Met Arg Pro Leu Ala Gly Gly Leu Leu Lys Val Phe Val Val Phe
 1               5                  10                  15

Ala Ser Leu Cys Ala Trp Tyr Ser Gly Tyr Leu Leu Ala Glu Leu Ile
            20                  25                  30

Pro Asp Ala Pro Leu Ser Ser Ala Ala Tyr Ser Ile Arg Ser Ile Gly
        35                  40                  45

Glu Arg Pro Val Leu Lys Ala Pro Val Pro Lys Arg Gln Lys Cys Asp
    50                  55                  60

His Trp Thr Pro Cys Pro Ser Asp Thr Tyr Ala Tyr Arg Leu Leu Ser
65                  70                  75                  80

Gly Gly Gly Arg Ser Lys Tyr Ala Lys Ile Cys Phe Glu Asp Asn Leu
                85                  90                  95

Leu Met Gly Glu Gln Leu Gly Asn Val Ala Arg Gly Ile Asn Ile Ala
            100                 105                 110

Ile Val Asn Tyr Val Thr Gly Asn Val Thr Ala Thr Arg Cys Phe Asp
        115                 120                 125

Met Tyr Glu Gly Asp Asn Ser Gly Pro Met Thr Lys Phe Ile Gln Ser
    130                 135                 140

Ala Ala Pro Lys Ser Leu Leu Phe Met Val Thr Tyr Asp Asp Gly Ser
145                 150                 155                 160

Thr Arg Leu Asn Asn Asp Ala Lys Asn Ala Ile Glu Ala Leu Gly Ser
                165                 170                 175

Lys Glu Ile Arg Asn Met Lys Phe Arg Ser Ser Trp Val Phe Ile Ala
            180                 185                 190

Ala Lys Gly Leu Glu Leu Pro Ser Glu Ile Gln Arg Glu Lys Ile Asn
        195                 200                 205

His Ser Asp Ala Lys Asn Asn Arg Tyr Ser Gly Trp Pro Ala Glu Ile
    210                 215                 220

Gln Ile Glu Gly Cys Ile Pro Lys Glu Arg Ser
225                 230                 235
```

<210> SEQ ID NO 3
<211> LENGTH: 14
<212> TYPE: DNA
<213> ORGANISM: Artificial Sequence
<220> FEATURE:
<223> OTHER INFORMATION: Primer

<400> SEQUENCE: 3
ttttgatcaa gctt                                                        14

<210> SEQ ID NO 4
<211> LENGTH: 42
<212> TYPE: DNA
<213> ORGANISM: Artificial Sequence
<220> FEATURE:
<223> OTHER INFORMATION: Adaptor

<400> SEQUENCE: 4
ctaatacgac tcactatagg gctcgagcgg ccgcccgggc ag                          42

<210> SEQ ID NO 5
<211> LENGTH: 12
<212> TYPE: DNA
<213> ORGANISM: Artificial Sequence
<220> FEATURE:
<223> OTHER INFORMATION: Adaptor

<400> SEQUENCE: 5
ggcccgtcct ag                                                          12

<210> SEQ ID NO 6
<211> LENGTH: 40
<212> TYPE: DNA
<213> ORGANISM: Artificial Sequence
<220> FEATURE:
<223> OTHER INFORMATION: Adaptor

<400> SEQUENCE: 6
gtaatacgac tcactatagg gcagcgtggt cgcggccgag                             40

<210> SEQ ID NO 7
<211> LENGTH: 10
<212> TYPE: DNA
<213> ORGANISM: Artificial Sequence
<220> FEATURE:
<223> OTHER INFORMATION: Adaptor

<400> SEQUENCE: 7
cggctcctag                                                             10

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
ctaatacgac tcactatagg gc                                               22

<210> SEQ ID NO 9
<211> LENGTH: 22
<212> TYPE: DNA
<213> ORGANISM: Artificial Sequence
<220> FEATURE:

-continued

<223> OTHER INFORMATION: Primer

<400> SEQUENCE: 9
tcgagcggcc gcccgggcag ga					22

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
agcgtggtcg cggccgagga					20

<210> SEQ ID NO 11
<211> LENGTH: 25
<212> TYPE: DNA
<213> ORGANISM: Artificial Sequence
<220> FEATURE:
<223> OTHER INFORMATION: Primer

<400> SEQUENCE: 11
atatcgccgc gctcgtcgtc gacaa					25

<210> SEQ ID NO 12
<211> LENGTH: 26
<212> TYPE: DNA
<213> ORGANISM: Artificial Sequence
<220> FEATURE:
<223> OTHER INFORMATION: Primer

<400> SEQUENCE: 12
agccacacgc agctcattgt agaagg					26

<210> SEQ ID NO 13
<211> LENGTH: 23
<212> TYPE: DNA
<213> ORGANISM: Artificial Sequence
<220> FEATURE:
<223> OTHER INFORMATION: Primer

<400> SEQUENCE: 13
gcattcttgg catcgttatt cag					23

<210> SEQ ID NO 14
<211> LENGTH: 24
<212> TYPE: DNA
<213> ORGANISM: Artificial Sequence
<220> FEATURE:
<223> OTHER INFORMATION: Primer

<400> SEQUENCE: 14
taactgggaa tgtgacagca acac					24

<210> SEQ ID NO 15
<211> LENGTH: 181
<212> TYPE: PRT
<213> ORGANISM: Homo Sapiens

<400> SEQUENCE: 15

Glu Ser Ser Val Thr Ala Ala Pro Arg Ala Arg Lys Tyr Lys Cys Gly
 1               5                  10                  15

Leu Pro Gln Pro Cys Pro Glu Glu His Leu Ala Phe Arg Val Val Ser
            20                  25                  30

```
Gly Ala Ala Asn Val Ile Gly Pro Lys Ile Cys Leu Glu Asp Lys Met
             35                  40                  45

Leu Met Ser Ser Val Lys Asp Asn Val Gly Arg Gly Leu Asn Ile Ala
 50                  55                  60

Leu Val Asn Gly Val Ser Gly Glu Leu Ile Glu Ala Arg Ala Phe Asp
 65                  70                  75                  80

Met Trp Ala Gly Asp Val Asn Asp Leu Leu Lys Phe Ile Arg Pro Leu
                 85                  90                  95

His Glu Gly Thr Leu Val Phe Val Ala Ser Tyr Asp Asp Pro Ala Thr
            100                 105                 110

Lys Met Asn Glu Glu Thr Arg Lys Leu Phe Ser Glu Leu Gly Ser Arg
        115                 120                 125

Asn Ala Lys Glu Leu Ala Phe Arg Asp Ser Trp Val Phe Val Gly Ala
130                 135                 140

Lys Gly Val Gln Asn Lys Ser Pro Phe Glu Gln His Val Lys Asn Ser
145                 150                 155                 160

Lys His Ser Asn Lys Tyr Glu Gly Cys Pro Glu Ala Leu Glu Met Glu
                165                 170                 175

Gly Cys Ile Pro Arg
            180

<210> SEQ ID NO 16
<211> LENGTH: 174
<212> TYPE: PRT
<213> ORGANISM: Homo Sapiens

<400> SEQUENCE: 16

Pro Pro Arg Tyr Lys Cys Gly Ile Ser Lys Ala Cys Pro Glu Lys His
 1               5                  10                  15

Phe Ala Phe Lys Met Ala Ser Gly Ala Ala Asn Val Val Gly Pro Lys
                 20                  25                  30

Ile Cys Leu Glu Asp Asn Val Leu Met Ser Gly Val Lys Asn Asn Val
             35                  40                  45

Gly Arg Gly Ile Asn Val Ala Leu Ala Asn Gly Lys Thr Gly Glu Val
 50                  55                  60

Leu Asp Thr Lys Tyr Phe Asp Met Trp Gly Gly Asp Val Ala Pro Phe
 65                  70                  75                  80

Ile Glu Phe Leu Lys Ala Ile Gln Asp Gly Thr Ile Val Leu Met Gly
                 85                  90                  95

Thr Tyr Asp Asp Gly Ala Thr Lys Leu Asn Asp Glu Ala Arg Arg Leu
            100                 105                 110

Ile Ala Asp Leu Gly Ser Thr Ser Ile Thr Asn Leu Gly Phe Arg Asp
        115                 120                 125

Asn Trp Val Phe Cys Gly Gly Lys Gly Ile Lys Thr Lys Ser Pro Phe
130                 135                 140

Glu Gln His Ile Lys Asn Asn Lys Asp Thr Asn Lys Tyr Glu Gly Trp
145                 150                 155                 160

Pro Glu Val Val Glu Met Glu Gly Cys Ile Pro Gln Lys Gln
                165                 170

<210> SEQ ID NO 17
<211> LENGTH: 24
<212> TYPE: DNA
<213> ORGANISM: Artificial Sequence
<220> FEATURE:
<223> OTHER INFORMATION: Primer
```

```
<400> SEQUENCE: 17
atacccaaag aacgaagctg acac                                          24

<210> SEQ ID NO 18
<211> LENGTH: 24
<212> TYPE: DNA
<213> ORGANISM: Artificial Sequence
<220> FEATURE:
<223> OTHER INFORMATION: Primer

<400> SEQUENCE: 18
tactcatcaa atatgggctg ttgg                                          24

<210> SEQ ID NO 19
<211> LENGTH: 9
<212> TYPE: PRT
<213> ORGANISM: Homo Sapiens

<400> SEQUENCE: 19

Gly Leu Leu Lys Val Val Phe Val Val
 1               5

<210> SEQ ID NO 20
<211> LENGTH: 9
<212> TYPE: PRT
<213> ORGANISM: Homo Sapiens

<400> SEQUENCE: 20

Leu Met Gly Glu Gln Leu Gly Asn Val
 1               5

<210> SEQ ID NO 21
<211> LENGTH: 9
<212> TYPE: PRT
<213> ORGANISM: Homo Sapiens

<400> SEQUENCE: 21

Leu Leu Ala Glu Leu Ile Pro Asp Ala
 1               5

<210> SEQ ID NO 22
<211> LENGTH: 9
<212> TYPE: PRT
<213> ORGANISM: Homo Sapiens

<400> SEQUENCE: 22

Leu Leu Ala Glu Leu Ile Pro Asp Ala
 1               5

<210> SEQ ID NO 23
<211> LENGTH: 9
<212> TYPE: PRT
<213> ORGANISM: Homo Sapiens

<400> SEQUENCE: 23

Val Val Phe Val Val Phe Ala Ser Leu
 1               5

<210> SEQ ID NO 24
<211> LENGTH: 9
<212> TYPE: PRT
<213> ORGANISM: Homo Sapiens

<400> SEQUENCE: 24
```

```
Gly Gly Leu Leu Lys Val Val Phe Val
1               5

<210> SEQ ID NO 25
<211> LENGTH: 9
<212> TYPE: PRT
<213> ORGANISM: Homo Sapiens

<400> SEQUENCE: 25

Phe Ile Ala Ala Lys Gly Leu Glu Leu
1               5

<210> SEQ ID NO 26
<211> LENGTH: 9
<212> TYPE: PRT
<213> ORGANISM: Homo Sapiens

<400> SEQUENCE: 26

Lys Ile Cys Phe Glu Asp Asn Leu Leu
1               5

<210> SEQ ID NO 27
<211> LENGTH: 9
<212> TYPE: PRT
<213> ORGANISM: Homo Sapiens

<400> SEQUENCE: 27

Ile Asn Ile Ala Ile Val Asn Tyr Val
1               5

<210> SEQ ID NO 28
<211> LENGTH: 9
<212> TYPE: PRT
<213> ORGANISM: Homo Sapiens

<400> SEQUENCE: 28

Asn Met Lys Phe Arg Ser Ser Trp Val
1               5
```